US012552788B2

(12) United States Patent
Garcia-Sastre et al.

(10) Patent No.: US 12,552,788 B2
(45) Date of Patent: Feb. 17, 2026

(54) IMDQ-PEG-CHOL ADJUVANT AND USES THEREOF

(71) Applicants: ICAHN SCHOOL OF MEDICINE AT MOUNT SINAI, New York, NY (US); UNIVERSITEIT GENT, Ghent (BE)

(72) Inventors: Adolfo Garcia-Sastre, New York, NY (US); Michael Schotsaert, New York, NY (US); Angela Choi, Boston, MA (US); Bruno De Geest, De Pinte (BE); Jana De Vrieze, Lievegem (BE)

(73) Assignees: ICAHN SCHOOL OF MEDICINE AT MOUNT SINAI, New York, NY (US); UNIVERSITEIT GENT, Ghent (BE)

( * ) Notice: Subject to any disclaimer, the term of this patent is extended or adjusted under 35 U.S.C. 154(b) by 491 days.

(21) Appl. No.: 18/030,302

(22) PCT Filed: Oct. 7, 2021

(86) PCT No.: PCT/US2021/054024

§ 371 (c)(1),
(2) Date: Apr. 5, 2023

(87) PCT Pub. No.: WO2022/076723

PCT Pub. Date: Apr. 14, 2022

(65) Prior Publication Data

US 2023/0373997 A1 Nov. 23, 2023

Related U.S. Application Data

(60) Provisional application No. 63/089,442, filed on Oct. 8, 2020.

(51) Int. Cl.

| | |
|---|---|
| ***C07D 471/02*** | (2006.01) |
| ***A61K 39/215*** | (2006.01) |
| ***A61P 31/14*** | (2006.01) |
| ***C07D 471/04*** | (2006.01) |
| *A61K 39/00* | (2006.01) |

(52) U.S. Cl.
CPC .......... *C07D 471/04* (2013.01); *A61K 39/215* (2013.01); *A61P 31/14* (2018.01); *A61K 2039/55511* (2013.01); *A61K 2039/575* (2013.01)

(58) Field of Classification Search
CPC .................................................... C07D 471/02
See application file for complete search history.

(56) References Cited

PUBLICATIONS

Jangra, Sonia, et al. "Sterilizing Immunity against SARS-CoV-2 Infection in Mice by a Single-Shot and Modified Imidazoquinoline TLR7/8 Agonist-Adjuvanted Recombinant Spike Protein Vaccine." Published Oct. 23, 2020. (Year: 2020).*
European Patent Office, "Extended European Search Report," regarding Application No. 21878555.8, 10 pages, dated Oct. 4, 2024.
De Vrieze et al., "Potent Lymphatic Translocation and Spatial Control Over Innate Immune Activation by Polymer-Lipid Amphiphile Conjugates of Small-Molecule TLR7/8 Agonists," Angew. Chem. Int. Ed. 2019, 58, 6 pages, dated 2019.
He, Z., et al., "Recent development of poly(ethylene glycol)-cholesterol conjugates as drug delivery systems," International Journal of Pharmaceutics, vol. 469, 11 pages, dated Apr. 23, 2014.

* cited by examiner

*Primary Examiner* — John S Kenyon
(74) *Attorney, Agent, or Firm* — Lathrop GPM LLP; Malaika O. D. Tyson

(57) ABSTRACT

Provided herein are lipidated imidazoquinoline compounds and compositions comprising such compounds. The lipidated imidazoquinoline compounds may be used as an adjuvant to enhance to immune response elicited by an antigen of interest. Accordingly, also provided herein are methods for enhancing the immune response of an antigen of interest in a subject, comprising administering to the subject an antigen of interest with a lipidated imidazoquinoline compound described herein in an immunogenic composition, or administering to the subject a composition comprising a lipidated imidazoquinoline compound described herein in combination with (e.g., prior to, concurrently, or subsequently) the administration of an immunogenic composition comprising an antigen of interest to the subject.

22 Claims, 28 Drawing Sheets

Figure 1A:
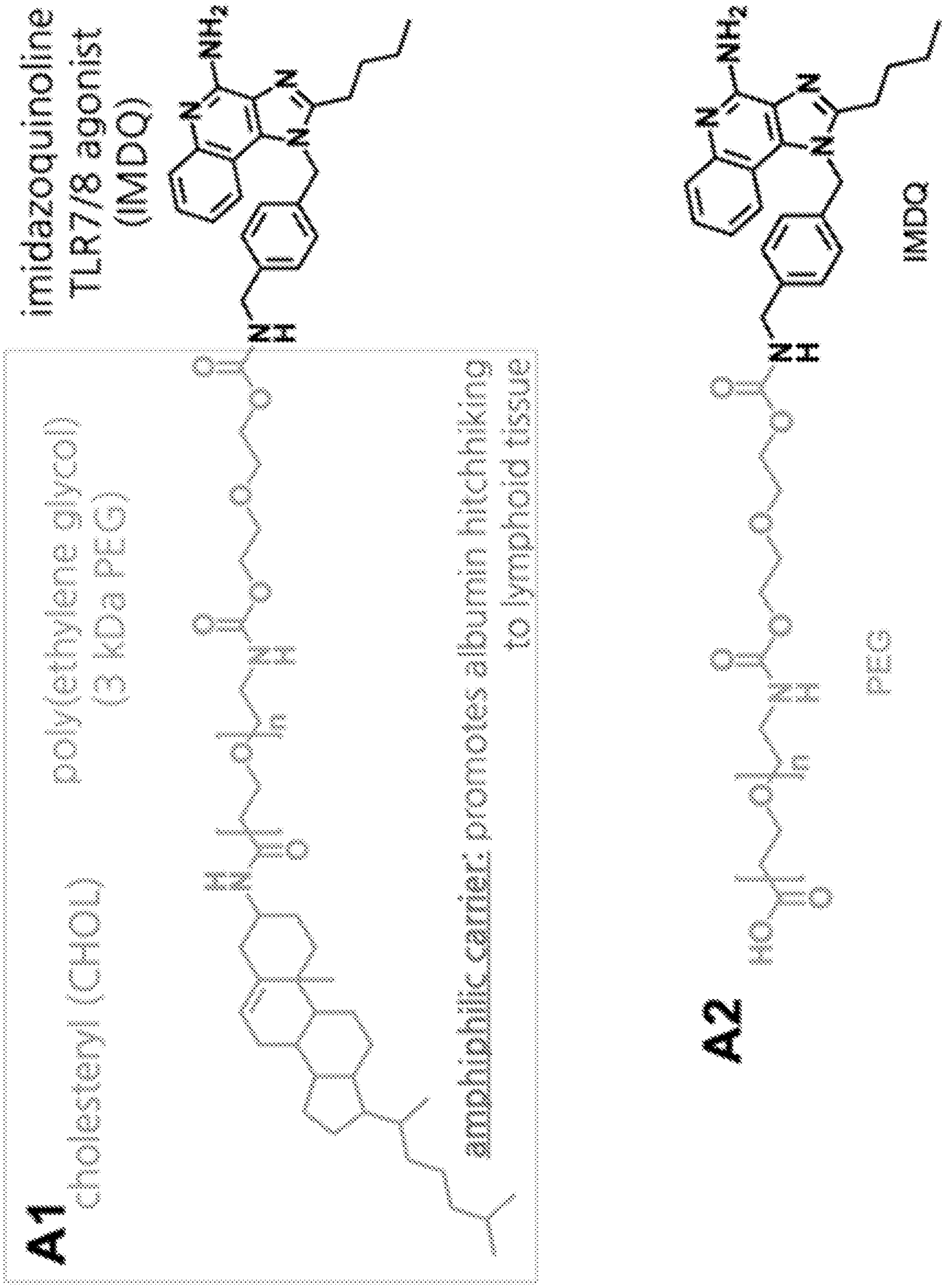

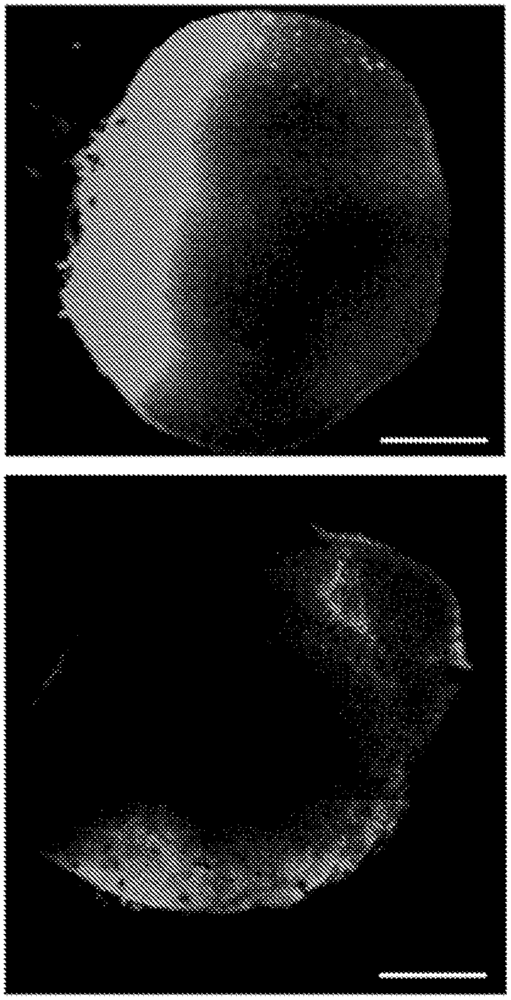
FIG. 3B1
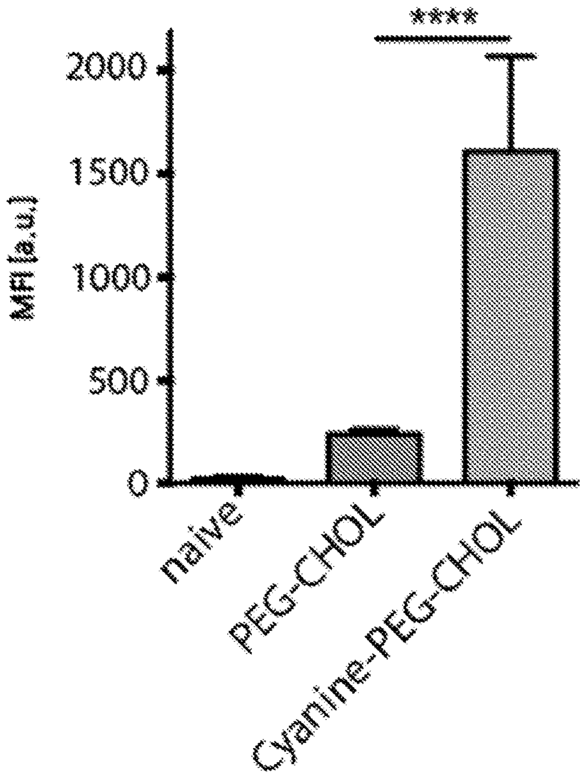
FIG. 3B2

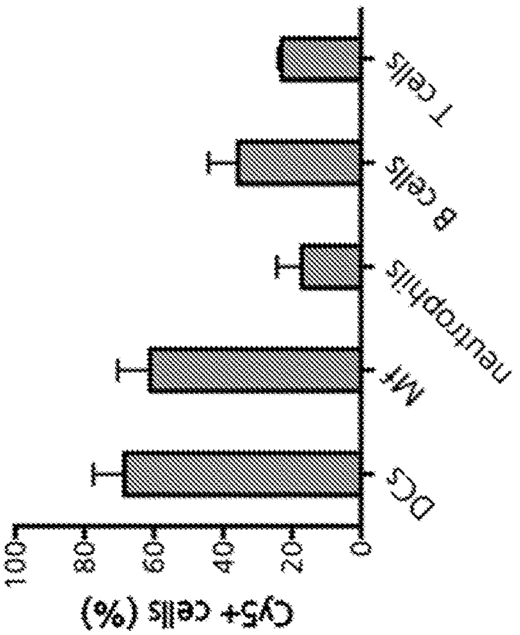
FIG. 3C
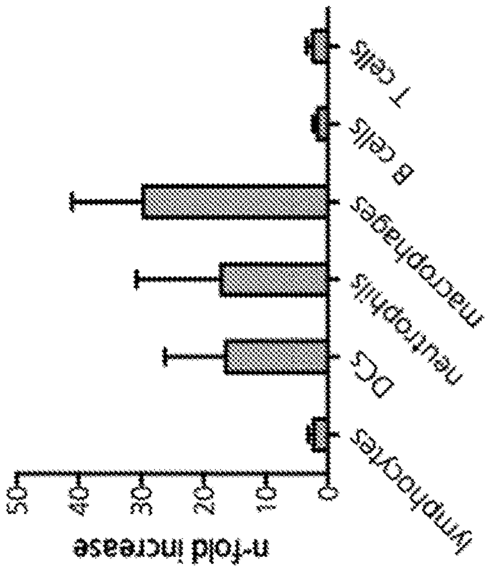
FIG. 3D1
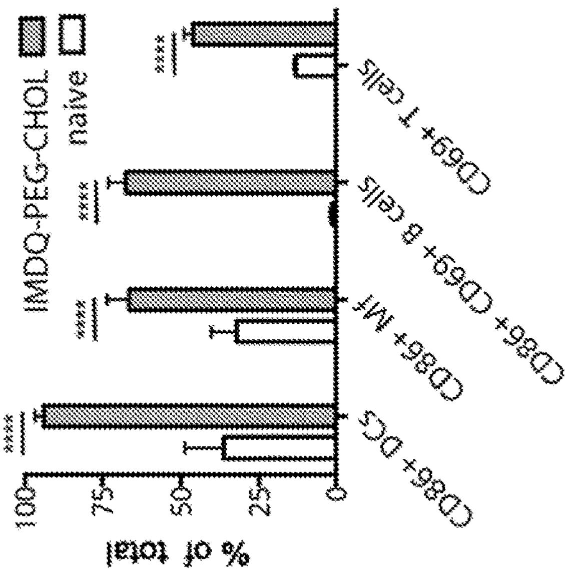
FIG. 3D2

FIG. 5C1

FIG. 5C2

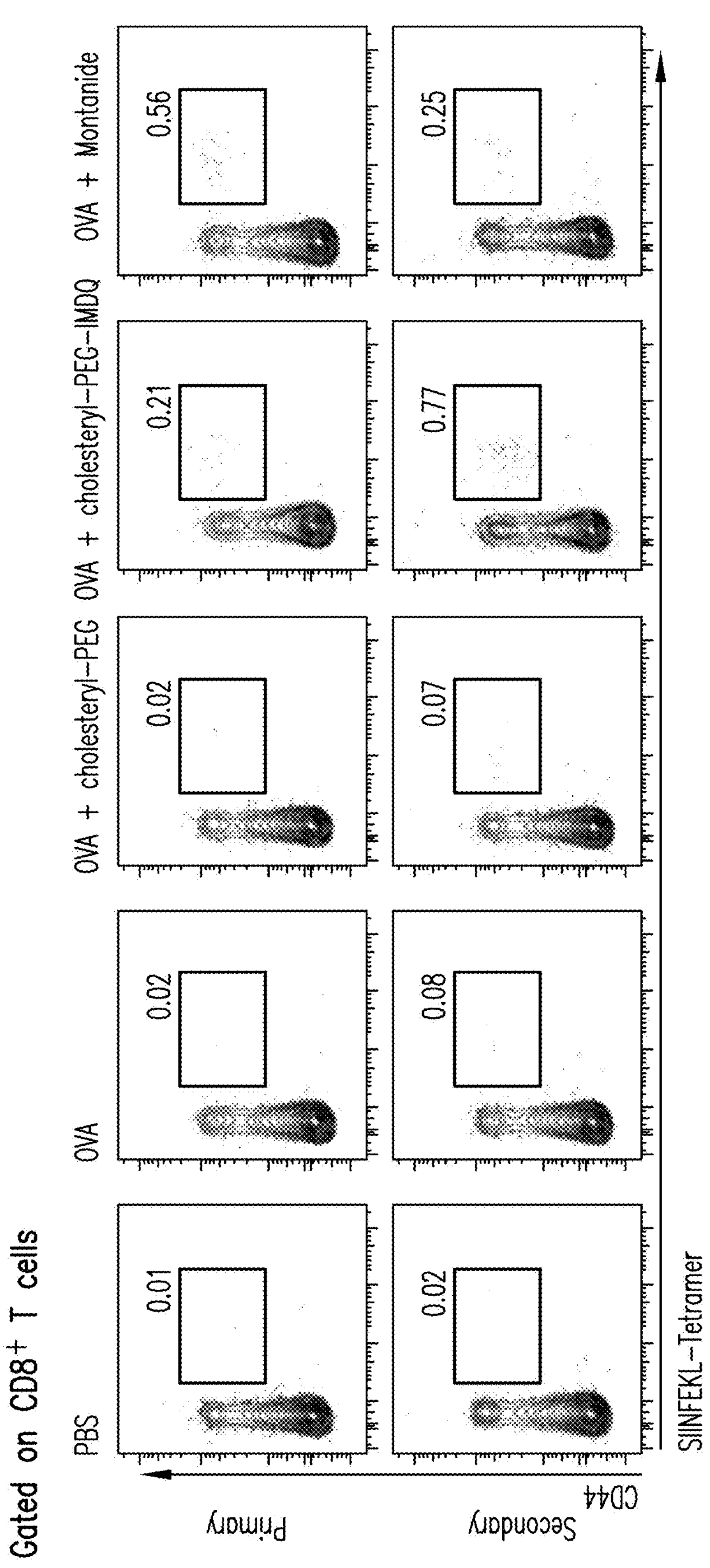
FIG. 11B1

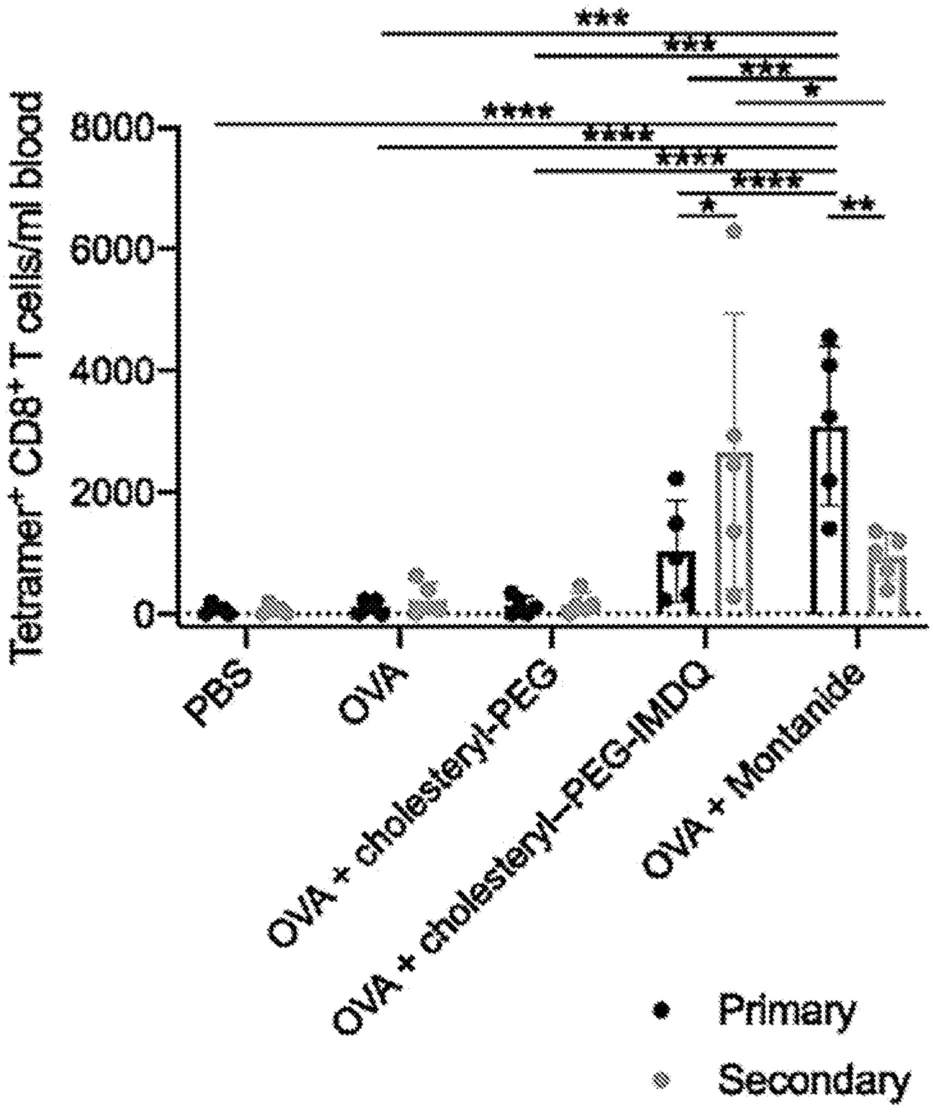
FIG. 11B2

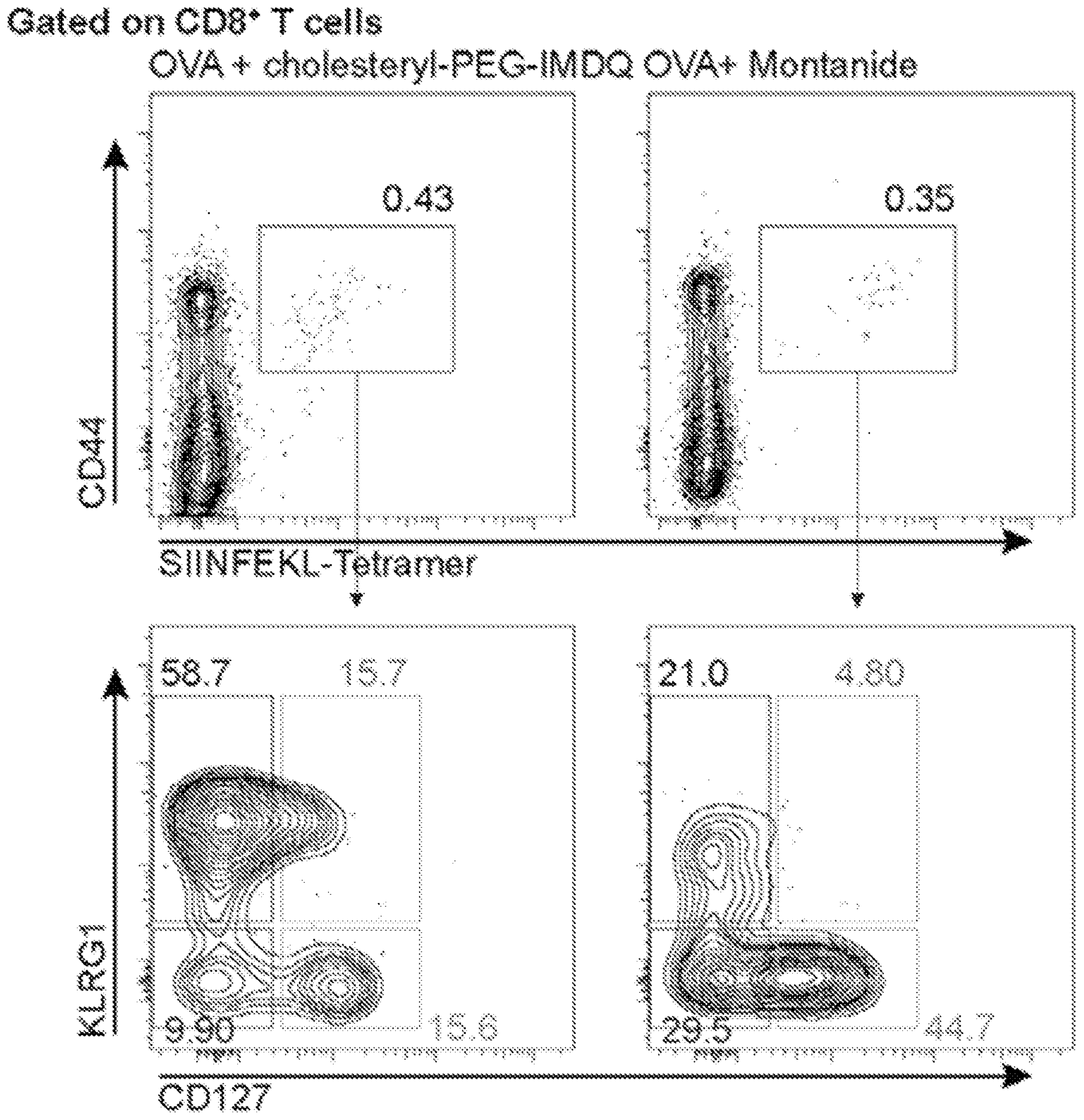
FIG. 11C1

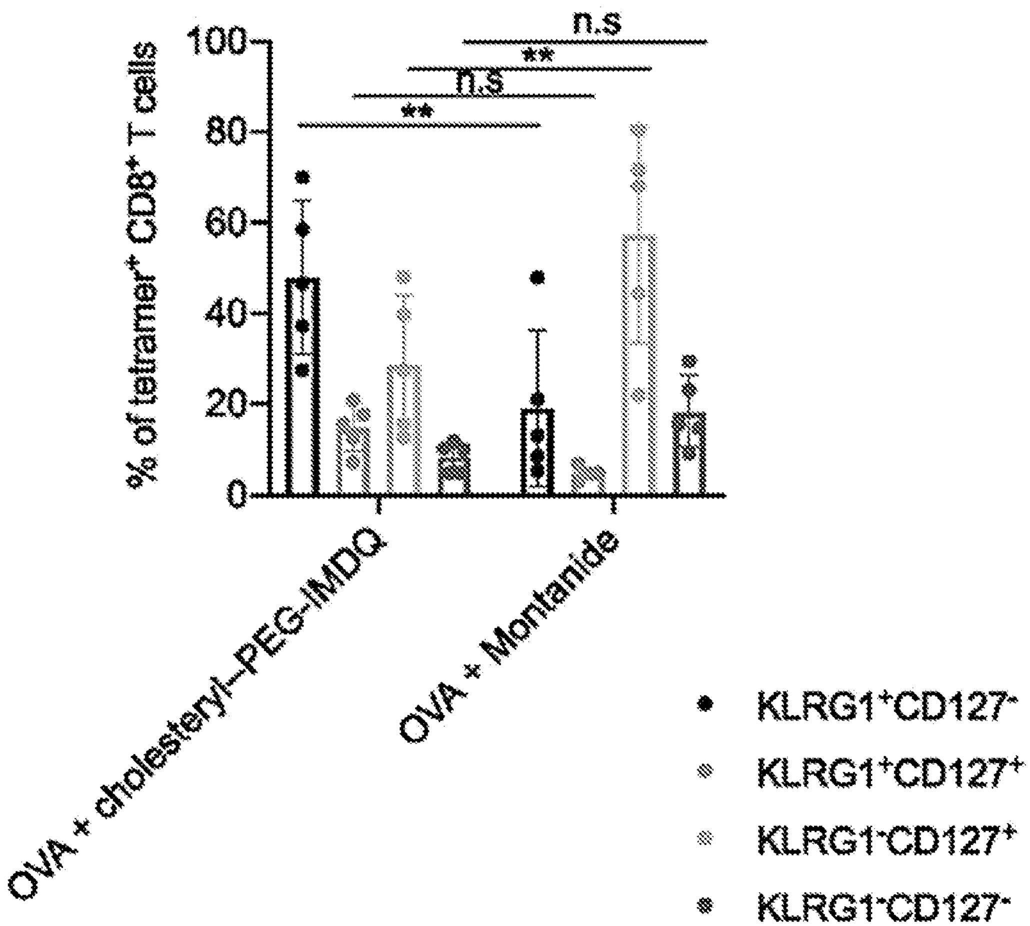
FIG. 11C2

IMDQ-PEG-CHOL ADJUVANT AND USES THEREOF

CROSS-REFERENCE TO RELATED APPLICATIONS

This application is a U.S. National Stage Application under 35 U.S.C. § 371 of International Patent Application No. PCT/US2021/054024, filed Oct. 7, 2021, which claims the benefit of U.S. Provisional Patent Application No. 63/089,442, filed on Oct. 8, 2020, the disclosure of each of which is incorporated by reference herein in its entirety.

This invention was made with government support under HHSN272201400008C awarded by the National Institutes of Health. The government has certain rights in the invention.

1. INTRODUCTION

Provided herein are lipidated imidazoquinoline compounds and compositions comprising such compounds. The lipidated imidazoquinoline compounds may be used as an adjuvant to enhance to immune response elicited by an antigen of interest. Accordingly, also provided herein are methods for enhancing the immune response of an antigen of interest in a subject, comprising administering to the subject an antigen of interest with a lipidated imidazoquinoline compound described herein in an immunogenic composition, or administering to the subject a composition comprising a lipidated imidazoquinoline compound described herein in combination with (e.g., prior to, concurrently, or subsequently) the administration of an immunogenic composition comprising an antigen of interest to the subject.

2. BACKGROUND

Severe acute respiratory syndrome coronavirus 2 (SARS-CoV-2), also known as COVID-19, is a beta-coronavirus which belongs to the family of Coronaviridae and is currently responsible for the third human coronavirus outbreak in the past 20 years, after SARS (now often referred to as SARS-CoV-1) in 2002/03 and MERS (Middle east respiratory syndrome) in 2012 (1). SARS-CoV-2 was first identified in Wuhan, China in December 2020 (2,3). This COVID-19 pandemic has caused unprecedented morbidity, mortality and global economic instability. SARS-CoV-2 is highly pathogenic and is believed to spread mainly through respiratory droplets and aerosols. The current preventive measures include quarantine, isolation and physical social distancing. Thus far, therapeutic drugs are of limited use in the clinic, and no specific vaccine is available yet, therefore calling for an urgent need for development of effective vaccines to restrict disease as well as viral spread.

More than hundred candidate vaccines, consisting of multiple vaccine types such as recombinant viral epitopes (surface glycoprotein), adenovirus-based vectors (e.g. recombinant replication incompetent Ad-5), purified inactivated or live-attenuated virus, virus like particles (VLPs) and DNA or RNA based vaccine formulations, are currently being investigated (4,5). At present mRNA-based vaccines formulated in lipid nanoparticles and viral vector-based vaccines have reached late stage of clinical development, entering phase 3 testing. For these vaccines, pre-clinical data in rodent models has also been generated supporting the hypothesis that these vaccines can effectively prevent viral infection. However, little is known on whether recombinant protein vaccines are capable of conferring protective immunity. In contrast to the aforementioned mRNA and viral vector-based vaccines, recombinant protein vaccines are simpler as they consist of a single entity antigen and—in contrast to viral vectors—do not require antigen expression in the vaccinees. Compared to mRNA vaccines, recombinant protein vaccines do not require complex (lipid) nanoparticle formulations to overcome the formidable barrier of the endosomal membrane before reaching the cytoplasm which is the subcellular target compartment for the antigen-expressing mRNA. Moreover, thus far only one mRNA-based vaccine has been licensed, which might pose additional hurdles in view of mass manufacturing in world-wide immunization campaigns.

Hence, exploring the viability of a recombinant protein Covid-19 vaccine might be of considerable relevance. SARS-CoV-2 consists of a >30 kb single-stranded positive strand RNA genome which encodes four major structural proteins, Spike (S), Membrane (M), Nucleocapsid (N) and Envelope (E). The Spike protein comprises a homotrimeric structure which is present all over the surface of the virus and facilitates the viral attachment and entry into the host cells. Like SARS-CoV-1, SARS-CoV-2 S protein gains entry into host cells via human angiotensin-converting enzyme 2 (hACE-2) receptors on the host cell surface via its receptor-binding domain (RBD) (1)(6). Subsequently, the membrane-associated serine protease such as TMPRSS2 or endosomal-associated proteases such as cathepsins cleaves the S protein, thereby promoting efficient fusion of the viral membrane to the host cell membrane, followed by release of viral content into the cell cytoplasm, where the virus subsequently replicates. The viral infection usually begins in the oral/nasal cavity and once released, it gradually establishes itself in type-II pneumocytes of the lower respiratory air tract and enterocytes in the gastrointestinal tract (7,8).

As recombinant protein antigens are poorly immunogenic and are incapable of mounting antigen-specific immunity of sufficient quality, amplitude and duration, co-administration of adjuvants that shape B cell and T cell responses are indispensable. Adjuvants like alum and oil-in-water emulsions can act through a multitude of mechanisms. More defined small molecule adjuvants that potently activate innate immune cells by triggering specific innate immune receptors might be more relevant for anti-viral vaccine design. The Toll like receptors 7 and 8 (TLR7/8) are widely distributed amongst innate immune cell subsets over a broad range of species, including mouse and human (9). Akin to be an endosomal pattern recognition receptor for viral RNA, triggering of these receptors provokes robust type I interferon production that can skew a Th1-type adaptive immune response against co-administered antigen (10). The latter are characterized by robust antibody titers capable of inducing viral neutralization through a variety of mechanisms, including Fc-mediated innate immune killing as well as inducing CD4- and CD8 T-cell based immunological memory. Moreover, vaccines adjuvanted with TLR7/8 ligands have been shown to confer protective immunity in both mouse and non-human primate models against neo-antigen expressing cancers and viral infection, including HIV and RSV.

Being a well-defined small molecule, imidazoquinoline is a TLR7/8 agonist (11) that holds a massive technological advantage in terms of production and physicochemical stability. However, their pharmacokinetic profile is characterized by rapid systemic dissemination upon local (e.g. subcutaneous or intramuscular) administration, thereby causing unwanted innate immune activation at multiple distal tissues (12), which is currently a strong limitation for applying TLR7/8 agonists in mass immunization campaigns.

Thus, there is a need for adjuvants that enhance the immune response to an antigen, and have good pharmacokinetic and safety profiles.

3. SUMMARY

In one aspect, provide herein is a compound having the following structure:

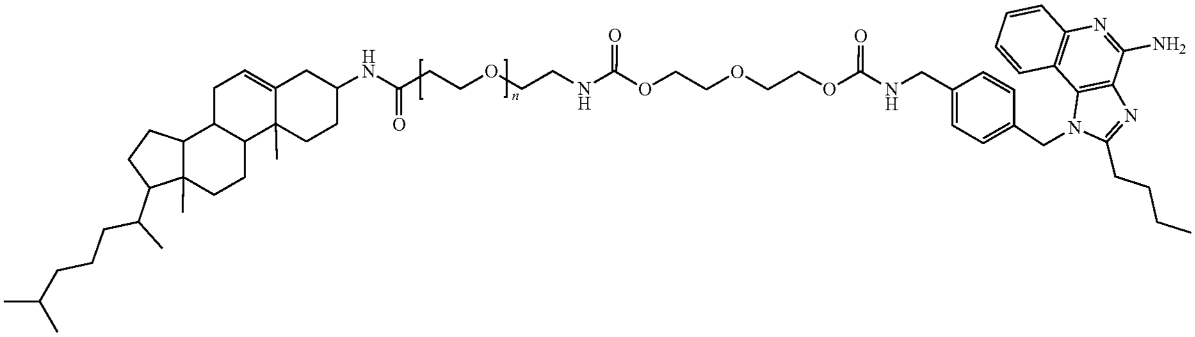

or an enantiomer, a mixture of enantiomers, a tautomer, or a pharmaceutically acceptable salt thereof, wherein n is an integer from 10 to 200. In another aspect, provided herein is a compound having the following structure:

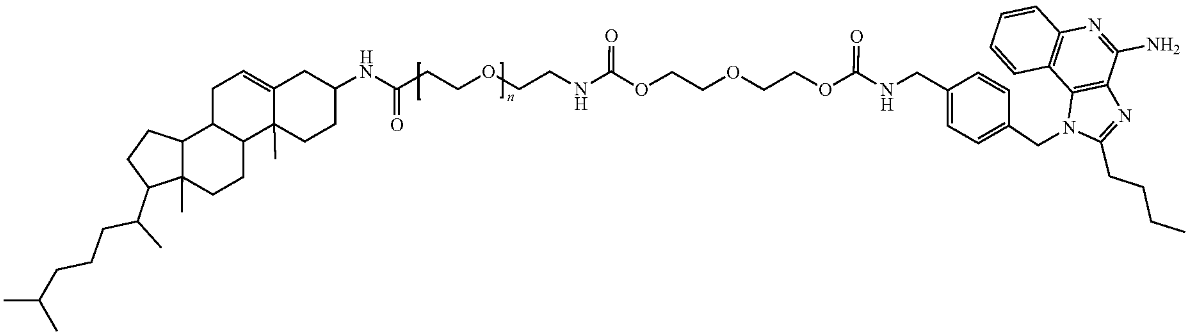

wherein n is an integer from 10 to 200. In a specific embodiment, the compound is described in Section 6, infra.

In another aspect, provided herein is a pharmaceutical composition comprising a compound described herein, and a pharmaceutically acceptable carrier. In another aspect, provided herein is an immunogenic composition comprising the compound described herein, and an antigen of interest. In certain embodiments, the antigen of interest is a SARS-CoV-2 antigen. In a specific embodiment, the SARS-CoV-2 antigen comprises a SARS-CoV-2 spike protein ectodomain with amino acid substitutions of RRAR to A at amino acid residues corresponding to amino acid residues 682 to 685 of GenBank Accession No. MN908947.3, and amino acid substitutions to prolines at amino acid residues corresponding to amino acid residues 986 and 987 of GenBank Accession No. MN908947.3. The ectodomain may be directly or indirectly linked to a trimerization domain. In a specific embodiment, the trimerization domain is a T4 foldon trimerization domain. In certain embodiments, the SARS-CoV2 antigen comprises a tag. The trimerization domain may be directly or indirectly linked to a tag. In some embodiments, the tag is a hexa-histidine tag or flag tag. In some embodiments, the antigen of interest is an infectious disease antigen. In certain embodiments, the antigen of interest is a viral antigen, a bacteria antigen, a fungal antigen, or a parasitic antigen. In some embodiments, the antigen of interest comprises an inactivated virus. In a specific embodiment, the inactivated virus is influenza virus. In specific embodiments, the antigen of interest is a trivalent or quadravalent inactivated influenza virus composition. In specific embodiments, the antigen of interest comprises a split influenza virus. In specific embodiments, the antigen of interest is an infectious disease antigen. In certain embodiments, the antigen of interest is a RSV antigen, human Metapneumovirus antigen, MERS-CoV antigen, Lassa virus antigen, Japanese encephalitis antigen, or hepatitis A virus antigen. In some embodiments, the antigen of interest is a *Clostridium tetani* antigen, *Bacillus* antigen, *Bordetella pertussis* antigen, *Streptococcus pneumoniae* antigen, *Neisseria meningitides* antigen, *Haemophilus influenzae* antigen, or *Corynebacterium* diphtherias antigen. In certain embodiments, the *Bacillus* antigen is a *Bacillus anthracis* antigen. In some embodiments, the antigen of interest is a cancer antigen. In certain embodiments, the immunogenic composition is administered subcutaneously or intramuscularly.

In another aspect, provided herein is a method of inducing an immune response to an antigen of interest in a subject, comprising administering to the subject an immunogenic composition described herein. In a specific embodiment, the subject is a human subject. In some embodiments, the antigen of interest is an infectious disease antigen. In certain embodiments, the antigen of interest is a viral antigen, a bacteria antigen, a fungal antigen, or a parasitic antigen. In some embodiments, the antigen of interest comprises an inactivated virus. In a specific embodiment, the inactivated virus is influenza virus. In specific embodiments, the antigen of interest is a trivalent or quadravalent inactivated influenza virus composition. In specific embodiments, the antigen of interest comprises a split influenza virus. In specific embodiments, the antigen of interest is an infectious disease antigen. In certain embodiments, the antigen of interest is a RSV antigen, human Metapneumovirus antigen, MERS-CoV antigen, Lassa virus antigen, Japanese encephalitis antigen, or hepatitis A virus antigen. In some embodiments, the antigen of interest is a *Clostridium tetani* antigen, *Bacillus* antigen, *Bordetella pertussis* antigen, *Streptococcus pneumoniae* antigen, *Neisseria meningitides* antigen, *Haemophilus influenzae* antigen, or *Corynebacterium* diphtherias antigen. In certain embodiments, the *Bacillus* antigen is a *Bacillus anthracis* antigen. In some embodiments, the antigen of interest is a cancer antigen. In certain embodiments, the immunogenic composition is administered subcutaneously or intramuscularly.

In another aspect, provided herein is a method for immunizing a subject against a disease or disorder caused by or associated with an antigen, comprising administering an immunogenic composition described herein. In a specific embodiment, provided herein is a method for immunizing a subject against COVID-19, comprising administering to the subject an immunogenic composition comprising a SARS-CoV-2 antigen and a compound described herein. In another specific embodiment, provided herein is a method for immunizing a subject against influenza virus disease, comprising administering to the subject an immunogenic composition comprising an influenza virus antigen and a compound described herein. In a specific embodiment, the subject is human.

In another aspect, provided herein is a method for preventing a disease or disorder caused by or associated with an antigen in a subject, comprising administering an immunogenic composition described herein. In a specific embodiment, provided herein is a method for preventing COVID-19 in a subject, comprising administering to the subject an immunogenic composition comprising a SARS-CoV-2 antigen and a compound described herein. In another specific embodiment, provided herein is a method for preventing influenza virus disease in a subject, comprising administering to the subject an immunogenic composition comprising an influenza virus antigen and a compound described herein. In a specific embodiment, the subject is human. In certain embodiments, the immunogenic composition is administered subcutaneously or intramuscularly.

In another aspect, provided herein is a method of inducing an immune response to an antigen of interest in a subject, comprising administering to the subject a pharmaceutical composition comprising a compound described herein, and an immunogenic composition comprising an antigen of interest. In some embodiment, the pharmaceutical composition and the immunogenic composition are administered to the subject concurrently. In certain embodiments, the pharmaceutical composition is administered to the subject prior to the administration of the immunogenic composition. In some embodiments, the pharmaceutical composition is administered to the subject after the administration of the immunogenic composition. In certain embodiments, the pharmaceutical composition and immunogenic composition are administered to the subject by the same route of administration (e.g., subcutaneous or intramuscular). In some embodiments, the pharmaceutical composition and the immunogenic composition are administered to the subject by different routes of administration. In certain embodiments, the pharmaceutical composition and the immunogenic composition are administered to the same region of the subject.

In another aspect, provided herein is a method of immunizing a subject against a disease or disorder caused by or associated with an antigen, comprising administering to the subject a pharmaceutical composition described herein, and an immunogenic composition comprising an antigen of interest. In a specific embodiment, provided herein is a method of immunizing a subject against COVID-19, comprising administering to the subject a pharmaceutical composition comprising a compound described herein, and an immunogenic composition comprising a SARS-CoV-2 antigen. In another specific embodiment, provided herein is a method of immunizing a subject against influenza virus disease, comprising administering to the subject a pharmaceutical composition comprising a compound described herein, and an immunogenic composition comprising an influenza virus antigen. In some embodiment, the pharmaceutical composition and the immunogenic composition are administered to the subject concurrently. In certain embodiments, the pharmaceutical composition is administered to the subject prior to the administration of the immunogenic composition. In some embodiments, the pharmaceutical composition is administered to the subject after the administration of the immunogenic composition. In certain embodiments, the pharmaceutical composition and immunogenic composition are administered to the subject by the same route of administration (e.g., subcutaneous or intramuscular). In some embodiments, the pharmaceutical composition and the immunogenic composition are administered to the subject by different routes of administration. In certain embodiments, the pharmaceutical composition and the immunogenic composition are administered to the same region of the subject.

In another aspect, provided herein is a method of preventing a disease or disorder caused by or associated with an antigen in a subject, comprising administering to the subject a pharmaceutical composition a compound described herein, and an immunogenic composition comprising an antigen of interest. In a specific embodiment, provided herein is a method of preventing COVID-19 in a subject, comprising administering to the subject a pharmaceutical composition comprising a compound described herein, and an immunogenic composition comprising a SARS-CoV-2 antigen. In another specific embodiment, provided herein is a method of preventing influenza virus disease in a subject, comprising administering to the subject a pharmaceutical composition comprising a compound described herein, and an immunogenic composition comprising an influenza virus antigen. In some embodiment, the pharmaceutical composition and the immunogenic composition are administered to the subject concurrently. In certain embodiments, the pharmaceutical composition is administered to the subject prior to the administration of the immunogenic composition. In some embodiments, the pharmaceutical composition is administered to the subject after the administration of the immunogenic composition. In certain embodiments, the pharmaceutical composition and immunogenic composition are administered to the subject by the same route of administration (e.g., subcutaneous or intramuscular). In some embodiments, the pharmaceutical composition and the immunogenic composition are administered to the subject by different routes of administration. In certain embodiments, the pharmaceutical composition and the immunogenic composition are administered to the same region of the subject.

In another aspect, provided herein is a method for enhancing the immune response to an antigen of interest in a subject, comprising administering to the subject a compound described herein in an immunogenic composition comprising the antigen of interest. In specific embodiments, provided herein is a method for enhancing the immune response to an antigen of interest in a subject, comprising administering to the subject an immunogenic composition described herein. In certain embodiments, the immune response to the antigen of interest is at least 10%, at least 25%, at least 30%, at least 40% or at least 50% higher than the immune response to the antigen of interest without the administration of the pharmaceutical composition. In one embodiment, the immune response is a humoral immune response. In another embodiment, the immune response is a cellular immune response. In another embodiment, the immune response is a humoral and a cellular immune response. In a specific embodiment, the subject is human.

In another aspect, provided herein is a method for enhancing the immune response to an antigen of interest in a subject, comprising administering to the subject a pharmaceutical composition comprising a compound described herein, and an immunogenic composition comprising the antigen of interest. In certain embodiments, the pharmaceutical composition and the immunogenic composition are administered to the subject concurrently. In some embodiments, the pharmaceutical composition is administered to the subject prior to the administration of the immunogenic composition. In certain embodiments, the pharmaceutical composition is administered to the subject after the administration of the immunogenic composition. In some embodiments, the pharmaceutical composition and immunogenic composition are administered to the subject by the same route of administration (e.g., subcutaneous or intramuscular). In certain embodiments, the pharmaceutical composition and the immunogenic composition are administered to the subject by different routes of administration. In some embodiments, the pharmaceutical composition and the immunogenic composition are administered to the same region of the subject. In certain embodiments, the immune response to the antigen of interest is at least 10%, at least 25%, at least 30%, at least 40% or at least 50% higher than the immune response to the antigen of interest without the administration of the pharmaceutical composition. In one embodiment, the immune response is a humoral immune response. In another embodiment, the immune response is a cellular immune response. In another embodiment, the immune response is a humoral and a cellular immune response. In a specific embodiment, the subject is human.

In another aspect, a compound described is for use in the preparation of a medicament for use inducing an immune response to an antigen of interest in a subject. In a specific embodiment, a compound described herein is for use in the preparation of a medicament for use in enhancing an immune response to an antigen of interest in a subject.

In another aspect, a pharmaceutical composition a compound described herein is for use in a method for inducing an immune response to an antigen of interest in a subject comprising administrating an immunogenic composition comprising the antigen of interest to the subject. In a specific embodiment, a pharmaceutical composition comprising a compound described herein is for use in a method for enhancing an immune response to an immunogenic composition comprising an antigen of interest in a subject. In a specific embodiment, the subject is a human subject.

In another aspect, an immunogenic composition described herein is for use in a method for inducing an immune response to the antigen of interest in a subject. In a specific embodiment, the subject is a human subject.

In certain embodiments, the antigen of interest is a SARS-CoV-2 antigen. In a specific embodiment, the SARS-CoV-2 antigen comprises a SARS-CoV-2 spike protein ectodomain with amino acid substitutions of RRAR to A at amino acid residues corresponding to amino acid residues 682 to 685 of GenBank Accession No. MN908947.3, and amino acid substitutions to prolines at amino acid residues corresponding to amino acid residues 986 and 987 of GenBank Accession No. MN908947.3. The ectodomain may be directly or indirectly linked to a trimerization domain. In a specific embodiment, the trimerization domain is a T4 foldon trimerization domain. In certain embodiments, the SARS-CoV2 antigen comprises a tag. The trimerization domain may be directly or indirectly linked to a tag. In some embodiments, the tag is a hexa-histidine tag or flag tag. In some embodiments, the antigen of interest is an infectious disease antigen. In certain embodiments, the antigen of interest is a viral antigen, a bacteria antigen, a fungal antigen, or a parasitic antigen. In some embodiments, the antigen of interest comprises an inactivated virus. In a specific embodiment, the inactivated virus is influenza virus. In specific embodiments, the antigen of interest is a trivalent or quadravalent inactivated influenza virus composition. In specific embodiments, the antigen of interest comprises a split influenza virus. In specific embodiments, the antigen of interest is an infectious disease antigen. In certain embodiments, the antigen of interest is a RSV antigen, human Metapneumovirus antigen, MERS-CoV antigen, Lassa virus antigen, Japanese encephalitis antigen, or hepatitis A virus antigen. In some embodiments, the antigen of interest is a *Clostridium tetani* antigen, *Bacillus* antigen, *Bordetella pertussis* antigen, *Streptococcus pneumoniae* antigen, *Neisseria meningitides* antigen, *Haemophilus influenzae* antigen, or *Corynebacterium* diphtherias antigen. In certain embodiments, the *Bacillus* antigen is a *Bacillus anthracis* antigen. In some embodiments, the antigen of interest is a cancer antigen.

In another aspect, provided herein are kits comprising a compound described herein. See, Section 5.7, infra, for a description of kits.

4. BRIEF DESCRIPTION OF THE FIGURES

Figure 1B:
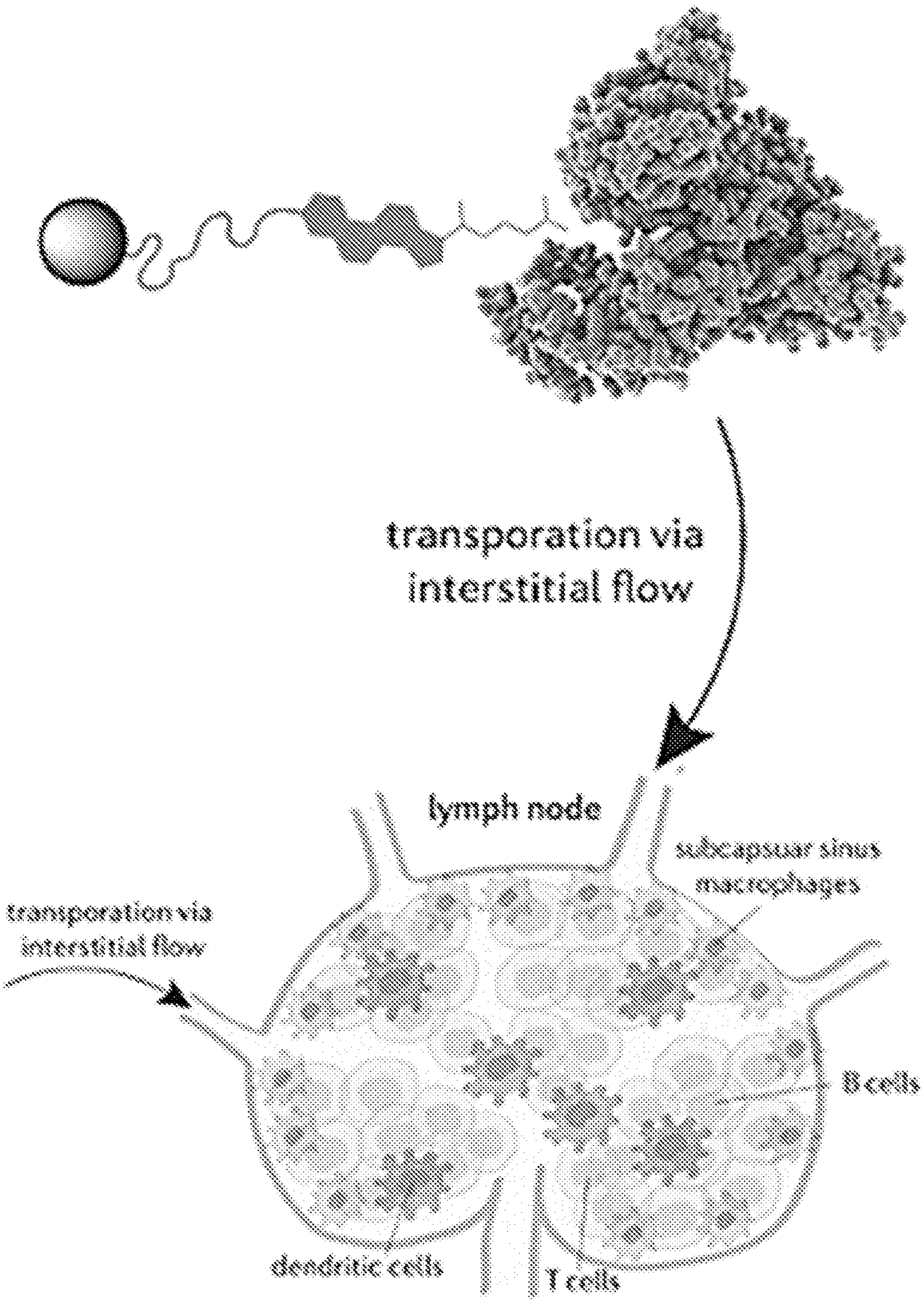

FIGS. 1A-1B. (FIG. 1A) Molecular structure of (A1) CHOL-PEG-IMDQ and (A2) PEG-IMDQ. Conjugation was performed by amide bond formation between respectively cholesterylamine and PEG and PEG and IMDQ. (FIG. 1B) Schematic representation of albumin hitchhiking-mediated lymphatic transportation.

FIGS. 2A-2E. (FIG. 2A) Biolayer interferometry (BLI) sensorgrams of non-amphiphilic IMDQ-PEG and amphiphilic IMDQ-CHOL-PEG binding to albumin-coated sensors. A dilution series of 50, 10 and 5 mg/mL (dark to light color code, as marked by the black arrow) was measured. Sensors were dipped into a PEG- or lipid-PEG solution at the 500 s time point, which marks the onset of adsorption. At the 1125 s time point, sensors were dipped into PBS, which marks the onset of desorption. (FIG. 2B) Flow cytometry analysis of association between DC2.4 cells and Cyanine5-PEG, Cyanine5-PEG-CHOL, respectively. (n=3; Student t-test, **: $p<0.0001$, *: $p<0.001$). The bars in the bar graph are in the following order: PBS, Cyanine5-PEG, and Cyanine5-PEG-CHOL. (FIG. 2C) Confocal microscopy images of DC2.4 cells incubated for 24 h at 37 C with Cyanine5-PEG and Cyanine5-PEG-CHOL. Left panel represents the Cyanine5 channel, right panel represents the overlay of the Cyanine5 and transmitted light channels. Scale bar represents 15 micron. (FIG. 2D) TLR agonistic activity of IMDQ-PEG-CHOL, IMDQ-PEG and native IMDQ measured as NF-κB activation using the RAW-Blue reporter cell assay. (n=6, mean+sd). (FIG. 2E) Cytotoxicity of IMDQ-PEG-CHOL, IMDQ-IMDQ and native IMDQ, measured by MTT assay (n=6, mean+sd).

Figure 2B:
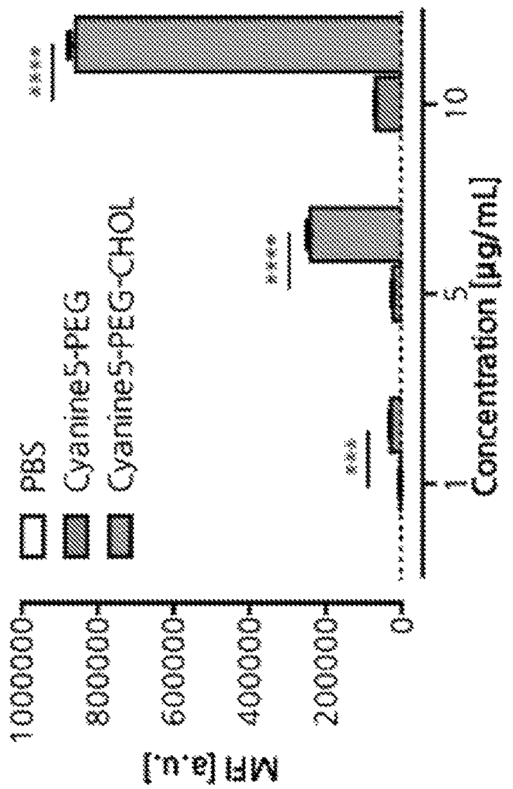
Figure 2A:
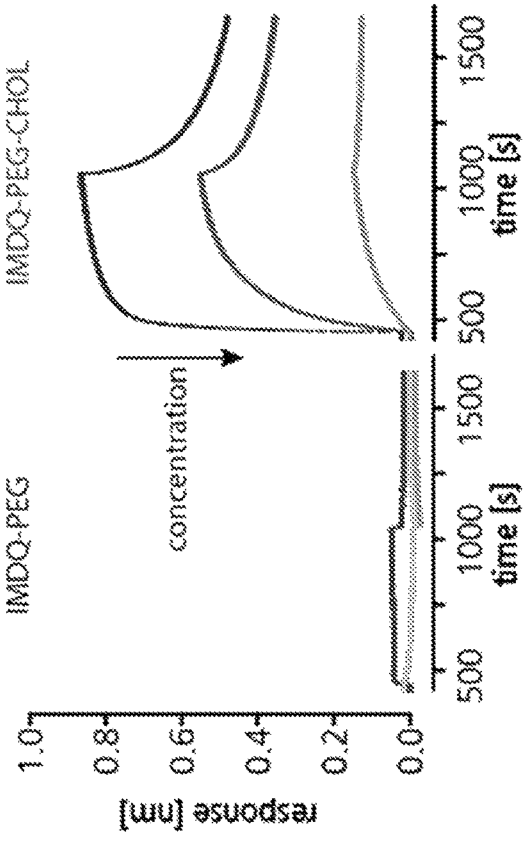
Figure 2C:
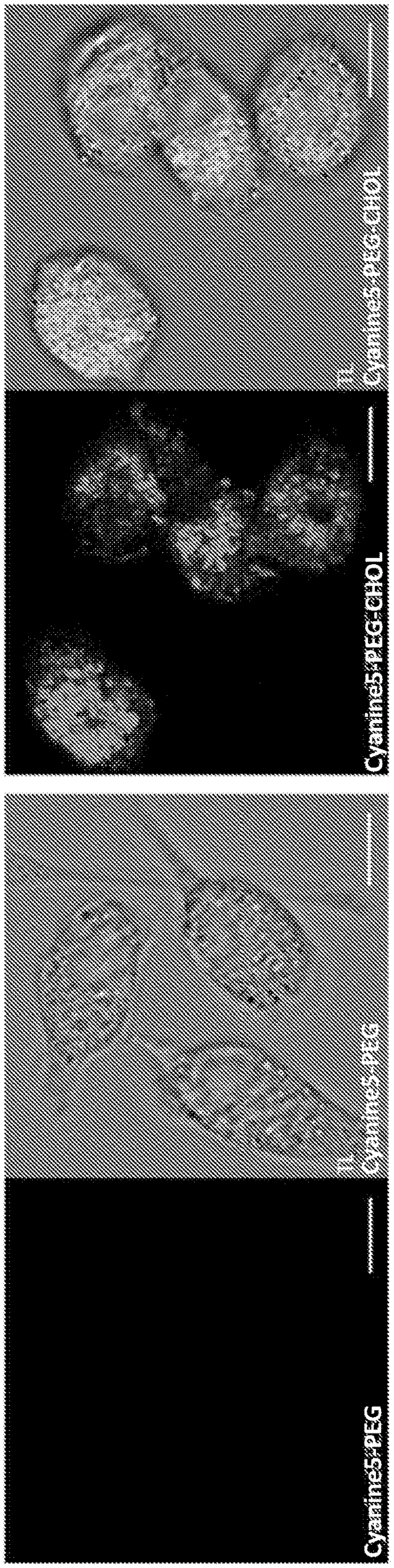
Figure 2D:
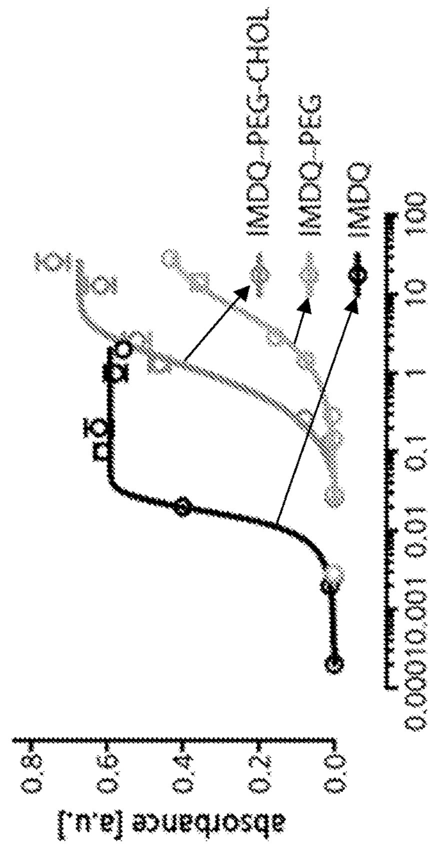
Figure 2E:
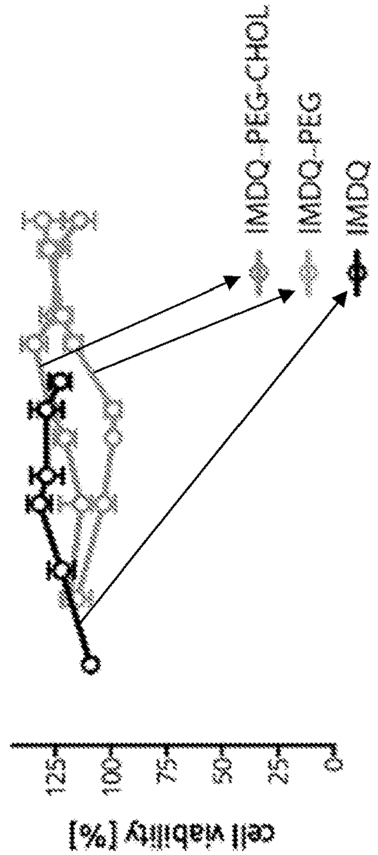
Figure 3A:
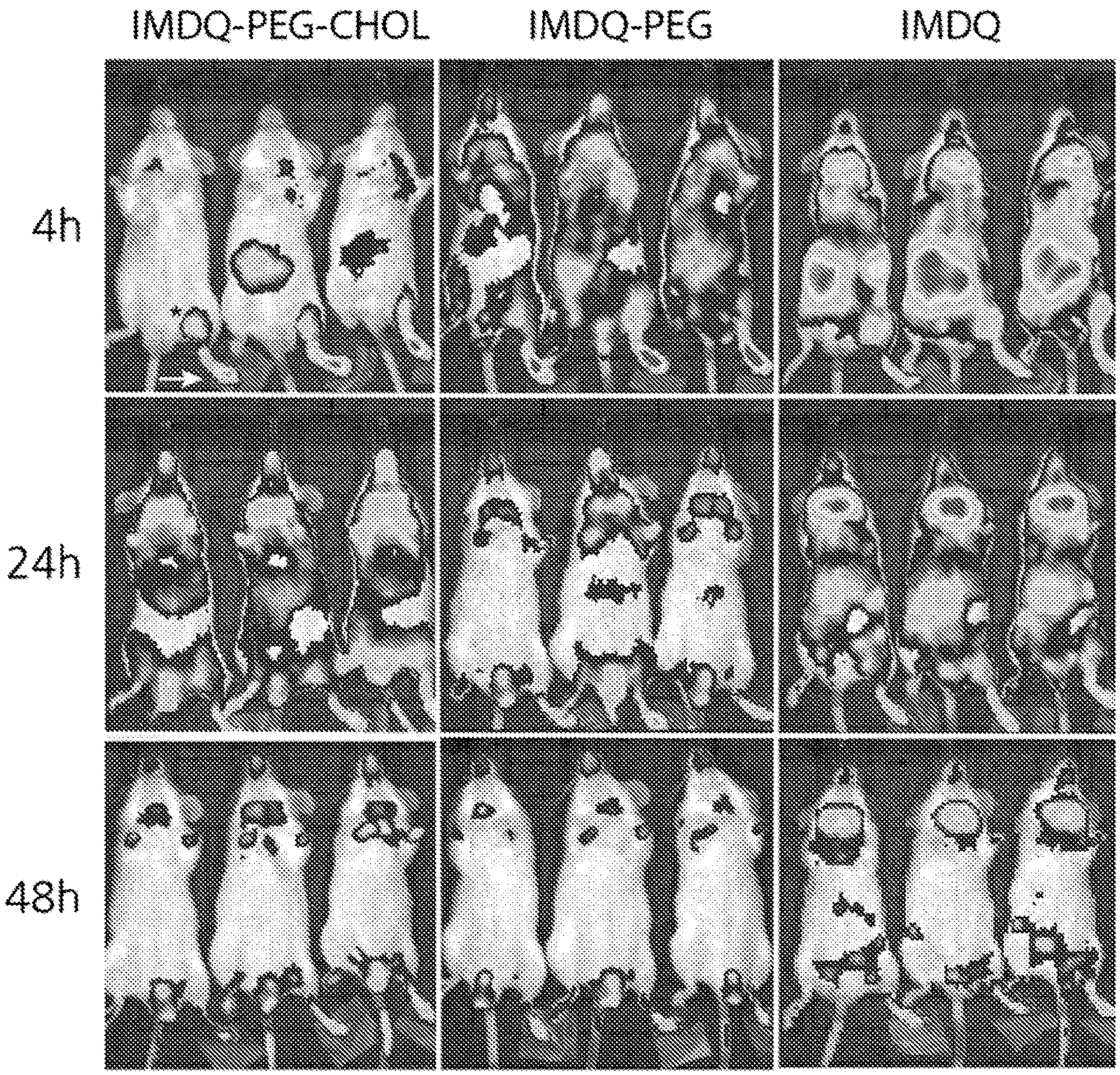

FIGS. 3A-3D2. (FIG. 3A) Bioluminescence images of luciferase reporter mice (IFβ+/Δβ-luc); images taken 4, 24 and 48 h post footpad injection of IMDQ-PEG-CHOL, IMDQ-PEG and native IMDQ. (FIG. 3B1) Confocal microscopy images of lymph node tissue sections 48 h post subcutaneous injection of Cyanine5-PEG-CHOL, respectively Cyanine5-PEG, into the footpad of mice. Scale bar represents 100 micron. (FIG. 3B2) Flow cytometry analysis of the draining popliteal lymph node 48 h post subcutaneous injection of Cyanine5-PEG-CHOL, respectively Cyanine5-PEG into the footpad of mice. (n=3, mean+sd; Student's t-test: **: p<0.0001) (FIG. 3C) Translocation of Cyanine5-PEG-CHOL to the draining popliteal lymph node analyzed 24 h post injection into the footpad, measured by flow cytometry. (n=6, mean+sd) (FIGS. 3D1 and 3D2) Flow cytometry analysis of the innate immune response in the draining popliteal lymph node 24 h post injection of IMDQ-PEG-CHOL into the footpad (FIG. 3D1) Relative increase in innate immune cell subset and T cell numbers relative to a naïve control and (FIG. 3D2) maturation/activation of innate immune cell subsets and T cells (n=6, mean+sd; Student's t-test: **: p<0.0001).

FIGS. 4A-4E. IMDQ-PEG-CHOL induces a balanced neutralizing antibody response to IVR-180 [Influenza A/Singapore/gp1908/2015 (H1N1)] infection. (FIG. 4A) Outline of the QIV immunization and influenza virus challenge study. (FIG. 4B) Vaccine-specific ELISA titers for total IgG, IgG1 and IgG2a and IgG2a/IgG1 ratio (based on the AUC (OD at 450 nm) curve of the individual serum samples) in mice sera collected 3 weeks post-vaccination. (FIG. 4C) Control versus immunized sera analyzed for HI titers by hemagglutination inhibition assay, using 100LD50 (18000 PFU) of IVR-180 virus. The outcome is represented as IC50 values. (FIG. 4D) Body weight loss of mice reported as percentage of initial body weight after challenge with 100LD50 (18000 PFU) of IVR-180 virus. (FIG. 4E) Viral lung titers after challenge with 100LD50 (18000 PFU) of IVR-180 virus. Data are represented as plaque-forming-unit (PFU)/mL (geometric mean with geometric SD). Lungs were harvested on day-5 post infection with IVR-180 virus.

FIGS. 5A-5D. IMDQ-PEG-CHOL induces a balanced neutralizing antibody response to SARS-CoV-2 infection. (FIG. 5A) Outline of the Spike protein vaccination and SARS-CoV-2 challenge. (FIG. 5B) ELISA titers for total IgG, IgG1 and IgG2a and IgG2a/IgG1 ratio (based on the AUC (OD at 450 nm) curve of the individual serum samples) in mice sera collected 3 weeks post-vaccination. (FIGS. 5C1-5C2) Control versus vaccinated sera examined for presence of virus-neutralizing antibodies by microneutralization assay, using 100TCID50 of SARS-CoV-2 virus. The outcome is represented as a percentage inhibition of viral growth in (5C1) and as IC50 calculated by a non-linear regression analysis of percentage inhibition curve in (5C2). (FIG. 5D) Viral lung titers represented as Plaque-forming-unit (PFU)/mL (geometric mean with geometric SD). The Ad5-hACE2 transduced mice were challenged with $5*10^4$ PFU of SARS-CoV-2 and the lungs were harvested on day-4 post infection.

Figure 6B:
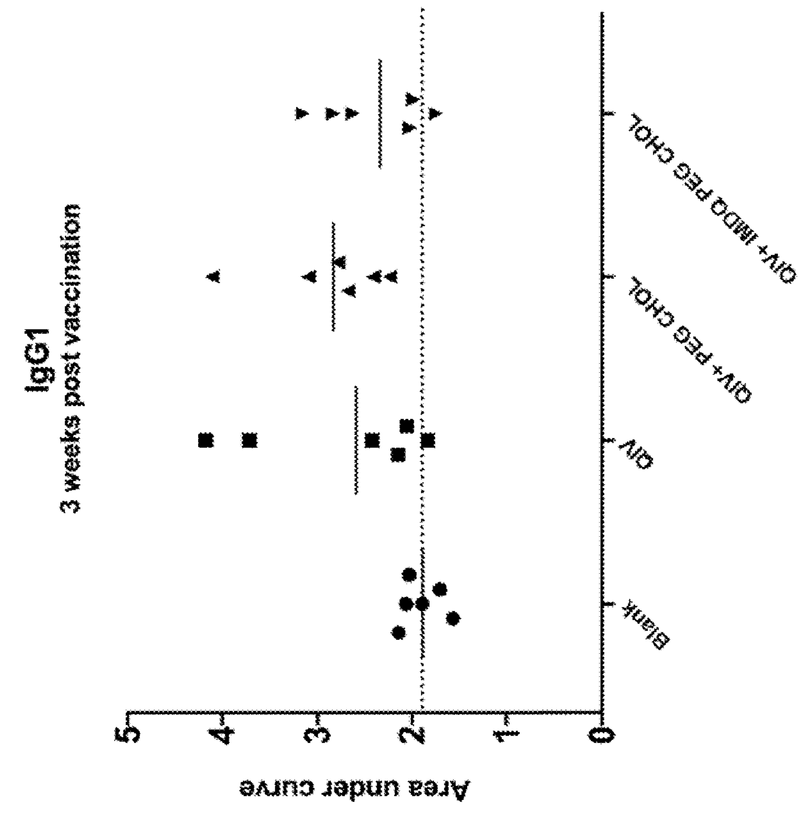
Figure 6A:
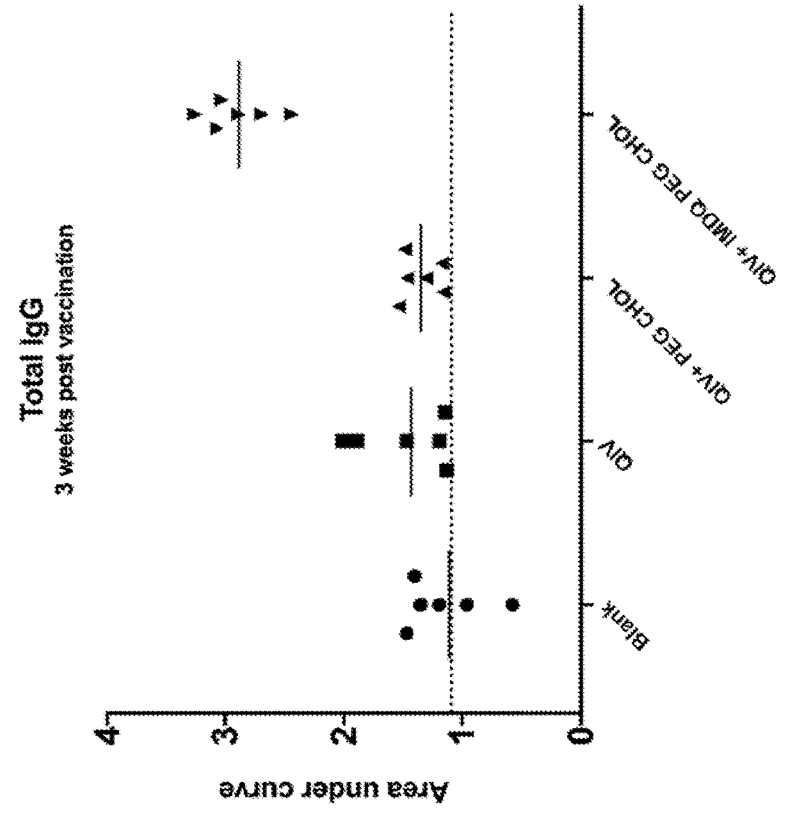
Figure 6C:
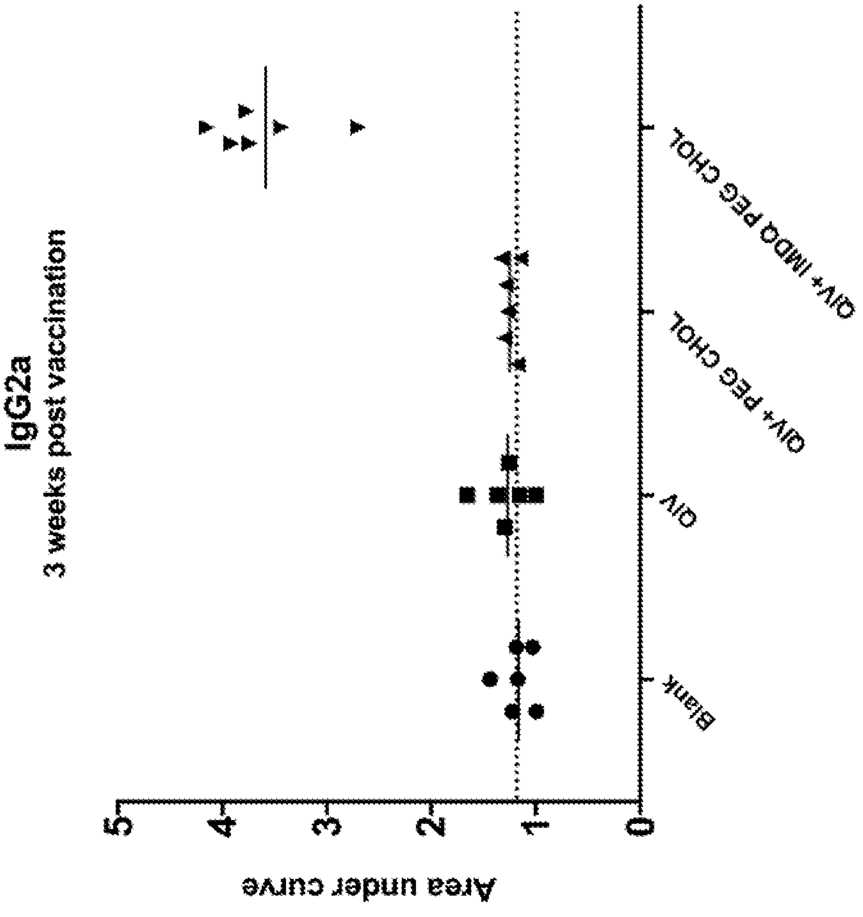

FIGS. 6A-6C. ELISA titers for total IgG (FIG. 6A), IgG1 (FIG. 6B), and IgG2a (FIG. 6C) in mice sera collected 3 weeks post-vaccination. The ratio IgG2a/IgG1 is representative of the Area under the OD450 curve of the individual serum sample.

Figure 7A:
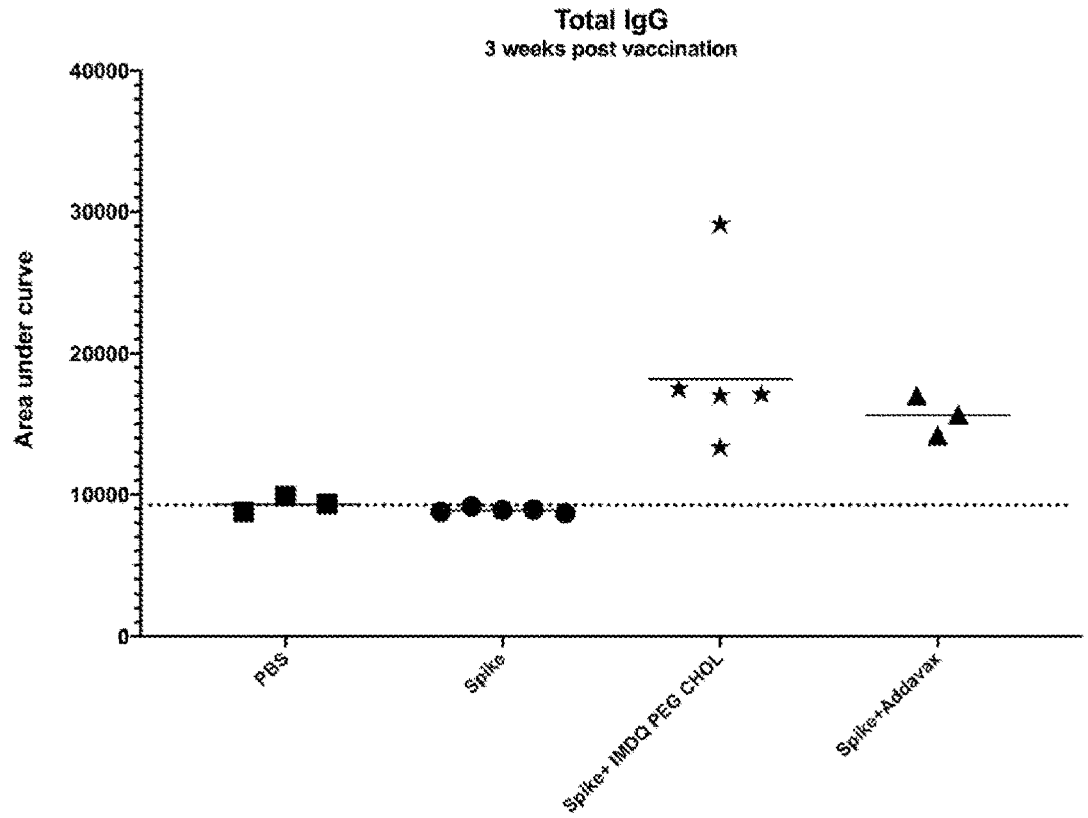
Figure 7B:
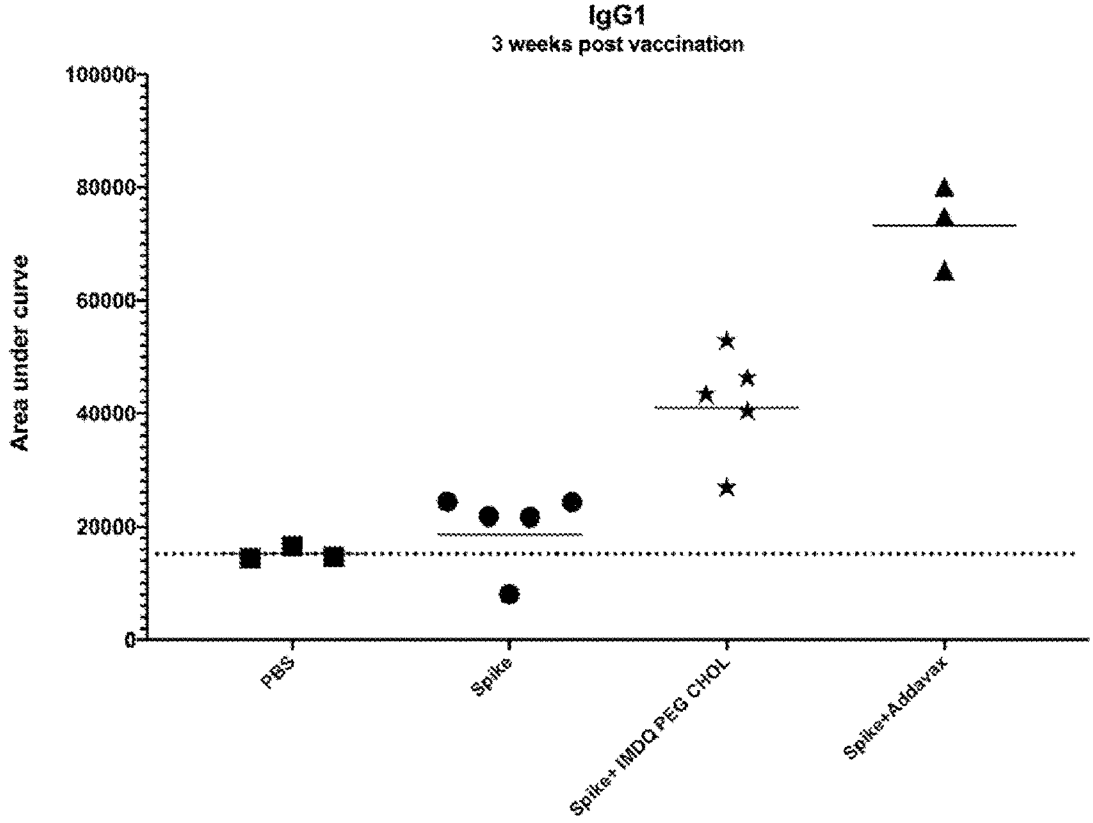
Figure 7C:
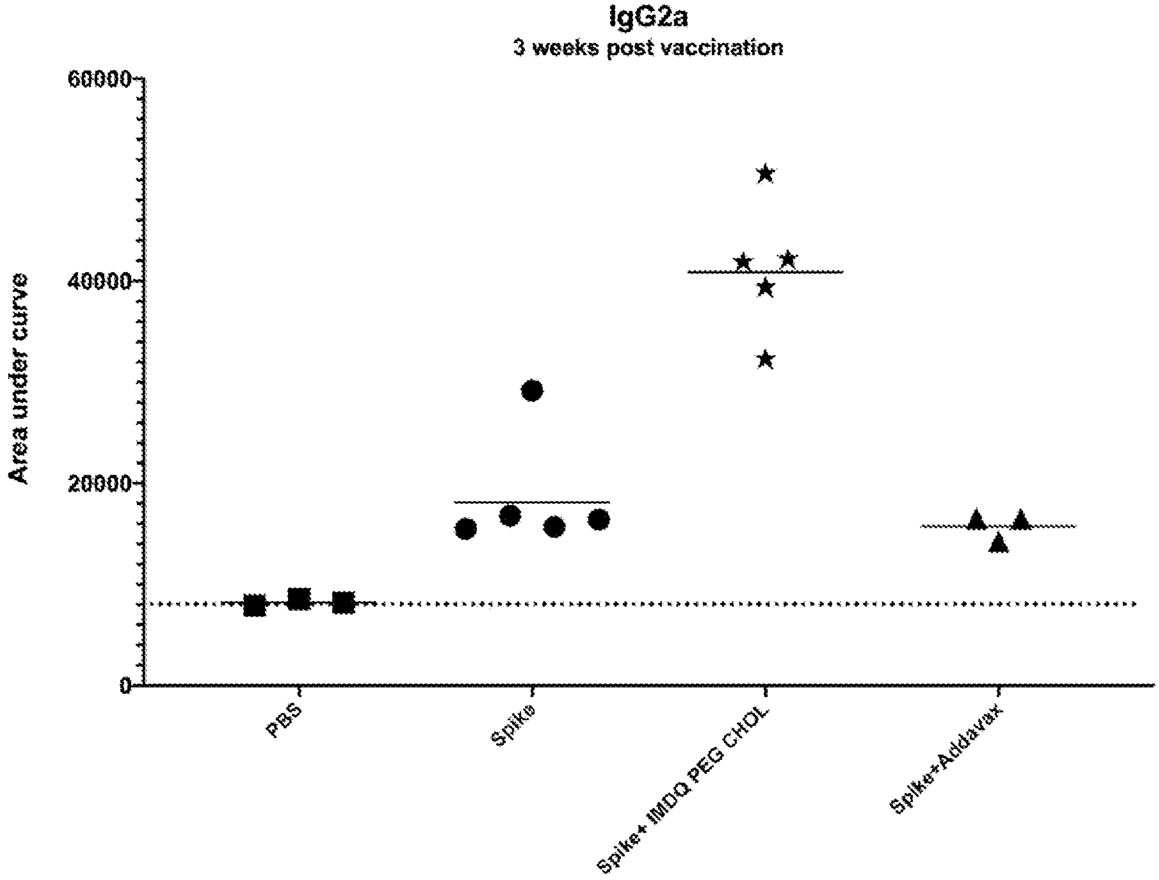

FIGS. 7A-7C. ELISA titers for total IgG (FIG. 7A), IgG1 (FIG. 7B), and IgG2a (FIG. 7C) in mice sera collected 3 weeks post-vaccination. The ratio IgG2a/IgG1 is representative of the Area under the OD450 curve of the individual serum sample.

Figure 8:
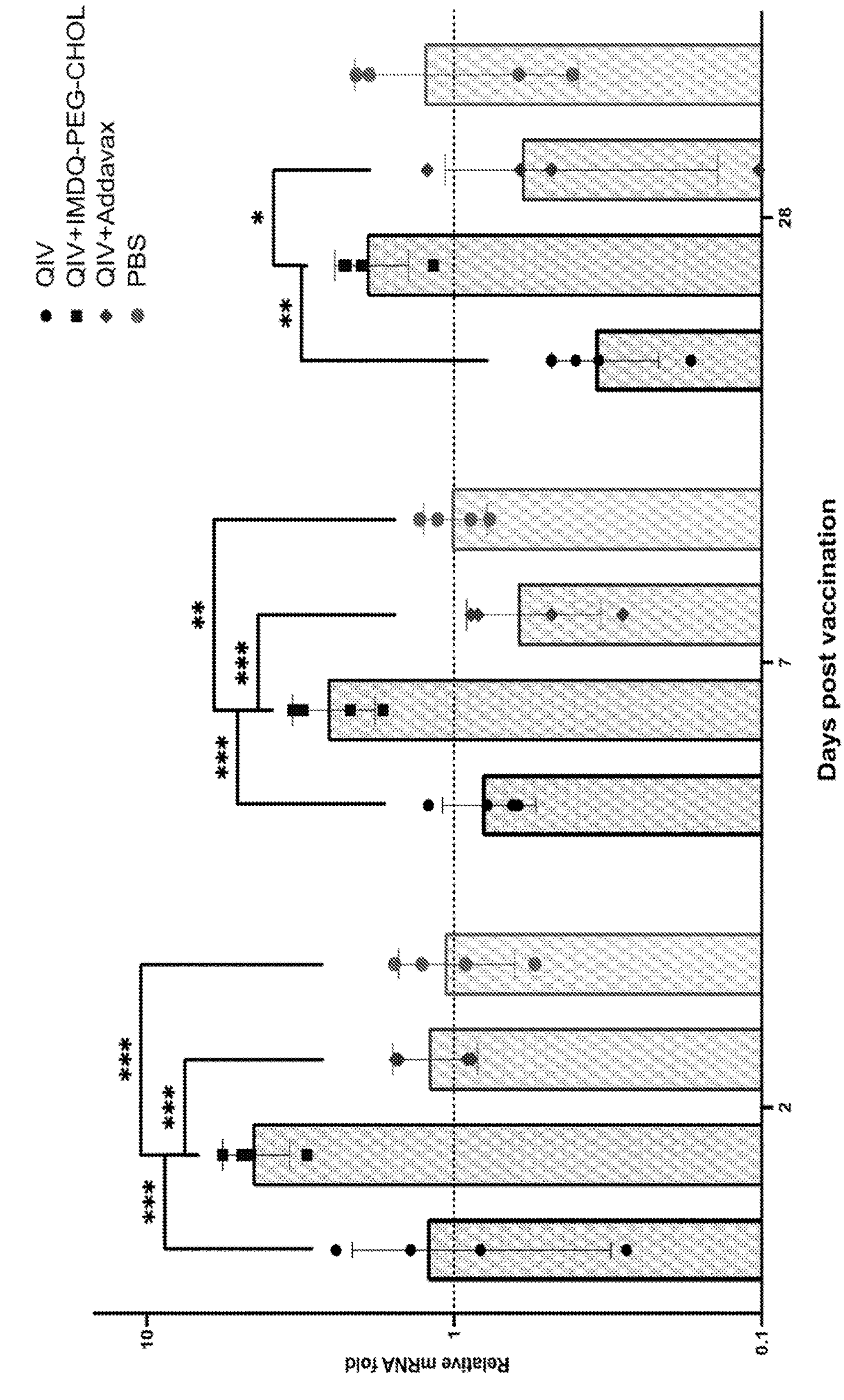

FIG. 8. ISG15 gene expression levels (relative to household gene) as measured by qPCR in blood of vaccinated BALB/c mice at different time points post vaccination. Mice received 1.5 μg of HA equivalent in 50 ?al via the intramuscular route either unadjuvanted, adjuvanted with 10 μg of core IMDQ or mixed at equal volumes with AddaVax. Statistical differences are calculated with one way ANOVA followed by a Tukey HSD post test for multiple comparisons for every time point (* P<0.05,  P<0.01, * P<0.001).

Figure 9A:
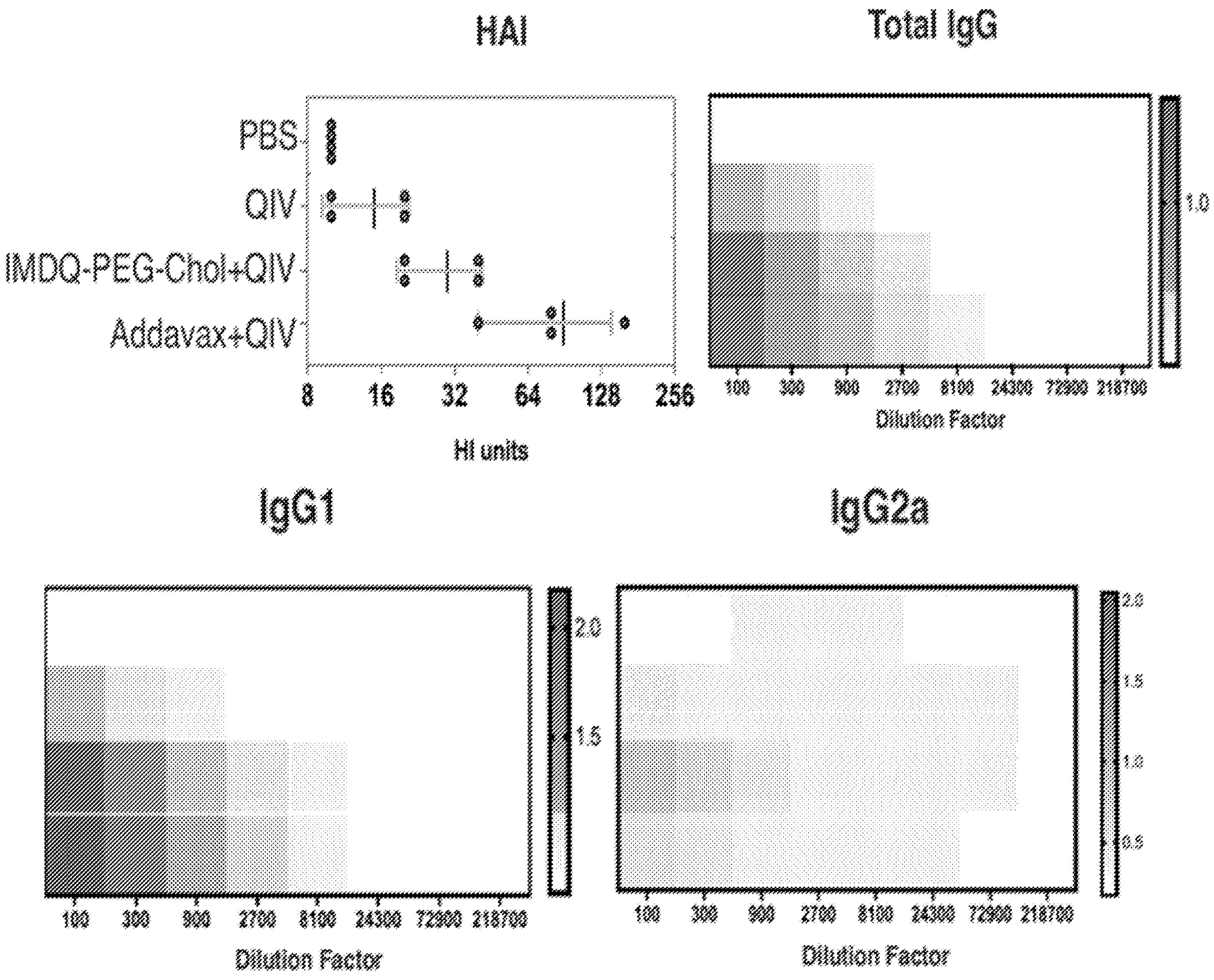
Figure 9B:
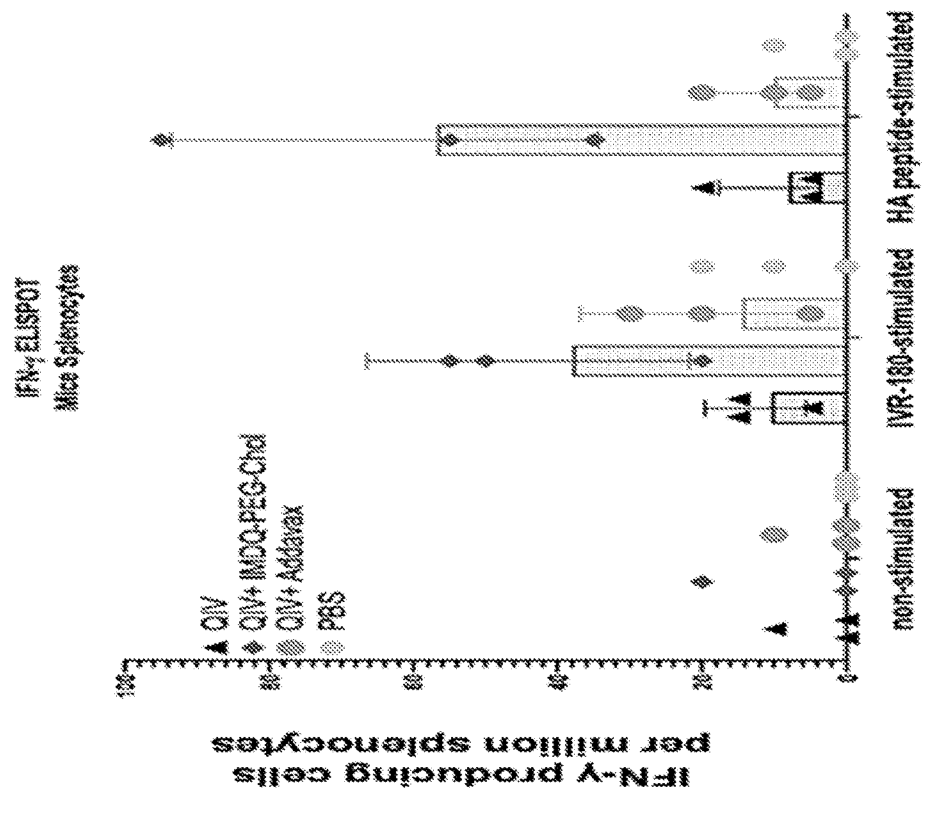
Figure 9C:
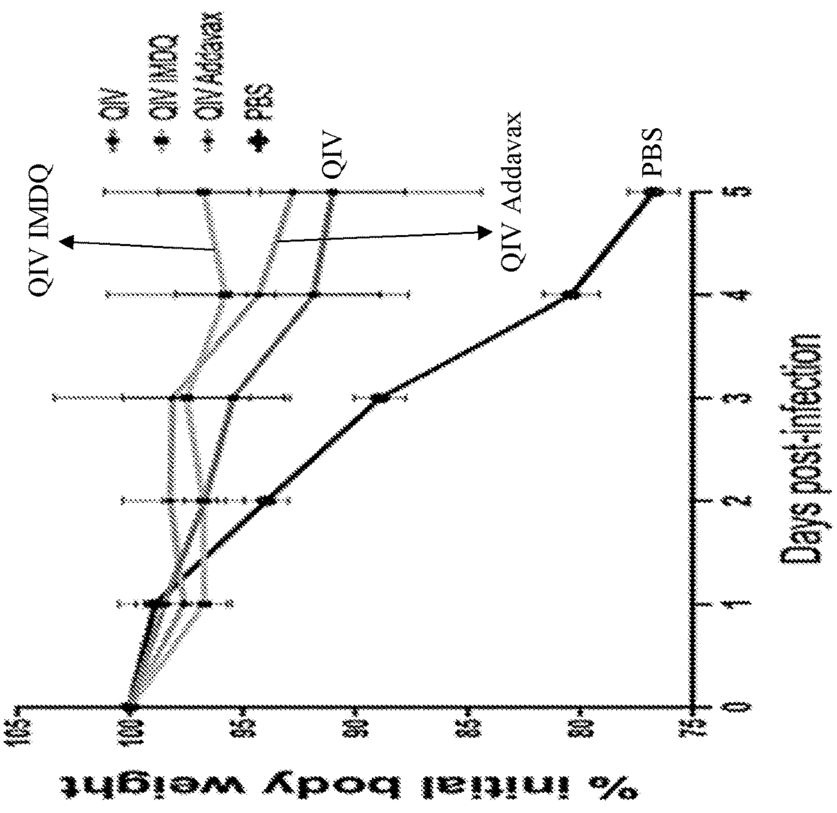
Figure 9D:
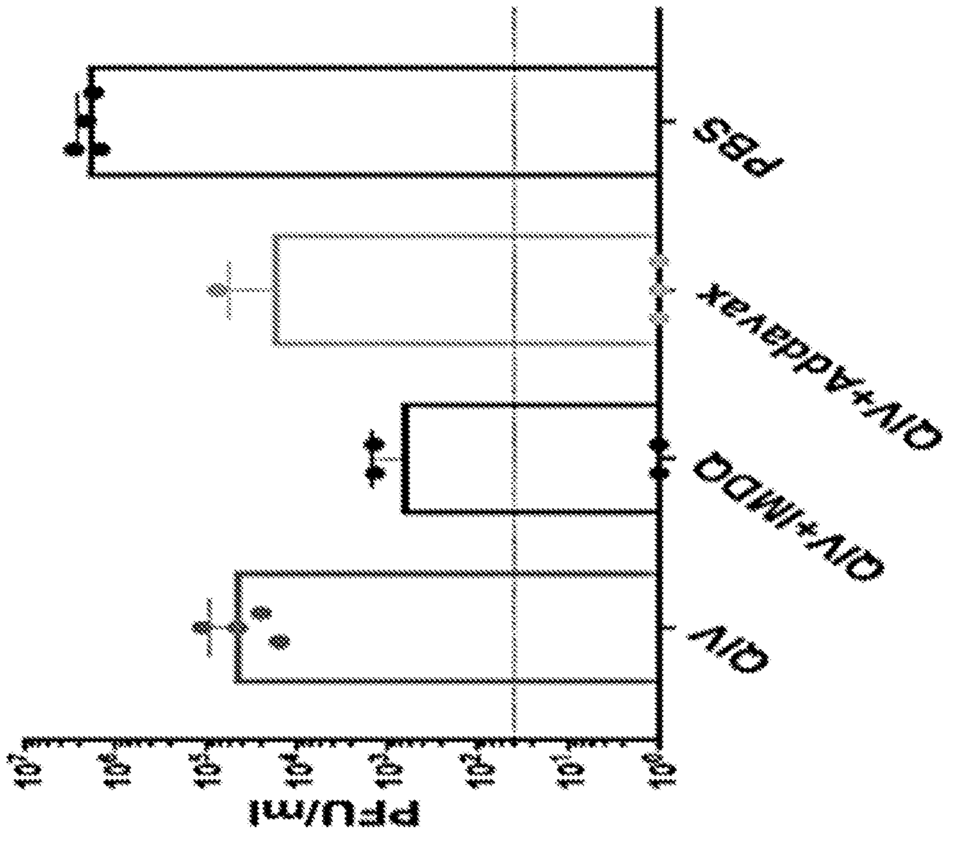

FIGS. 9A-9D. IMDQ-PEG-CHOL can potentiate humoral and cellular immune responses to vaccination. FIG. 9A. Serum hemagglutination inhibition assay and IgG ELISAs with serum collected three weeks post intramuscular vaccination with QIV (1.5 μg HA equivalent) mixed with the indicated adjuvants. FIG. 9B. IFNγ ELISPOT on splenocytes of vaccinated mice collected at 10 days post vaccination. Splenocytes were restimulated with whole IVR-180 H1N1 virus, or with peptides spanning the H1 hemagglutinin. FIG. 9C. Body weight loss after challenge with 100 LD50 of IVR-180 H1N1 virus. FIG. 9D. Lung virus titers at 5 days post infection with 100 LD50 IVR-180.

Figure 10A:
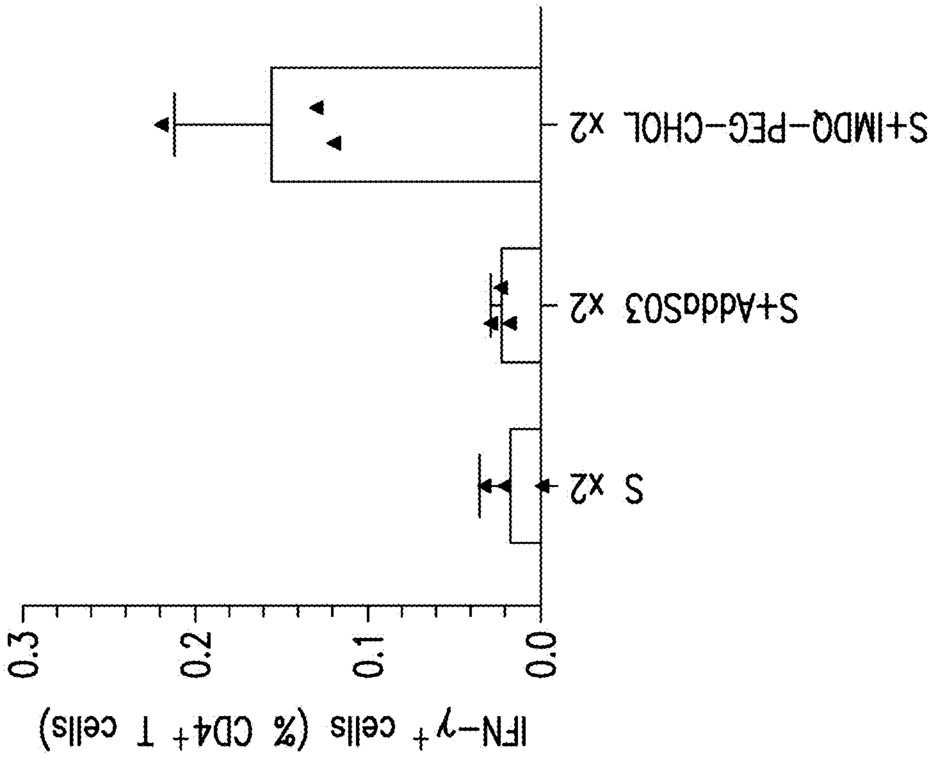
Figure 10B:
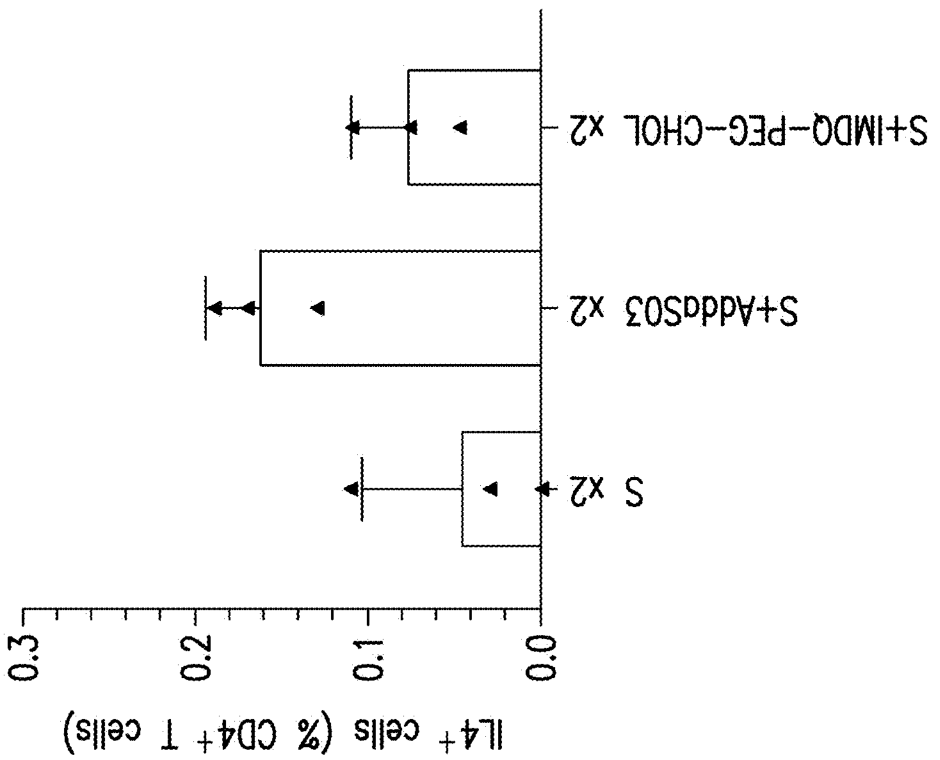

FIGS. 10A-10B. IMDQ-PEG-CHOL induces type 1 T cell responses in BALB/c mice. 129S1 mice were vaccinated twice with three weeks interval via the intramuscular route with 5 mg of recombinant trimeric SARS-CoV-2 spike protein. Splenocytes were harvested 10 days after booster vaccination and restimulated for 6 h with overlapping peptides spanning the SARS-CoV-2 spike protein in the presence of Golgiplug. FIG. 10A. IMDQ-PEG-CHOL resulted in better induction of IFNg+ CD4+ T cell responses compared to unadjuvanted control or AddaS03, and AS03-like adjuvant. FIG. 10B. Unlike AddaS03, IMDQ-PEG-CHOL did not induce IL4+ CD4+ T cell responses that exceeded unadjuvanted control, which confirms the favorable antiviral type 1 skewing potential of IMDQ-PEG-CHOL.

Figure 11A:
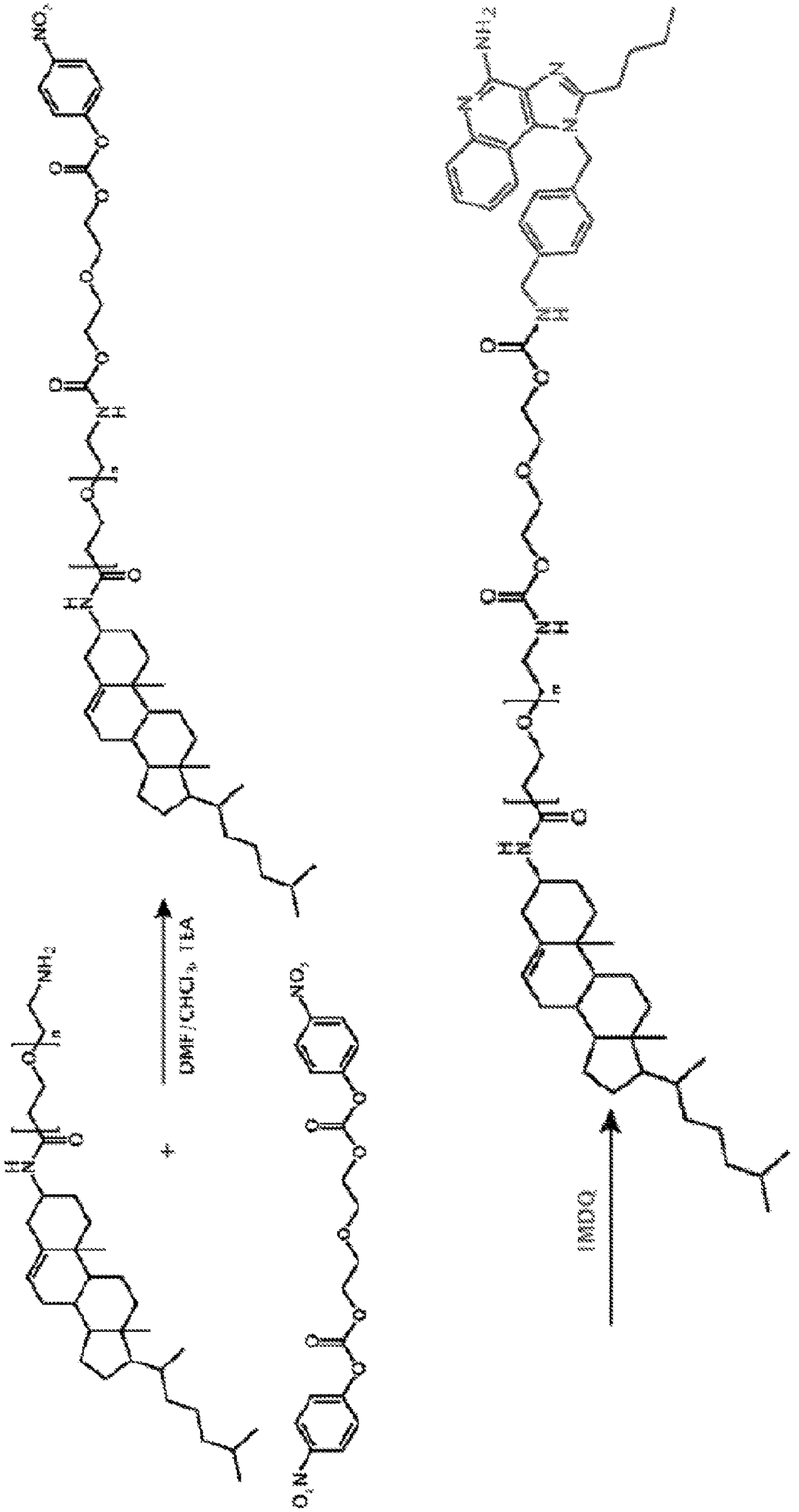
Figure 11D:
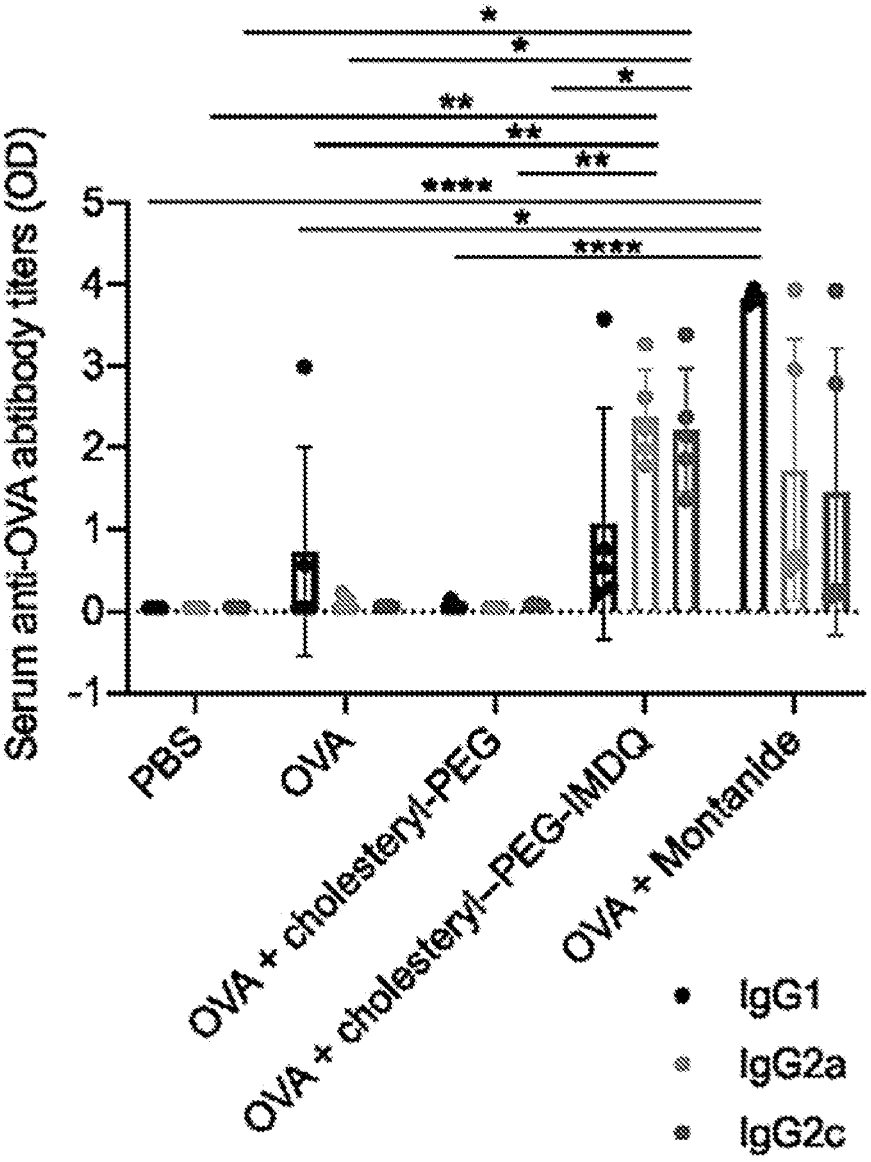

FIGS. 11A-11D. FIG. 11A) Synthesis of cholesterol-PEG-IMDQ. FIG. 11B1) Representative flow cytometry plots and FIG. 11B2) quantification of circulating antigen (OVA)-specific CD8+ T cells 7 days after primary and secondary immunizations with the indicated adjuvants. FIG. 11C1) Representative flow cytometry plots and FIG. 11C2) quantification of the phenotype of antigen (OVA)-specific CD8+ T cells in response to cholesteryl-PEG-IMDQ- and Montanide-adjuvanted OVA vaccination. FIG. 11D) Serum anti-OVA antibody titers in response to vaccination with OVA plus the indicated adjuvants. (n=5/group, mean+SD; Two-way ANOVA test: **: p<0.0001, *: p<0.001, **: p<0.01, *: p<0.05).

Figure 12:
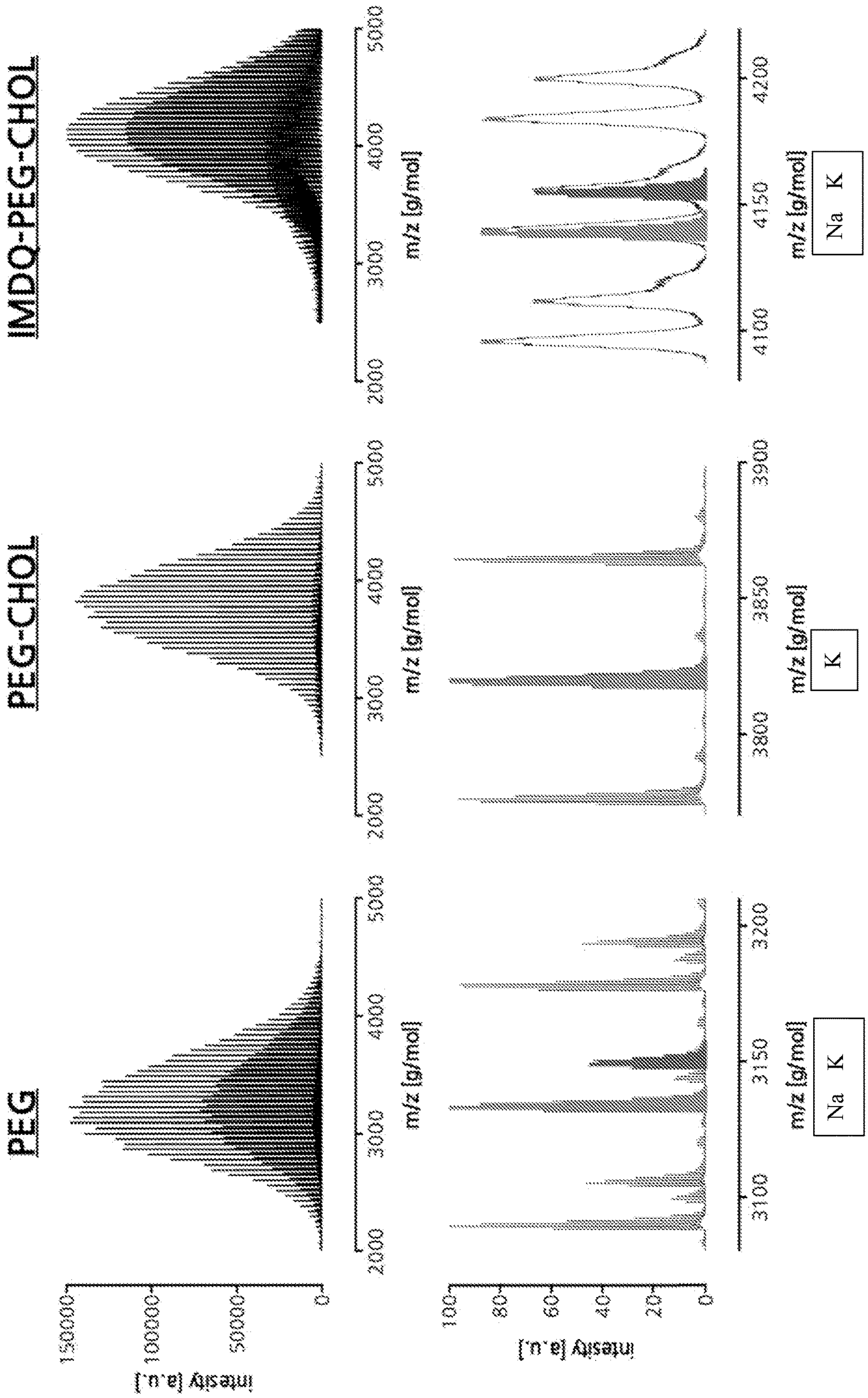

FIG. 12. MALDI-ToF analysis of PEG, PEG-Chol and IMDQ-PEG-CHOL. The bottom row depicts a zoom highlighting the simulated sodium adduct and the potassium adduct.

Figure 13:
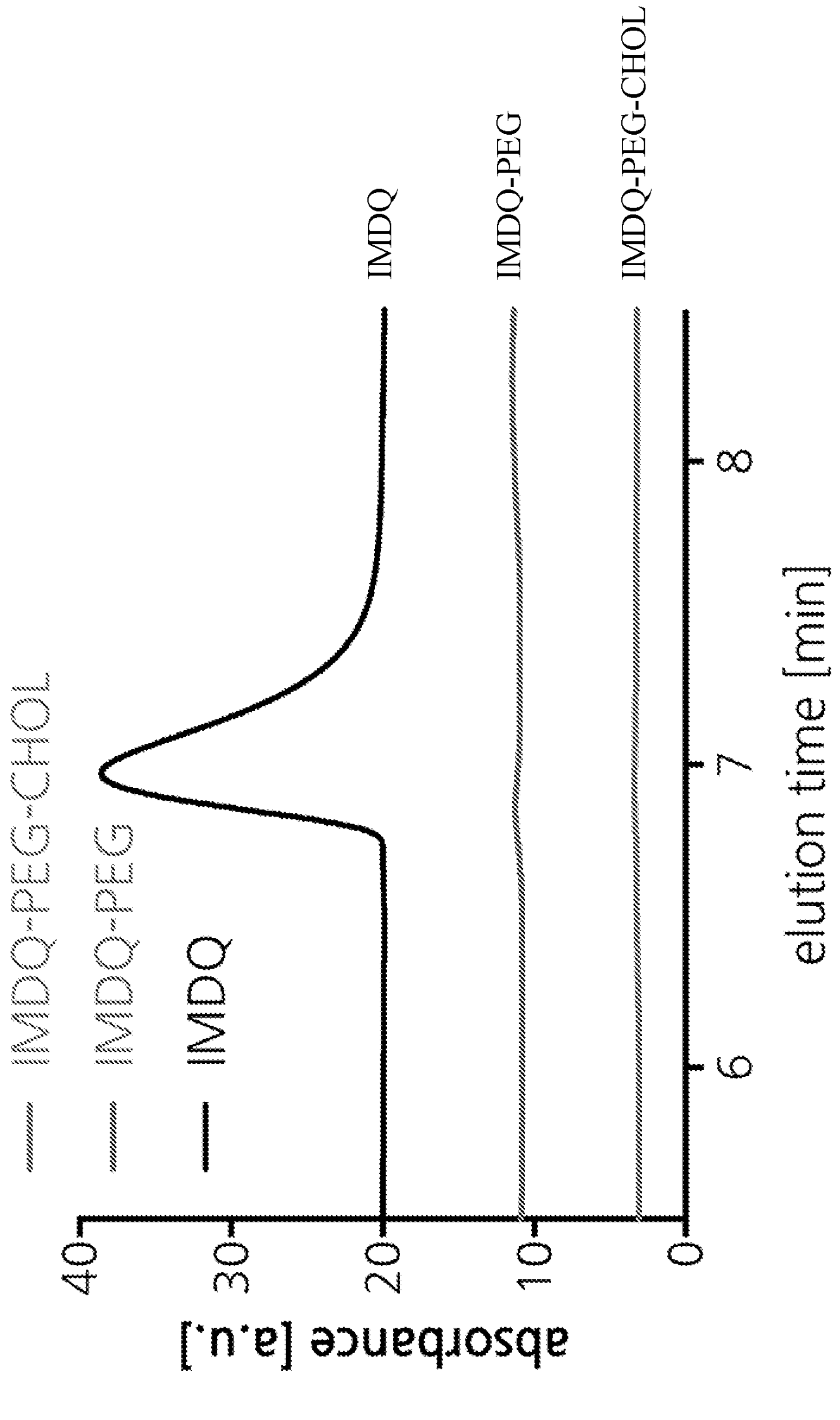

FIG. 13. HPLC elugrams (eluens 50:50acetonitrile/water with 0.1 vol % TFA) showing absence of unmodified IMDQ in IMDQ-PEG and IMDQ-PEG-CHOL as no IMDQ peak (emerging at 7 min in the IMDQ elugram) is observed in the IMDQ-PEG and IMDQ-PEG-CHOL elugrams.

5. DETAILED DESCRIPTION

5.1 IMDQ-PEG-CHOL Compounds

In one embodiment, provided herein is a compound having the following structure:

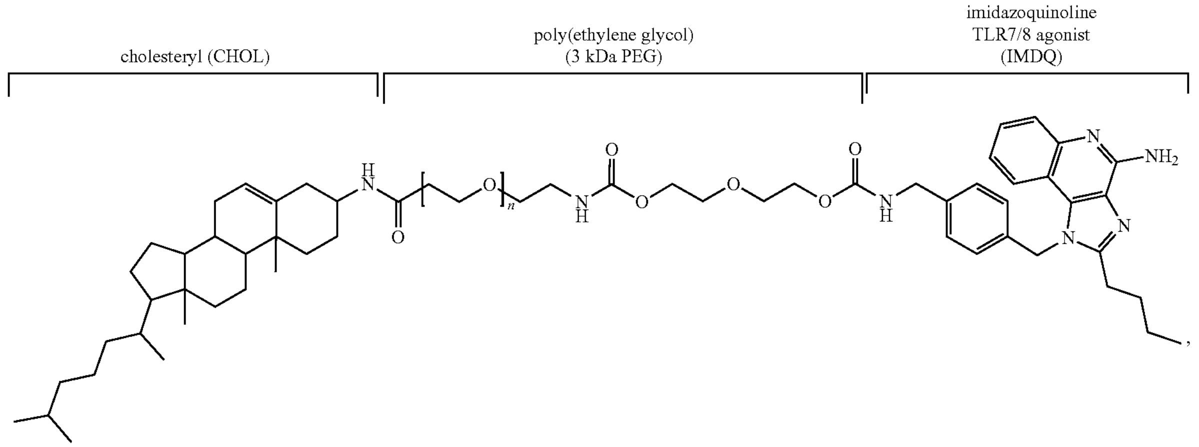

also referred to herein as IMDQ-PEG-CHOL. In one embodiment, PEG has a molecular weight of about 1 kDa to about 5 kDa. In a particular embodiment, PEG has a molecular weight of about 3 kDa. In one embodiment, n is an integer from 10 to 200. In one embodiment, n is an integer from 10 to 150. In one embodiment, n is an integer from 10 to 100. In one embodiment, n is an integer from 25 to 100. In one embodiment, n is an integer from 25 to 75. In certain embodiments, n is 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195 or 200. In one embodiment, n is a value that results in PEG having a molecular weight of about 1 kDa to about 5 kDa. In one embodiment, n is a value that results in PEG having a molecular weight of about 3 kDa As shown above, IMDQ-PEG-CHOL is imidazoquinoline 1-(4-(aminomethyl)benzyl)-2-butyl-1H-imidazo[4,5-c]quinolin-4-amine (IMDQ) conjugated to cholesteryl-poly(ethylene glycol) (CHOL-PEG). Further provided herein are enantiomers, mixtures of enantiomers, tautomers, and pharmaceutically acceptable salts of IMDQ-PEG-CHOL. In one embodiment, the lipidated imidazoquinoline compound is IMDQ-PEG-CHOL or an enantiomer, a mixture of enantiomers, a tautomer, or a pharmaceutically acceptable salt thereof.

5.2 Synthesis of IMDQ-PEG-CHOL

IMDQ-PEG-CHOL can be prepared according to methods known in the art, including those set forth in Lynn et al. "In vivo characterization of the physicochemical properties of polymer-linked TLR agonists that enhance vaccine immunogenicity," Nat Biotechnol, 33(11):1201-10 (2015). The PEG-CHOL portion of IMDQ-PEG-CHOL can also be prepared according to methods known in the art, including those set forth in De Vrieze et al. "Lipid Nature and Alkyl Length Influence Lymph Node Accumulation of Lipid-Polyethylene Glyco Amphiphiles," *Adv. Ther.*, 4(8):1-9 (2021). A particular route for the synthesis of IMDQ-PEG-CHOL is provided herein in Section 6.

5.3 Antigens of Interest

An antigen of interest can be, e.g., inactivated virus, a killed bacteria, an amino acid-based antigen (e.g., a peptide, polypeptide, or protein antigen), a nucleic acid-based antigen (e.g., an RNA-based antigen), a polysaccharide antigen, or a conjugate (e.g., a polysaccharide-protein conjugate). In some embodiments, an antigen of interest causes or is associated with a disease or disorder. In certain embodiments, an antigen of interest comprises a naturally occurring molecule (e.g., a protein or fragment thereof, or a polysaccharide or fragment thereof). In some embodiments, an antigen of interest comprises a genetically engineered molecule, which is engineered to induce an immune response to a naturally occurring molecule (e.g., a protein, or a polysaccharide). In a specific embodiment, an antigen of interest is foreign or heterologous to the subject being administered an immunogenic composition. As used herein, the term "heterologous" in the context of an antigen refers to an antigen not found in nature to be present or otherwise associated with a subject (e.g., a human).

In certain embodiments, an antigen of interest is obtained from or derived from a pathogen. In some embodiments, the antigen of interest is an antigen of a pathogen. In specific embodiments, the antigen of interest is an infectious disease antigen. In certain embodiments, an antigen of interest is a viral antigen. In specific embodiments, the viral antigen comprises a viral protein or a fragment thereof. In certain embodiments, an antigen of interest is a bacterial antigen. In specific embodiments, a bacterial antigen comprises a bacterial protein or fragment thereof. In certain embodiments, a bacterial antigen comprises a bacterial polysaccharide, or a bacterial polysaccharide conjugated to a carrier protein (e.g., tetanus toxoid, diphtheria toxoid, or CRM197). In some embodiments, an antigen of interest is a parasitic antigen. In specific embodiments, a parasitic antigen comprises a parasitic protein or a fragment thereof. In certain embodiments, an antigen of interest is a fungal antigen. In specific embodiments, a fungal antigen comprises a fungal protein or a fragment thereof. In some embodiments, an antigen of interest is a protozoan antigen. In specific embodiments, a protozoan antigen comprises a protozoan protein or a fragment thereof.

In specific embodiments, an antigen of interest is a SARS-CoV-2 antigen. In specific embodiments, the SARS-CoV-2 antigen is the SARS-CoV-2 spike protein or a fragment thereof. In specific embodiments, the fragment comprises the receptor binding domain of a SARS-CoV-2 spike protein. In certain embodiments, the fragment comprises the ectodomain of a SARS-CoV-2 spike protein. In some embodiments, the fragment comprises the S1 domain, or the S2 domain of a SARS-CoV-2 spike protein.

As used herein, the terms "SARS-CoV-2 spike protein" and "spike protein of SARS-CoV-2" include a SARS-CoV-2 spike protein known to those of skill in the art. See, e.g., GenBank Accession Nos. MN908947.3, MT447160, MT44636, MT446360, MT444593, MT444529, MT370887, and MT334558 for examples of amino acid sequences of SARS-CoV-2 spike protein and nucleotide sequences encoding SARS-CoV-2 spike protein. In certain embodiments, the spike protein comprises the amino acid or nucleic acid sequence found at GenBank Accession No. MN908947.3. In certain embodiments, the spike protein comprises the amino acid or nucleic acid sequence of a variant of SARS-CoV-2. A typical spike protein comprises domains known to those of skill in the art including an S1 domain, a receptor binding domain, an S2 domain, a transmembrane domain and a cytoplasmic domain. See, e.g., Wrapp et al., 2020, Science 367: 1260-1263 or Duan et al., 2020, Frontiers in Immunology Vol. 11, Article 576622 for a description of SARS-CoV-2 spike protein (in particular, the structure of such protein). The spike protein may be characterized has having a signal peptide, a receptor binding domain, an ectodomain, and a transmembrane and endodomain. The terms "SARS-CoV-2 spike protein" encompass SARS-CoV-2 spike polypeptides that are modified by post-translational processing such as signal peptide cleavage, disulfide bond formation, glycosylation (e.g., N-linked glycosylation), protease cleavage and lipid modification (e.g. S-palmitoylation). In some embodiments, the SARS-CoV-2 spike protein includes a signal sequence. In other embodiments, SARS-CoV-2 spike protein does not include a signal sequence. The signal sequence can be the naturally occurring signal peptide sequence or a variant thereof. In some embodiments, the signal peptide is an SARS-CoV-2 spike protein signal peptide. In some embodiments, the signal peptide is heterologous to an SARS-CoV-2 spike protein signal peptide. As used herein, the term "heterologous" in the context of an amino acid sequence or nucleotide sequence refers to a first amino acid sequence or nucleotide sequence not found in nature to be present or otherwise associated with a second amino acid or nucleotide sequence, respectively.

In certain embodiments, a SARS-CoV-2 antigen comprises the ectodomain of a SARS-CoV-2 spike protein with an inactivated polybasic cleavage site at amino acid residues corresponding to amino acid residues 682 to 685 of GenBank Accession No. MN908947.3. In some embodiments, a SARS-CoV-2 antigen comprises the ectodomain of a SARS-CoV-2 spike protein with one or more amino acid substitutions in the polybasic cleavage site (e.g., RRAR to A). In certain embodiments, a SARS-CoV-2 antigen comprises the ectodomain of a SARS-CoV-2 spike protein with one or more amino acid substitutions in the polybasic cleavage site (e.g., RRAR to A) and one, two, or more amino acid substitutions, which introduce proline residues (e.g., amino acid substitutions to prolines at amino acid residues corresponding to amino acid residues 986 and 987 of GenBank Accession No. MN908947.3). In specific embodiments, the one or more amino acid substitutions in the polybasic cleavage site inactivate the cleavage site so that it is unable to be cleaved by, e.g., furin. In certain embodiments, the SARS-CoV-2 antigen further comprises a trimerization domain (e.g., a T4 foldon trimerization domain). In some embodiments, the SARS-CoV-2 antigen further comprises a trimerization domain (e.g., a T4 foldon trimerization domain) and a tag, such as a hexa-histidine tag or flag tag. In specific embodiments, the ectodomain is directly or indirectly linked to a trimerization domain (e.g., a T4 foldon trimerization domain). In certain embodiments, the SARS-CoV-2 ectodomain is linked directly to trimerization domain. In other embodiments, the SARS-CoV-2 ectodomain is linked to a trimerization domain through a linker. In some embodiments, the trimerization domain is linked directly or indirectly (e.g., via a linker) to a tag. In specific embodiments, the linker does not interfere with the structure and/or function of the SARS-CoV-2 ectodomain. In some embodiments, the linker is a glycine linker (e.g., $G_n$, where n is 1, 2, 3, 4, 5, 6 or more), or a serine glycine linker.

In specific embodiments, a SARS-CoV-2 antigen comprises the ectodomain of a SARS-CoV-2 spike protein with an RRAR to A amino acid substitution at amino acid residues corresponding to amino acid residues 682 to 685 of GenBank Accession No. MN908947.3, substitution of the two residues corresponding to amino acid residues 986 and 987 of GenBank Accession No. MN908947.3, a T4 trimerization domain, and a hexa-histidine tag. In a specific embodiment, a SARS-CoV-2 antigen is one described in the Examples below.

In specific embodiments, an antigen of interest is an influenza virus antigen (e.g., an influenza A virus and/or influenza B virus). In certain embodiments, the influenza virus antigen comprises a hemagglutinin protein or a fragment thereof. In some embodiments, the influenza virus antigen is a chimeric influenza virus hemagglutinin protein. In specific embodiments, the chimeric influenza virus hemagglutinin comprises a globular head domain of influenza virus (e.g., influenza A virus or influenza B virus) hemagglutinin that is heterologous to the stem domain of the hemagglutinin. In some embodiments, the influenza virus antigen comprises an influenza virus neuraminidase protein or a fragment thereof.

In specific embodiments, an antigen of interest is a respiratory syncytial virus antigen or human metapneumovirus antigen. In some embodiments, the RSV antigen comprises an RSV F protein or fragment thereof. In some embodiments, the RSV antigen comprises an RSV G protein or fragment thereof. "RSV G protein" and "respiratory syncytial virus G protein" refer to any respiratory syncytial G protein known to those of skill in the art. In one embodiment, the viral antigen is a RSV F protein or a fragment thereof "RSV F protein" and "respiratory syncytial virus F protein" refer to any respiratory syncytial F protein known to those of skill in the art. The RSV F protein typically exists as a homotrimer. The RSV F protein is synthesized as a F0 inactive precursor which is heavily N-glycosylated. The F0 inactive precursor requires cleavage during intracellular maturation by a furin-like proteases. The RSV F contains two furin sites, and cleavage by furin-like proteases leads to three polypeptides: F2, p27 and F1, with the latter containing a hydrophobic fusion peptide at its N terminus. The RSV F protein exists in two conformations, prefusion and post-fusion. The RSV F protein may be human RSV F protein or bovine F protein. GenBank™ accession numbers KJ155694.1, KU950686.1, KJ672481.1, KP119747, and AF035006.1 provide exemplary nucleic acid sequences encoding human RSV F protein. GenBank™ accession numbers AHL84194.1, AMT79817.1, AHX57603.1, AIY70220.1 and AAC14902.1 provide exemplary human RSV F protein amino acid sequences. GenBank™ accession numbers AF295543.1, AF092942.1, and Y17970.1 provide exemplary nucleic acid sequences encoding bovine RSV F protein. GenBank™ accession numbers AAL49399.1, NP_048055.1, AAC96308.1, and CAA76980.1 provide exemplary bovine RSV F protein amino acid sequences. The terms "RSV F protein" and "respiratory syncytial virus F protein" encompass RSV F polypeptides that are modified by post-translational processing such as signal peptide cleavage, disulfide bond formation, glycosylation (e.g., N-linked glycosylation), protease cleavage and lipid modification (e.g. S-palmitoylation). In some embodiments, the RSV F protein includes a signal sequence. In other embodiments, RSV F protein does not include a signal sequence. The signal sequence can be the naturally occurring signal peptide sequence or a variant thereof. The RSV F protein signal sequence is typically 25 amino acids in length. In some embodiments, the signal peptide is an RSV F protein signal peptide. In some embodiments, the signal peptide is heterologous to an RSV F protein signal peptide.

In specific embodiments, an antigen of interest is a human metapneumovirus (hMPV) antigen. In some embodiments, the human metapneumovirus antigen is a human metapneumovirus F protein or fragment thereof. In some embodiments, the human metapneumovirus antigen is a human metapneumovirus G protein or fragment thereof. Human Metapneumovirus G protein" and "hMPV G protein" refer to any Human Metapneumovirus G protein known to those of skill in the art. In another embodiment, the viral antigen is a human metapneumovirus F protein or a fragment thereof "Human Metapneumovirus F protein" and "hMPV F protein" refer to any Human Metapneumovirus F protein known to those of skill in the art. The hMPV F protein is synthesized as a F0 inactive precursor. The F0 inactive precursor requires cleavage during intracellular maturation. The hMPV F is cleaved to form F1 and F2. The hMPV F protein exists in two conformations, prefusion and post-fusion. GenBank™ accession number AY145301.1 and KJ627437.1, provide exemplary nucleic acid sequences encoding hMPV F protein. GenBank™ accession numbers AAN52915.1, AHV79975.1, AGJ74035.1, and AGZ48845.1 provide exemplary hMPV F protein amino acid sequences. The terms "hMPV F protein" and "human metapneumovirus F protein" encompass hMPV F polypeptides that are modified by post-translational processing such as signal peptide cleavage, disulfide bond formation, glycosylation (e.g., N-linked glycosylation), protease cleavage and lipid modification (e.g. S-palmitoylation). In some embodiments, the hMPV F protein includes a signal sequence. In other embodiments, hMPV F protein does not include a signal sequence. The signal sequence can be the naturally occurring signal peptide sequence or a variant thereof. The hMPV F protein signal sequence is typically 18 amino acids in length. In some embodiments, the signal peptide is an hMPV F protein signal peptide. In some embodiments, the signal peptide is heterologous to an hMPV F protein signal peptide.

In specific embodiments, an antigen of interest is a MERS-CoV antigen (e.g, a MERS-CoV spike protein or a fragment thereof, or nucleocapsid protein or a fragment thereof). In specific embodiments, an antigen of interest is a Lassa virus antigen, Ebola virus antigen or Nipah virus antigen. In one embodiment, an antigen of interest is an Ebola virus antigen (e.g., Ebola virus glycoprotein GP or a fragment thereof, or Ebola virus nucleocapsid or a fragment thereof). In another embodiment, an antigen of interest is a Lassa virus antigen (e.g., a Lassa virus envelope glycoprotein GP1 or a fragment thereof, or a Lassa virus envelope glycoprotein GP2 or a fragment thereof). In another embodiment, an antigen of interest is Nipah virus antigen (e.g., Nipah virus F or a fragment thereof, or a Nipah virus G protein or a fragment thereof). In another embodiment, an antigen of interest is a MERS-CoV antigen (e.g, a MERS-CoV spike protein or a fragment thereof, or nucleocapsid protein or a fragment thereof).

In some embodiments, a fragment of a protein comprises at least 20, at least 30, at least 40, at least 50 or more contiguous amino acids of the protein. In certain embodiments, a fragment of a protein comprises at least 75, at least 100, at least 125, at least 150 or more contiguous amino acids of the protein. In certain embodiments, a fragment of a protein comprises 20 to 50 contiguous amino acids of the protein. In some embodiments, a fragment of a protein comprises 25 to 50 contiguous amino acids of the protein. In certain embodiments, a fragment of a protein comprises 50 to 75 contiguous amino acids of the protein. In some embodiments, a fragment of a protein comprises 50 to 100 contiguous amino acids of the protein. In certain embodiments, a fragment of a protein comprises 75 to 100 contiguous amino acids of the protein. In certain embodiments, a fragment of a protein comprises 50 to 150 contiguous amino acids of the protein. In certain embodiments, a fragment of a protein comprises 100 to 150 contiguous amino acids of the protein. In certain embodiments, a fragment of a protein comprises 100 to 200 contiguous amino acids of the protein.

In a specific embodiment, an antigen of interest comprises an inactivated virus. Techniques known to one of skill in the art may be used to inactivate a virus. In certain embodiments, an antigen of interest is a split virus. In a specific embodiment, the antigen comprises a three or four inactivated influenza viruses. In a specific embodiment, the antigen comprises a trivalent or quadravalent inactivated influenza virus composition. In some embodiments, an antigen of interest comprises an inactivated polio virus. In certain embodiments, an antigen of interest comprises an inactivated hepatitis A virus. In some embodiments, an antigen of interest comprises an inactivated Japanese Encephalitis virus.

In a specific embodiment, an antigen of interest comprises *Clostridium tetani* antigen. In another specific embodiment, an antigen of interest comprises a *Bacillus* antigen. In another specific embodiment, an antigen of interest comprises a *Bordetella pertussis* antigen. In another specific embodiment, an antigen of interest comprises *Streptococcus pneumoniae* antigen. In another specific embodiment, an antigen of interest comprises a *Neisseria meningitides* antigen. In another specific embodiment, an antigen of interest comprises a *Haemophilus influenzae* antigen. In another specific embodiment, an antigen of interest comprises a *Bacillus anthracis* antigen. In another specific embodiment, an antigen of interest comprises a *Corynebacterium* diphtherias antigen.

In certain embodiments, an antigen of interest is a cell-free, aviralent bacteria strain. In specific embodiments, an antigen of interest comprises a cell-free filtrate(s) of microaerophilic cultures of an avirulent, nonencapsulated strain of *Bacillus anthracis*. In some embodiments, an antigen of interest comprises a killed bacteria.

In some embodiments, an antigen of interest comprises a *Haemophilus* b conjugate. In certain embodiments, an antigen of interest comprises a Meningococcal conjugate. In some embodiments, an antigen of interest comprises a pneumococcal polysaccharide conjugate.

In certain embodiments, an antigen of interest comprises a diphtheria toxoid. In some embodiments, an antigen of interest comprises a tetanus toxoid. In certain embodiments, an antigen of interest comprises acellular pertussis.

In certain embodiments, an antigen of interest comprises a lipid nanoparticle formulated antigen. In some embodiments, an antigen of interest is an RNA-based vaccine, such as a Pfizer SARS-CoV-2 vaccine, or a Moderna SARS-CoV-2 vaccine.

In certain embodiments, an antigen of interest comprises an mRNA antigen. In certain embodiments, an antigen of interest comprises a lipid nanoparticle formulated RNA (e.g., mRNA) antigen.

In certain embodiments, a cancer antigen is a tumor antigen. The tumor antigen may be a tumor-associated antigen, or a tumor-specific antigen. Examples of tumor antigens include CEA, Immature laminin receptor, TAG-72, HPV E6, HPV, E7, BING-4, Calcium-activated chloride channel 2, 9D7, Ep-CAM, EphA3, Her2/neu, Mesothelin, SAP-1, Survivin, NY-ESO-1/LAGE-1, Melan-A/MART-1, BRCA1/2, MART-2, and Ras.

In some embodiments, an antigen of interest is an antigen present in a vaccine approved by a regulatory agency, or one undergoing clinical trials. In a specific embodiment, an antigen of interest comprises an antigen described herein (e.g., in the Examples).

5.4 Compositions

Provided herein are compositions comprising an IMDQ-PEG-CHOL compound described herein (e.g., Section 5.1, 6, 8 or 9). In a specific embodiment, the compositions are pharmaceutical compositions. In another specific embodiment, the compositions are immunogenic compositions (e.g., vaccines). In a specific embodiment, provided herein are immunogenic compositions comprising an IMDQ-PEG-CHOL compound described herein (e.g., Section 5.1, 6, 8 or 9) and an antigen of interest. Such immunogenic compositions may be monovalent or multi-valent. In certain embodiments, an immunogenic composition comprises a single antigen of interest and an IMDQ-PEG-CHOL compound described herein. In other embodiments, an immunogenic composition comprises two, three, or antigen of interests and an IMDQ-PEG-CHOL compound described herein. The compositions may be used in methods of inducing an immune response to an antigen, such as described herein (e.g., in Section 5.4, 6, 8 or 9). The compositions may be used in methods for immunizing against an antigen (e.g., an antigen described herein (e.g., in Section 5.3, 5.4, 6, 8, or 9)). The compositions may be used in methods for immunizing against a disease or disorder associated with an antigen (e.g., an antigen described herein (e.g., in Section 5.3, 5.4, 6, 8, or 9)). The compositions may be used in methods for preventing a disease with which an antigen, such as an antigen described herein (e.g., in Section 5.3, 5.4, 6, 8 or 9), is associated. A pharmaceutical composition comprising an IMDQ-PEG-CHOL compound described herein may be used in methods for enhancing the immune response (e.g., humoral immune response, cellular immune response, or both) to an antigen of interest.

In one embodiments, a pharmaceutical composition comprises an IMDQ-PEG-CHOL compound described herein (e.g., Section 5.1, 6, 8 or 9), in an admixture with a pharmaceutically acceptable carrier. The composition may comprise 0.1 microgram to 100 micrograms of an IMDQ-PEG-CHOL compound described herein (e.g., Section 5.1, 6, 8 or 9). In a specific embodiment, a pharmaceutical composition comprises an effective amount of an IMDQ-PEG-CHOL compound described herein (e.g., Section 5.1, 6, 8 or 9)

In some embodiments, a composition (e.g., an immunogenic composition) comprises an IMDQ-PEG-CHOL compound described herein (e.g., Section 5.1, 6, 8 or 9), in an admixture with a pharmaceutically acceptable carrier. The composition may comprise 0.1 microgram to 100 micrograms of an IMDQ-PEG-CHOL compound described herein (e.g., Section 5.1, 6, 8 or 9). In some embodiments, the composition further comprises one or more antigens of interest. In a specific embodiment, a composition comprises an effective amount of an IMDQ-PEG-CHOL compound described herein (e.g., Section 5.1, 6, 8 or 9) and optionally one or more antigens of interest, in a pharmaceutically acceptable carrier. In specific embodiments, a composition comprises an effective amount of an IMDQ-PEG-CHOL compound described herein (e.g., Section 5.1, 6, 8 or 9) and an effective amount of one or more antigens of interest, in a pharmaceutically acceptable carrier. In some embodiments, an IMDQ-PEG-CHOL compound described herein (e.g., Section 5.1, 6, 8 or 9) is the only active ingredient included in the composition. In a specific embodiment, the composition is an immunogenic composition.

In certain embodiments, an effective amount of an IMDQ-PEG-CHOL compound described herein or a composition thereof is an amount (e.g., dosage) described herein. In specific embodiments, an effective amount of an IMDQ-PEG-CHOL compound described herein or a composition thereof is an amount effective to enhance the immune response in a subject to an antigen of interest, as assessed by a method known to one of skill in the art or described herein. In specific embodiments, an effective amount of an antigen of interest is an amount known to one of skill in the art, or described herein. In some embodiments, an effective amount of an antigen of interest is an amount that in combination with an IMDQ-PEG-CHOL compound described herein induces an immune response.

The compositions provided herein can be in any form that allows for the composition to be administered to a subject. In a specific embodiment, the compositions are suitable for veterinary administration, human administration, or both. As used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the composition is administered. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Examples of suitable pharmaceutical carriers are described in "Remington's Pharmaceutical Sciences" by E. W. Martin. The formulation should suit the mode of administration.

In a specific embodiment, the compositions are formulated to be suitable for the intended route of administration to a subject. For example, the composition may be formulated to be suitable for parenteral, intravenous, intra-arterial, intrapleural, inhalation, intratumoral, intranasal, intraperitoneal, oral, intradermal, colorectal, intraperitoneal, and intracranial administration. In one embodiment, the pharmaceutical composition may be formulated for intravenous, intra-arterial, oral, intraperitoneal, intranasal, intratracheal, intrapleural, intracranial, subcutaneous, intramuscular, topical, or pulmonary administration. In a specific embodiment, the composition may be formulated for subcutaneous or intramuscular administration.

5.5 Uses of an IMDQ-PEG-CHOL Compound as an Adjuvant

In one aspect, provided herein is the use of an IMDQ-PEG-CHOL compound described herein as an adjuvant. In one embodiment, an IMDQ-PEG-CHOL compound described herein is used as an adjuvant in an immunogenic composition (e.g., a vaccine) comprising an antigen of interest. See, e.g., Section 5.3 and the Examples, infra, for antigens of interest. In a specific embodiment, provided herein is a method for enhancing the immune response to an antigen of interest in a subject, comprising administering an immunogenic composition comprising the antigen of interest and an IMDQ-PEG-CHOL compound described herein to the subject. In certain embodiments, the immune response achieved by administering the immunogenic composition to the subject is higher relative to the immune response achieved by administering the same composition lacking the IMDQ-PEG-CHOL compound, or the same composition with IMDQ, AddaVax, or AddaS03 in place of the IMDQ-PEG-CHOL compound to a subject of the same species (e.g., a subject with a similar background genetically and/or health wise), as assessed by an assay described herein (e.g., an assay described in the Examples), or known to one of skill in the art. In some embodiments, the immune response is at least 10%, at least 20%, at least 25%, at least 30%, at least 40% or at least 50% higher. In some embodiments, the immune response is at least 60%, at least 70%, at least 75%, at least 80%, at least 85%, at least 90% or at least 95% higher. In some embodiments, the humoral immune response is higher. In certain embodiments, the cellular immune response is higher. In some embodiments, the humoral and cellular immune responses are higher. In certain embodiments, the antigen of interest is an infectious disease antigen. In some embodiments, the antigen of interest is an antigen of a pathogen. In certain embodiments, the antigen of interest is viral antigen, a bacterial antigen, a fungal antigen, or a parasitic antigen. In specific embodiments, the antigen of interest is a SARS-CoV-2 antigen, an influenza virus antigen, MERS-CoV antigen, human metapneumovirus antigen, respiratory syncytial virus (RSV) antigen, Lassa virus antigen, Ebola virus antigen, or Nipah virus antigen. The antigen of interest can be, e.g., inactivated virus, a protein antigen, a nucleic acid-based antigen (e.g., an RNA-based antigen), a polysaccharide antigen, or a conjugate (e.g., a polysaccharide-protein conjugate). In specific embodiments, the antigen of interest is a cancer antigen. In a specific embodiment, the cancer antigen is a tumor antigen. The tumor antigen may be a tumor-associated antigen, or a tumor-specific antigen. Examples of tumor antigens include CEA, Immature laminin receptor, TAG-72, HPV E6, HPV, E7, BING-4, Calcium-activated chloride channel 2, 9D7, Ep-CAM, EphA3, Her2/neu, Mesothelin, SAP-1, Survivin, NY-ESO-1/LAGE-1, Melan-A/MART-1, BRCA1/2, MART-2, and Ras. In a specific embodiment, an antigen of interest is foreign or heterologous to the subject being administered an immunogenic composition. In specific embodiments, the antigen of interest is one described in the Examples, infra. In certain embodiments, an immunogenic composition comprising an antigen of interest is a monovalent composition (e.g., a monovalent vaccine). In other embodiments, an immunogenic composition comprising an antigen of interest is a multi-valent composition (e.g. a multi-valent vaccine).

In another aspect, provided herein is a method of inducing an immune response to an antigen of interest in a subject, comprising administering to the subject an immunogenic composition (e.g., a vaccine) comprising an IMDQ-PEG-CHOL compound described herein and the antigen of interest. See, e.g., Section 5.3 and the Examples (Sections 6, 8 and 9), infra, for antigens of interest. The immunogenic composition may be administered by any route. For example, the immunogenic composition may be administered parenterally, intranasally, intradermally, or orally. In certain embodiments, the immunogenic composition is administered subcutaneously or intramuscularly. In certain embodiments, the antigen of interest is an infectious disease antigen. In some embodiments, the antigen of interest is an antigen of a pathogen. In certain embodiments, the antigen of interest is viral antigen, a bacterial antigen, a fungal antigen, or a parasitic antigen. In specific embodiments, the antigen of interest is a SARS-CoV-2 antigen, an influenza virus antigen, MERS-CoV antigen, human metapneumovirus antigen, respiratory syncytial virus (RSV) antigen, Lassa virus antigen, Ebola virus antigen, or Nipah virus antigen. The antigen can be, e.g., inactivated virus, a protein antigen, a nucleic acid-based antigen (e.g., an RNA-based antigen), a polysaccharide antigen, or a conjugate (e.g., a polysaccharide-protein conjugate). In a specific embodiment, an antigen of interest is foreign or heterologous to the subject being administered an immunogenic composition. In specific embodiments, the antigen of interest is one described in the Examples, infra. In certain embodiments, an immunogenic composition comprising an antigen of interest is a monovalent composition (e.g., a monovalent vaccine). In other embodiments, an immunogenic composition comprising an antigen of interest is a multi-valent composition (e.g. a multi-valent vaccine).

As used herein, the terms "subject" and "patient" are used interchangeably. As used herein, the terms "subject" and "subjects" refers to an animal. In some embodiments, the subject is a mammal including a non-primate (e.g., a camel, donkey, zebra, bovine, horse, horse, cat, dog, rat, and mouse) and a primate (e.g., a monkey, chimpanzee, and a human). In some embodiments, the subject is a non-human mammal. In certain embodiments, the subject is a pet (e.g., dog or cat) or farm animal (e.g., a horse, pig or cow). In specific embodiments, the subject is a human.

In a specific embodiment, provided herein is a method of inducing an immune response to SARS-CoV-2 in a subject, comprising administering to the subject an immunogenic composition (e.g., a vaccine) comprising an IMDQ-PEG-CHOL compound described herein and a SARS-CoV-2 antigen. The SARS-CoV-2 antigen may be one described herein (e.g., one described in the Examples), or known to one of skill in the art. In another specific embodiment, provided herein is a method of inducing an immune response to influenza virus (e.g., influenza A virus and/or influenza B virus) in a subject, comprising administering to the subject an immunogenic composition (e.g., a vaccine) comprising an IMDQ-PEG-CHOL compound described herein and an influenza virus antigen (e.g., an influenza A virus antigen and/or an influenza B virus antigen). The influenza virus antigen may be one described herein (e.g., one described in the Examples), or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method of inducing an immune response to RSV in a subject, comprising administering to the subject an immunogenic composition (e.g., a vaccine) comprising an IMDQ-PEG-CHOL compound described herein and a RSV antigen.

The RSV antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method of inducing an immune response to MERS-CoV in a subject, comprising administering to the subject an immunogenic composition (e.g., a vaccine) comprising an IMDQ-PEG-CHOL compound described herein and a MERS-CoV antigen. The MERS-CoV antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method of inducing an immune response to hMPV in a subject, comprising administering to the subject an immunogenic composition (e.g., a vaccine) comprising an IMDQ-PEG-CHOL compound described herein and a hMPV antigen. The hMPV antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method of inducing an immune response to Lassa virus in a subject, comprising administering to the subject an immunogenic composition (e.g., a vaccine) comprising an IMDQ-PEG-CHOL compound described herein and a Lassa virus antigen. The Lassa virus antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method of inducing an immune response to Ebola virus in a subject, comprising administering to the subject an immunogenic composition (e.g., a vaccine) comprising an IMDQ-PEG-CHOL compound described herein and an Ebola virus antigen. The Ebola virus antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method of inducing an immune response to Nipah virus in a subject, comprising administering to the subject an immunogenic composition (e.g., a vaccine) comprising an IMDQ-PEG-CHOL compound described herein and a Nipah virus antigen. The Nipah virus antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method of inducing an immune response to *Corynebacterium diphtheriae* in a subject, comprising administering to the subject an immunogenic composition (e.g., a vaccine) comprising an IMDQ-PEG-CHOL compound described herein and a *Corynebacterium diphtheriae* antigen (e.g., diphtheria toxoid). The *Corynebacterium diphtheriae* antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method of inducing an immune response to poliovirus in a subject, comprising administering to the subject an immunogenic composition (e.g., a vaccine) comprising an IMDQ-PEG-CHOL compound described herein and a poliovirus antigen (e.g., inactivated poliovirus). The poliovirus antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method of inducing an immune response to hepatitis A virus in a subject, comprising administering to the subject an immunogenic composition (e.g., a vaccine) comprising an IMDQ-PEG-CHOL compound described herein and a hepatitis A virus antigen. The hepatitis A virus antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method of inducing an immune response to Japanese Encephalitis virus in a subject, comprising administering to the subject an immunogenic composition (e.g., a vaccine) comprising an IMDQ-PEG-CHOL compound described herein and a Japanese Encephalitis virus antigen. The Japanese Encephalitis virus antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method of inducing an immune response to *Haemophilus influenzae* in a subject, comprising administering to the subject an immunogenic composition (e.g., a vaccine) comprising an IMDQ-PEG-CHOL compound described herein and a *Haemophilus influenzae* antigen (e.g. heamophilus b conjugate). The *Haemophilus influenzae* antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method of inducing an immune response to *Neisseria meningitidis* in a subject, comprising administering to the subject an immunogenic composition (e.g., a vaccine) comprising an IMDQ-PEG-CHOL compound described herein and a *Neisseria meningitidis* antigen (e.g., meningococcal conjugate). The *Neisseria meningitidis* antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method of inducing an immune response to *Streptococcus*

*pneumoniae* in a subject, comprising administering to the subject an immunogenic composition (e.g., a vaccine) comprising an IMDQ-PEG-CHOL compound described herein and a pneumococcal antigen (e.g., a polysaccharide or pneumococcal conjugate). The pneumococcal antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method of inducing an immune response to *Bordetella pertussis* in a subject, comprising administering to the subject an immunogenic composition (e.g., a vaccine) comprising an IMDQ-PEG-CHOL compound described herein and a *Bordetella pertussis* antigen. The *Bordetella pertussis* antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method of inducing an immune response to *Bacillus* (e.g., *Bacillus anthracis*) in a subject, comprising administering to the subject an immunogenic composition (e.g., a vaccine) comprising an IMDQ-PEG-CHOL compound described herein and a *Bacillus* antigen. The *Bacillus* antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method of inducing an immune response to *Clostridium tetani* in a subject, comprising administering to the subject an immunogenic composition (e.g., a vaccine) comprising an IMDQ-PEG-CHOL compound described herein and a *Clostridium tetani* antigen (e.g., tetanus toxoid). The *Clostridium tetani* may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method of inducing an immune response to a cancer antigen in a subject, comprising administering to the subject an immunogenic composition (e.g., a vaccine) comprising an IMDQ-PEG-CHOL compound described herein and a cancer antigen. In a specific embodiment, the cancer antigen is a tumor antigen. The tumor antigen may be a tumor-associated antigen, or a tumor-specific antigen. Examples of tumor antigens include CEA, Immature laminin receptor, TAG-72, HPV E6, HPV, E7, BING-4, Calcium-activated chloride channel 2, 9D7, Ep-CAM, EphA3, Her2/neu, Mesothelin, SAP-1, Survivin, NY-ESO-1/LAGE-1, Melan-A/MART-1, BRCA1/2, MART-2, and Ras.

In a specific embodiment, provided herein is a method of inducing an immune response to an antigen in a subject, comprising administering an immunogenic composition described herein (e.g., in Section 5.3 or the Examples (Sections 6, 8, and 9), infra) to the subject.

In another aspect, provided herein is a method for immunizing a subject against a disease or disorder associated with an antigen, comprising administering to the subject an immunogenic composition (e.g., a vaccine) comprising an IMDQ-PEG-CHOL compound described herein and an antigen of interest. The immunogenic composition may be administered by any route. For example, the immunogenic composition may be administered parenterally, intranasally, intradermally, or orally. In certain embodiments, the immunogenic composition is administered subcutaneously or intramuscularly. The antigen associated with the disease or disorder may be the same or different than the antigen of interest. For example, the antigen of interest may be a modified form or derivative of an antigen associated with the disease or disorder. See, e.g., Section 5.3 and the Examples (Sections 6, 8, and 9), infra, of antigens of interest. In certain embodiments, the antigen is an infectious disease antigen. In some embodiments, the antigen is an antigen of a pathogen. In certain embodiments, the antigen is viral antigen, a bacterial antigen, a fungal antigen, or a parasitic antigen. In specific embodiments, the antigen is a SARS-CoV-2 antigen, an influenza virus antigen, MERS-CoV antigen, human metapneumovirus antigen, respiratory syncytial virus (RSV) antigen, Lassa virus antigen, Ebola virus antigen, or Nipah virus antigen. The antigen can be, e.g., inactivated virus, a protein antigen, a nucleic acid-based antigen (e.g., an RNA-based antigen), a polysaccharide antigen, or a conjugate (e.g., a polysaccharide-protein conjugate). In certain embodiments, the antigen is a cancer antigen. In a specific embodiment, the cancer antigen is a tumor antigen. The tumor antigen may be a tumor-associated antigen, or a tumor-specific antigen. Examples of tumor antigens include CEA, immature laminin receptor, TAG-72, HPV E6, HPV, E7, BING-4, calcium-activated chloride channel 2, 9D7, Ep-CAM, EphA3, Her2/neu, Mesothelin, SAP-1, Survivin, NY-ESO-1/LAGE-1, Melan-A/MART-1, BRCA1/2, MART-2, and Ras. In a specific embodiment, an antigen of interest is foreign or heterologous to the subject being administered an immunogenic composition. In specific embodiments, the antigen of interest is one described in the Examples, infra. In certain embodiments, an immunogenic composition comprising the antigen of interest is a monovalent composition (e.g., a monovalent vaccine). In other embodiments, an immunogenic composition comprising the antigen of interest is a multi-valent composition (e.g. a multi-valent vaccine).

In a specific embodiment, provided herein is a method for immunizing a subject against COVID-19, comprising administering to the subject an immunogenic composition (e.g., a vaccine) comprising an IMDQ-PEG-CHOL compound described herein and a SARS-CoV-2 antigen. The SARS-CoV-2 antigen may be one described herein (e.g., one described in the Examples), or known to one of skill in the art. In another specific embodiment, provided herein is a method for immunizing a subject against influenza virus disease (e.g., influenza A virus and/or influenza B virus), comprising administering to the subject an immunogenic composition (e.g., a vaccine) comprising an IMDQ-PEG-CHOL compound described herein and an influenza virus antigen (e.g., an influenza A virus antigen and/or an influenza B virus antigen). The influenza virus antigen may be one described herein (e.g., one described in the Examples), or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method for immunizing a subject against RSV disease, comprising administering to the subject an immunogenic composition (e.g., a vaccine) comprising an IMDQ-PEG- CHOL compound described herein and a RSV antigen. The RSV antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method for immunizing a subject against Middle East Respiratory Syndrome, comprising administering to the subject an immunogenic composition (e.g., a vaccine) comprising an IMDQ-PEG-CHOL compound described herein and a MERS-CoV antigen. The MERS-CoV antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method for immunizing a subject against hMPV disease, comprising administering to the subject an immunogenic composition (e.g., a vaccine) comprising an IMDQ-PEG-CHOL compound described herein and a hMPV antigen. The hMPV antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method for immunizing a subject against Lassa fever or Lassa hemorrhagic fever, comprising administering to the subject an immunogenic composition (e.g., a vaccine) comprising an IMDQ-PEG-CHOL compound described herein and a Lassa virus antigen. The Lassa virus antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method for immunizing a subject against Ebola virus disease, comprising administering to the subject an immunogenic composition (e.g., a vaccine) comprising an IMDQ-PEG-CHOL compound described herein and an Ebola virus antigen. The Ebola virus antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method for immunizing a subject against Nipah virus disease, comprising administering to the subject an immunogenic composition (e.g., a vaccine) comprising an IMDQ-PEG-CHOL compound described herein and a Nipah virus antigen. The Nipah virus antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method for immunizing a subject against diphtheria, comprising administering to the subject an immunogenic composition (e.g., a vaccine) comprising an IMDQ-PEG-CHOL compound described herein and a *Corynebacterium diphtheriae* antigen (e.g., diphtheria toxoid). The *Corynebacterium diphtheriae* antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method for immunizing a subject against polio, comprising administering to the subject an immunogenic composition (e.g., a vaccine) comprising an IMDQ-PEG-CHOL compound described herein and a poliovirus antigen (e.g., inactivated poliovirus). The poliovirus antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method for immunizing a subject against hepatitis A, comprising administering to the subject an immunogenic composition (e.g., a vaccine) comprising an IMDQ-PEG-CHOL compound described herein and a hepatitis A virus antigen. The hepatitis A virus antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method for immunizing a subject against Japanese encephalitis, comprising administering to the subject an immunogenic composition (e.g., a vaccine) comprising an IMDQ-PEG-CHOL compound described herein and a Japanese Encephalitis virus antigen. The Japanese Encephalitis virus antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method for immunizing a subject against *Haemophilus influenzae* disease, comprising administering to the subject an immunogenic composition (e.g., a vaccine) comprising an IMDQ-PEG-CHOL compound described herein and a *Haemophilus influenzae* antigen (e.g. heamophilus b conjugate). The *Haemophilus influenzae* antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method for immunizing a subject against meningococcal disease, comprising administering to the subject an immunogenic composition (e.g., a vaccine) comprising an IMDQ-PEG-CHOL compound described herein and a *Neisseria meningitidis* antigen (e.g., meningococcal conjugate). The *Neisseria meningitidis* antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method for immunizing a subject against pneumococcal disease (e.g., invasive pneumococcal disease or otitis media), comprising administering to the subject an immunogenic composition (e.g., a vaccine) comprising an IMDQ-PEG-CHOL compound described herein and a pneumococcal antigen (e.g., a polysaccharide or pneumococcal conjugate). The pneumococcal antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method for immunizing a subject against pertussis, comprising administering to the subject an immunogenic composition (e.g., a vaccine) comprising an IMDQ-PEG-CHOL compound described herein and a *Bordetella pertussis* antigen. The *Bordetella pertussis* antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method for immunizing a subject against anthrax, comprising administering to the subject an immunogenic composition (e.g., a vaccine) comprising an IMDQ-PEG-CHOL compound described herein and a *Bacillus* antigen. The *Bacillus* antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method for immunizing a subject against tetanus, comprising administering to the subject an immunogenic composition (e.g., a vaccine) comprising an IMDQ-PEG-CHOL compound described herein and a *Clostridium tetani* antigen (e.g., tetanus toxoid). The *Clostridium tetani* antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method for immunizing a subject against cancer, comprising administering to the subject an immunogenic composition (e.g., a vaccine) comprising an IMDQ-PEG-CHOL compound described herein and a cancer antigen. In a specific embodiment, the cancer antigen is a tumor antigen. The tumor antigen may be a tumor-associated antigen, or a tumor-specific antigen. Examples of tumor antigens include CEA, immature laminin receptor, TAG-72, HPV E6, HPV, E7, BING-4, calcium-activated chloride channel 2, 9D7, Ep-CAM, EphA3, Her2/neu, Mesothelin, SAP-1, Survivin, NY-ESO-1/LAGE-1, Melan-A/MART-1, BRCA1/2, MART-2, and Ras. In specific embodiments, the cancer antigen is associated with the cancer for which the immunogenic composition is administered to the subject. For example, CEA is associated with colorectal carcinoma, immature laminin receptor is associated with RCC, TAB-72 is associated with prostate carcinoma, HPV E6 and HPV E7 are associated with cervical carcinoma, BING-4 is associated with melanoma, calcium-activated chloride channel 2 is associated with lung carcinoma, 9D7 is associated with RCC, Ep-CAM is associated with breast carcinoma, mesothelin is associated with ductal pancreatic carcinoma, SAP-1 is associated with colorectal carcinoma, Melan-A/MART-1 is associated with melanoma, BRCA1/2 is associated with breast and ovarian carcinoma, MART-2 is associated with melanoma, and prostate-specific antigen is associated with prostate cancer. In another example, EphA3, Her2/neu, Survivin, NY-ESO-1/LAGE-1, and Ras are associated with multiple cancers.

In a specific embodiment, provided herein is a method for immunizing a subject against a disease or disorder, comprising administering an immunogenic composition described herein (e.g., in Section 5.4 or the Examples (Sections 6, 8, and 9)) to the subject.

In another aspect, provided herein is a method for preventing, treating, or preventing and treating a disease or disorder associated with an antigen in a subject, comprising administering to the subject an immunogenic composition (e.g., a vaccine) comprising an IMDQ-PEG-CHOL compound described herein and the antigen of interest. In a specific embodiment, provided herein is a method for preventing a disease or disorder associated with an antigen in a subject, comprising administering to the subject an immunogenic composition (e.g., a vaccine) comprising an IMDQ-PEG-CHOL compound described herein and the antigen of interest. In another specific embodiment, provided herein is a method for treating a disease or disorder associated with an antigen in a subject, comprising administering to the subject an immunogenic composition (e.g., a vaccine) comprising an IMDQ-PEG-CHOL compound described herein and the antigen of interest. See, e.g., Section 5.3 and the Examples (Sections 6, 8, and 9), infra, for antigens of interest. The immunogenic composition may be administered by any route. For example, the immunogenic composition may be administered parenterally, intranasally, intradermally, or orally. In certain embodiments, the immunogenic composition is administered subcutaneously or intramuscularly. The antigen associated with the disease or disorder may be the same or different than the antigen of interest. For example, the antigen may be a modified form or derivative of an antigen associated with the disease or disorder. In certain embodiments, the antigen is an infectious disease antigen. In some embodiments, the antigen is an antigen of a pathogen. In certain embodiments, the antigen is viral antigen, a bacterial antigen, a fungal antigen, or a parasitic antigen. In specific embodiments, the antigen is a SARS-CoV-2 antigen, an influenza virus antigen, MERS-CoV antigen, human metapneumovirus antigen, respiratory syncytial virus (RSV) antigen, Lassa virus antigen, Ebola virus antigen, or Nipah virus antigen. The antigen can be, e.g., inactivated virus, a protein antigen, a nucleic acid-based antigen (e.g., an RNA-based antigen), a polysaccharide antigen, or a conjugate (e.g., a polysaccharide-protein conjugate). In certain embodiments, the antigen is a cancer antigen. In a specific embodiment, the cancer antigen is a tumor antigen. The tumor antigen may be a tumor-associated antigen, or a tumor-specific antigen. Examples of tumor antigens include CEA, immature laminin receptor, TAG-72, HPV E6, HPV, E7, BING-4, calcium-activated chloride channel 2, 9D7, Ep-CAM, EphA3, Her2/neu, Mesothelin, SAP-1, Survivin, NY-ESO-1/LAGE-1, Melan-A/MART-1, BRCA1/2, MART-2, and Ras. In a specific embodiment, an antigen of interest is foreign or heterologous to the subject being administered an immunogenic composition. In certain embodiments, an immunogenic composition comprising an antigen of interest is a monovalent composition (e.g., a monovalent vaccine). In a specific embodiment, an antigen of interest is one described in the Examples, infra. In other embodiments, an immunogenic composition comprising an antigen of interest is a multi-valent composition (e.g. a multi-valent vaccine).

In a specific embodiment, provided herein is a method for preventing COVID-19 in a subject, comprising administering to the subject an immunogenic composition (e.g., a vaccine) comprising an IMDQ-PEG-CHOL compound described herein and a SARS-CoV-2 antigen. The SARS-CoV-2 antigen may be one described herein (e.g., one described in the Examples), or known to one of skill in the art. In another specific embodiment, provided herein is a method for preventing influenza virus disease in a subject, comprising administering to the subject an immunogenic composition (e.g., a vaccine) comprising an IMDQ-PEG-CHOL compound described herein and an influenza virus antigen (e.g., an influenza A virus antigen and/or an influenza B virus antigen). The influenza virus antigen may be one described herein (e.g., one described in the Examples), or known to one of skill in the art. In a specific embodiment, an antigen of interest is foreign or heterologous to the subject being administered an immunogenic composition. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method for preventing RSV disease in a subject, comprising administering to the subject an immunogenic composition (e.g., a vaccine) comprising an IMDQ-PEG-CHOL compound described herein and a RSV antigen. The RSV antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method for preventing Middle East Respiratory Syndrome in a subject, comprising administering to the subject an immunogenic composition (e.g., a vaccine) comprising an IMDQ-PEG-CHOL compound described herein and a MERS-CoV antigen. The MERS-CoV antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method for preventing hMPV disease in a subject, comprising administering to the subject an immunogenic composition (e.g., a vaccine) comprising an IMDQ-PEG-CHOL compound described herein and a hMPV antigen. The hMPV antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method for preventing Lassa fever or Lassa hemorrhagic fever in a subject, comprising administering to the subject an immunogenic composition (e.g., a vaccine) comprising an IMDQ-PEG-CHOL compound described herein and a Lassa virus antigen. The Lassa virus antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method for preventing Ebola virus disease in a subject, comprising administering to the subject an immunogenic composition (e.g., a vaccine) comprising an IMDQ-PEG-CHOL compound described herein and an Ebola virus antigen. The Ebola virus antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method for preventing Nipah virus disease in a subject, comprising administering to the subject an immunogenic composition (e.g., a vaccine) comprising an IMDQ-PEG-CHOL compound described herein and a Nipah virus antigen. The Nipah virus antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method for preventing diphtheria in a subject, comprising administering to the subject an immunogenic composition (e.g., a vaccine) comprising an IMDQ-PEG-CHOL compound described herein and a *Corynebacterium diphtheriae* antigen (e.g., diphtheria toxoid). The *Corynebacterium diphtheriae* antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method for preventing polio in a subject, comprising administering to the subject an immunogenic composition (e.g., a vaccine) comprising an IMDQ-PEG-CHOL compound described herein and a poliovirus antigen (e.g., inactivated poliovirus). The poliovirus antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method for preventing hepatitis A in a subject, comprising administering to the subject an immunogenic composition (e.g., a vaccine) comprising an IMDQ-PEG-CHOL compound described herein and a hepatitis A virus antigen. The hepatitis A virus antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method for preventing Japanese encephalitis in a subject, comprising administering to the subject an immunogenic composition (e.g., a vaccine) comprising an IMDQ-PEG-CHOL compound described herein and a Japanese Encephalitis virus antigen. The Japanese Encephalitis virus antigen may be one described herein, or known to one of skill in the art. In certain embodiments, the immunogenic composition is a monovalent composition (e.g., a monovalent vaccine).

In other embodiments, the immunogenic composition is a multi-valent composition (e.g. a multi-valent vaccine).

In another specific embodiment, provided herein is a method for preventing *Haemophilus influenzae* disease in a subject, comprising administering to the subject an immunogenic composition (e.g., a vaccine) comprising an IMDQ-PEG-CHOL compound described herein and a *Haemophilus influenzae* antigen (e.g. heamophilus b conjugate). The *Haemophilus influenzae* antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method for preventing meningococcal disease in a subject, comprising administering to the subject an immunogenic composition (e.g., a vaccine) comprising an IMDQ-PEG-CHOL compound described herein and a *Neisseria meningitidis* antigen (e.g., meningococcal conjugate). The *Neisseria meningitidis* antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method for preventing pneumococcal disease (e.g., invasive pneumococcal disease or otitis media) in a subject, comprising administering to the subject an immunogenic composition (e.g., a vaccine) comprising an IMDQ-PEG-CHOL compound described herein and a pneumococcal antigen (e.g., a polysaccharide or pneumococcal conjugate). The pneumococcal antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method for preventing pertussis in a subject, comprising administering to the subject an immunogenic composition (e.g., a vaccine) comprising an IMDQ-PEG-CHOL compound described herein and a *Bordetella pertussis* antigen. The *Bordetella pertussis* antigen may be one described herein, or known to one of skill in the art. In certain embodiments, the immunogenic composition is a monovalent composition (e.g., a monovalent vaccine). In other embodiments, the immunogenic composition is a multivalent composition (e.g. a multi-valent vaccine).

In another specific embodiment, provided herein is a method for preventing anthrax in a subject, comprising administering to the subject an immunogenic composition (e.g., a vaccine) comprising an IMDQ-PEG-CHOL compound described herein and a *Bacillus* antigen. The *Bacillus* antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In another specific embodiment, provided herein is a method for preventing tetanus in a subject, comprising administering to the subject an immunogenic composition (e.g., a vaccine) comprising an IMDQ-PEG-CHOL compound described herein and a *Clostridium tetani* antigen (e.g., tetanus toxoid). The *Clostridium tetani* antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine).

In a specific embodiment, provided herein is a method for preventing a disease or disorder in a subject, comprising administering an immunogenic composition described herein (e.g., in Section 5.4 or the Examples) to the subject.

In another specific embodiment, provided herein is a method for preventing, treating cancer in a subject, comprising administering to the subject an immunogenic composition (e.g., a vaccine) comprising an IMDQ-PEG-CHOL compound described herein and a cancer antigen. In another specific embodiment, provided herein is a method for preventing cancer in a subject, comprising administering to the subject an immunogenic composition (e.g., a vaccine) comprising an IMDQ-PEG-CHOL compound described herein and a cancer antigen. In a specific embodiment, the cancer antigen is a tumor antigen. The tumor antigen may be a tumor-associated antigen, or a tumor-specific antigen. Examples of tumor antigens include CEA, immature laminin receptor, TAG-72, HPV E6, HPV, E7, BING-4, calcium-activated chloride channel 2, 9D7, Ep-CAM, EphA3, Her2/neu, mesothelin, SAP-1, Survivin, NY-ESO-1/LAGE-1, Melan-A/MART-1, BRCA1/2, MART-2, prostate-specific antigen, and Ras. In specific embodiments, the cancer antigen is associated with the cancer for which the immunogenic composition is administered to the subject. For example, CEA is associated with colorectal carcinoma, Immature laminin receptor is associated with RCC, TAB-72 is associated with prostate carcinoma, HPV E6 and HPV E7 are associated with cervical carcinoma, BING-4 is associated with melanoma, calcium-activated chloride channel 2 is associated with lung carcinoma, 9D7 is associated with RCC, Ep-CAM is associated with breast carcinoma, mesothelin is associated with ductal pancreatic carcinoma, SAP-1 is associated with colorectal carcinoma, Melan-A/MART-1 is associated with melanoma, BRCA1/2 is associated with breast and ovarian carcinoma, MART-2 is associated with melanoma, and prostate-specific antigen is associated with prostate cancer. In another example, EphA3, Her2/neu, Survivin, NY-ESO-1/LAGE-1, and Ras are associated with multiple cancers.

In a specific embodiment, an immunogenic composition comprising an IMDQ-PEG-CHOL compound described herein and an antigen of interest elicits a higher antigen-specific immune response in a subject relative to the antigen-specific immune response elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art. In certain embodiments, an immunogenic composition comprising an IMDQ-PEG-CHOL compound described herein and an antigen of interest elicits a 5% to 50% higher antigen-specific immune response in a subject relative to the antigen-specific immune response elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art. In some embodiments, an immunogenic composition comprising an IMDQ-PEG-CHOL compound described herein and an antigen of interest elicits a 25% to 50% higher antigen-specific immune response in a subject relative to the antigen-specific immune response elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art. In certain embodiments, an immunogenic composition comprising an IMDQ-PEG-CHOL compound described herein and an antigen of interest elicits a 50% to 75% higher antigen-specific immune response in a subject relative to the antigen-specific immune response elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art. In some embodiments, an immunogenic composition comprising an IMDQ-PEG-CHOL compound described herein and an antigen of interest elicits at least a 5%, at least a 10%, at least a 15%, at least a 20%, or at least a 25% higher antigen-specific immune response in a subject relative to the antigen-specific immune response elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art. In certain embodiments, an immunogenic composition comprising an IMDQ-PEG-CHOL compound described herein and an antigen of interest elicits at least a 30%, at least a 35%, at least a 40%, at least a 45%, or at least a 50% higher antigen-specific immune response in a subject relative to the antigen-specific immune response elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art. In some embodiments, an immunogenic composition comprising an IMDQ-PEG-CHOL compound described herein and an antigen of interest elicits at least a 55%, at least a 60%, at least a 65%, at least a 70%, or at least a 75% higher antigen-specific immune response in a subject relative to the antigen-specific immune response elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art.

In a specific embodiment, an immunogenic composition comprising an IMDQ-PEG-CHOL compound described herein and an antigen of interest elicits enhanced immune cell (e.g., T cell, B cell, and/or dendritic cell) recruitment in a subject relative to the immune cell (e.g., T cell, B cell, and/or dendritic cell) recruitment elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art. In certain embodiments, an immunogenic composition comprising an IMDQ-PEG-CHOL compound described herein and an antigen of interest elicits 5% to 50% higher immune cell (e.g., T cell, B cell, and/or dendritic cell) recruitment in a subject relative to the immune cell (e.g., T cell, B cell, and/or dendritic cell) recruitment elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art. In some embodiments, an immunogenic composition comprising an IMDQ-PEG-CHOL compound described herein and an antigen of interest elicits 25% to 50% higher immune cell (e.g., T cell, B cell, and/or dendritic cell) recruitment in a subject relative to the immune cell (e.g., T cell, B cell, and/or dendritic cell) recruitment elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art. In certain embodiments, an immunogenic composition comprising an IMDQ-PEG-CHOL compound described herein and an antigen of interest elicits 50% to 75% higher immune cell (e.g., T cell, B cell, and/or dendritic cell) recruitment in a subject relative to the immune cell (e.g., T cell, B cell, and/or dendritic cell) recruitment elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art. In some embodiments, an immunogenic composition comprising an IMDQ-PEG-CHOL compound described herein and an antigen of interest elicits at least 5%, at least 10%, at least 15%, at least 20%, or at least 25% higher immune cell (e.g., T cell, B cell, and/or dendritic cell) recruitment in a subject relative to the immune cell (e.g., T cell, B cell, and/or dendritic cell) recruitment elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art. In certain embodiments, an immunogenic composition comprising an IMDQ-PEG-CHOL compound described herein and an antigen of interest elicits at least 30%, at least 35%, at least 40%, at least 45%, or at least 50% higher immune cell (e.g., T cell, B cell, and/or dendritic cell) recruitment in a subject relative to the immune cell (e.g., T cell, B cell, and/or dendritic cell) recruitment elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art. In some embodiments, an immunogenic composition comprising an IMDQ-PEG-CHOL compound described herein and an antigen of interest elicits at least 55%, at least 60%, at least 65%, at least 70%, or at least 75% higher immune cell (e.g., T cell, B cell, and/or dendritic cell) recruitment in a subject relative to the immune cell (e.g., T cell, B cell, and/or dendritic cell) recruitment elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art.

In a specific embodiment, an immunogenic composition comprising an IMDQ-PEG-CHOL compound described herein and an antigen of interest elicits enhanced immune cell (e.g., T cell, B cell, and/or dendritic cell) activation in a subject relative to the immune cell (e.g., T cell, B cell, and/or dendritic cell) activation elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art. In certain embodiments, an immunogenic composition comprising an IMDQ-PEG-CHOL compound described herein and an antigen of interest elicits 5% to 50% higher immune cell (e.g., T cell, B cell, and/or dendritic cell) activation in a subject relative to the immune cell (e.g., T cell, B cell, and/or dendritic cell) activation elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art. In some embodiments, an immunogenic composition comprising an IMDQ-PEG-CHOL compound described herein and an antigen of interest elicits 25% to 50% higher immune cell (e.g., T cell, B cell, and/or dendritic cell) activation in a subject relative to the immune cell (e.g., T cell, B cell, and/or dendritic cell) activation elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art. In certain embodiments, an immunogenic composition comprising an IMDQ-PEG-CHOL compound described herein and an antigen of interest elicits 50% to 75% higher immune cell (e.g., T cell, B cell, and/or dendritic cell) activation in a subject relative to the immune cell (e.g., T cell, B cell, and/or dendritic cell) activation elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art. In some embodiments, an immunogenic composition comprising an IMDQ-PEG-CHOL compound described herein and an antigen of interest elicits at least 5%, at least 10%, at least 15%, at least 20%, or at least 25% higher immune cell (e.g., T cell, B cell, and/or dendritic cell) activation in a subject relative to the immune cell (e.g., T cell, B cell, and/or dendritic cell) activation elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art. In certain embodiments, an immunogenic composition comprising an IMDQ-PEG-CHOL compound described herein and an antigen of interest elicits at least 30%, at least 35%, at least 40%, at least 45%, or at least 50% higher immune cell (e.g., T cell, B cell, and/or dendritic cell) activation in a subject relative to the immune cell (e.g., T cell, B cell, and/or dendritic cell) activation elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art. In some embodiments, an immunogenic composition comprising an IMDQ-PEG-CHOL compound described herein and an antigen of interest elicits at least 55%, at least 60%, at least 65%, at least 70%, or at least 75% higher immune cell (e.g., T cell, B cell, and/or dendritic cell) activation in a subject relative to the immune cell (e.g., T cell, B cell, and/or dendritic cell) activation elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art.

In a specific embodiment, an immunogenic composition comprising an IMDQ-PEG-CHOL compound described herein and an antigen of interest elicits enhanced antibody response in a subject relative to the antibody response elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art. In certain embodiments, an immunogenic composition comprising an IMDQ-PEG-CHOL compound described herein and an antigen of interest elicits 5% to 50% higher antibody response in a subject relative to the antibody response elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art. In some embodiments, an immunogenic composition comprising an IMDQ-PEG-CHOL compound described herein and an antigen of interest elicits 25% to 50% higher antibody response in a subject relative to the antibody response elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art. In certain embodiments, an immunogenic composition comprising an IMDQ-PEG-CHOL compound described herein and an antigen of interest elicits 50% to 75% higher antibody response in a subject relative to the antibody response elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art. In some embodiments, an immunogenic composition comprising an IMDQ-PEG-CHOL compound described herein and an antigen of interest elicits at least 5%, at least 10%, at least 15%, at least 20%, or at least 25% higher antibody response in a subject relative to the antibody response elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art. In certain embodiments, an immunogenic composition comprising an IMDQ-PEG-CHOL compound described herein and an antigen of interest elicits at least 30%, at least 35%, at least 40%, at least 45%, or at least 50% higher antibody response in a subject relative to the antibody response elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art. In some embodiments, an immunogenic composition comprising an IMDQ-PEG-CHOL compound described herein and an antigen of interest elicits at least 55%, at least 60%, at least 65%, at least 70%, or at least 75% higher antibody response in a subject relative to the antibody response elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art.

In certain embodiments, an immunogenic composition comprising an IMDQ-PEG-CHOL compound described herein and an antigen of interest elicits at least 2-fold higher geometric mean concentration (GMC) or geometric mean titer (GMT) of antibody (e.g., IgG) in a subject relative to the GMC or GMT of antibody elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art. In some embodiments, an immunogenic composition comprising an IMDQ-PEG-CHOL compound described herein and an antigen of interest elicits at least 5-fold higher GMC or GMT of antibody (e.g., IgG) in a subject relative to the GMC or GMT of antibody elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art. In certain embodiments, an immunogenic composition comprising an IMDQ-PEG-CHOL compound described herein and an antigen of interest elicits at least 10-fold higher GMC or GMT of antibody (e.g., IgG) in a subject relative to the GMC or GMT of antibody elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art. In some embodiments, an immunogenic composition comprising an IMDQ-PEG-CHOL compound described herein and an antigen of interest elicits at least 15-fold higher GMC or GMT of antibody (e.g., IgG) in a subject relative to the GMC or GMT of antibody elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art. In certain embodiments, an immunogenic composition comprising an IMDQ-PEG-CHOL compound described herein and an antigen of interest elicits at least 20-fold higher GMC or GMT of antibody (e.g., IgG) in a subject relative to the GMC or GMT of antibody elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art. In some embodiments, an immunogenic composition comprising an IMDQ-PEG-CHOL compound described herein and an antigen of interest elicits at least 25-fold higher GMC or GMT of antibody (e.g., IgG) in a subject relative to the GMC or GMT of antibody elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art.

In a specific embodiment, an immunogenic composition comprising an IMDQ-PEG-CHOL compound described herein and an antigen of interest elicits enhanced neutralizing antibody levels relative to the neutralizing antibody levels elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art. In certain embodiments, an immunogenic composition comprising an IMDQ-PEG-CHOL compound described herein and an antigen of interest elicits 5% to 50% higher concentration of neutralizing antibodies in a subject relative to the concentration of neutralizing antibodies elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art. In some embodiments, an immunogenic composition comprising an IMDQ-PEG-CHOL compound described herein and an antigen of interest elicits 25% to 50% higher concentration of neutralizing antibodies in a subject relative to the concentration of neutralizing antibodies elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art. In certain embodiments, an immunogenic composition comprising an IMDQ-PEG-CHOL compound described herein and an antigen of interest elicits 50% to 75% higher concentration of neutralizing antibodies in a subject relative to the concentration of neutralizing antibodies elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art. In some embodiments, an immunogenic composition comprising an IMDQ-PEG-CHOL compound described herein and an antigen of interest elicits at least 5%, at least 10%, at least 15%, at least 20%, or at least 25% higher concentration of neutralizing antibodies in a subject relative to the concentration of neutralizing antibodies elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art. In certain embodiments, an immunogenic composition comprising an IMDQ-PEG-CHOL compound described herein and an antigen of interest elicits at least 30%, at least 35%, at least 40%, at least 45%, or at least 50% higher concentration of neutralizing antibodies in a subject relative to the concentration of neutralizing antibodies elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art. In some embodiments, an immunogenic composition comprising an IMDQ-PEG-CHOL compound described herein and an antigen of interest elicits at least 55%, at least 60%, at least 65%, at least 70%, or at least 75% higher concentration of neutralizing antibodies in a subject relative to the concentration of neutralizing antibodies elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art.

In certain embodiments, an immunogenic composition comprising an IMDQ-PEG-CHOL compound described herein and an antigen of interest elicits at least 2-fold higher geometric mean concentration (GMC) or geometric mean titer (GMT) of neutralizing antibody (e.g., IgG) in a subject relative to the GMC or GMT of neutralizing antibody elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art. In some embodiments, an immunogenic composition comprising an IMDQ-PEG-CHOL compound described herein and an antigen of interest elicits at least 5-fold higher GMC or GMT of neutralizing antibody (e.g., IgG) in a subject relative to the GMC or GMT of neutralizing antibody elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art. In certain embodiments, an immunogenic composition comprising an IMDQ-PEG-CHOL compound described herein and an antigen of interest elicits at least 10-fold higher GMC or GMT of neutralizing antibody (e.g., IgG) in a subject relative to the GMC or GMT of neutralizing antibody elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art. In some embodiments, an immunogenic composition comprising an IMDQ-PEG-CHOL compound described herein and an antigen of interest elicits at least 15-fold higher GMC or GMT of neutralizing antibody (e.g., IgG) in a subject relative to the GMC or GMT of neutralizing antibody elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art. In certain embodiments, an immunogenic composition comprising an IMDQ-PEG-CHOL compound described herein and an antigen of interest elicits at least 20-fold higher GMC or GMT of neutralizing antibody (e.g., IgG) in a subject relative to the GMC or GMT of neutralizing antibody elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art. In some embodiments, an immunogenic composition comprising an IMDQ-PEG-CHOL compound described herein and an antigen of interest elicits at least 25-fold higher GMC or GMT of neutralizing antibody (e.g., IgG) in a subject relative to the GMC or GMT of neutralizing antibody elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art.

In a specific embodiment, an immunogenic composition comprising an IMDQ-PEG-CHOL compound described herein and an antigen of interest the alters the antibody response elicited relative to the antibody response elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art. For example, in certain embodiments, an immunogenic composition comprising an IMDQ-PEG-CHOL compound described herein and an antigen of interest shifts the concentration of a particular isotype or a particular subtype of antibody relative to the concentration of the particular isotype or particular subtype of antibody elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art. In some embodiments, an immunogenic composition comprising an IMDQ-PEG-CHOL compound described herein and an antigen of interest shifts the concentration of IgG2a and $IgG_1$ relative to the concentration of IgG2a and $IgG_1$ elicited by the same composition lacking the IMDQ-PEG-CHOL compound, or the same composition with IMDQ in place of the IMDQ-PEG-CHOL compound in a subject of the same species (e.g., a subject with a similar background genetically and/or health wise), as assessed by an assay described herein (e.g., an assay described in the Examples), or known to one of skill in the art.

In a specific embodiment, an immunogenic composition comprising an IMDQ-PEG-CHOL compound described herein and an antigen of interest results in enhanced cellular uptake, as assessed in an in vitro assay described herein (e.g., an assay described in the Examples), or known to one of skill in the art, relative to the cellular uptake resulting from the same composition lacking the IMDQ-PEG-CHOL compound, or the same composition with IMDQ in place of the IMDQ-PEG-CHOL compound, as assessed by the same assay. In certain embodiments, an immunogenic composition comprising an IMDQ-PEG-CHOL compound described herein and an antigen of interest elicits 5% to 50% higher cellular uptake, as assessed in an in vitro assay described herein (e.g., an assay described in the Examples), or known to one of skill in the art, relative to the cellular uptake elicited by the same composition lacking the IMDQ-PEG-CHOL compound, or the same composition with IMDQ in place of the IMDQ-PEG-CHOL compound, as assessed by the same assay. In some embodiments, an immunogenic composition comprising an IMDQ-PEG-CHOL compound described herein and an antigen of interest elicits 25% to 50% higher cellular uptake, as assessed in an in vitro assay described herein (e.g., an assay described in the Examples), or known to one of skill in the art, relative to the cellular uptake elicited by the same composition lacking the IMDQ-PEG-CHOL compound, or the same composition with IMDQ in place of the IMDQ-PEG-CHOL compound, as assessed by the same assay. In certain embodiments, an immunogenic composition comprising an IMDQ-PEG-CHOL compound described herein and an antigen of interest elicits 50% to 75% higher cellular uptake, as assessed in an in vitro assay described herein (e.g., an assay described in the Examples), or known to one of skill in the art, relative to the cellular uptake elicited by the same composition lacking the IMDQ-PEG-CHOL compound, or the same composition with IMDQ in place of the IMDQ-PEG-CHOL compound, as assessed by the same assay. In some embodiments, an immunogenic composition comprising an IMDQ-PEG-CHOL compound described herein and an antigen of interest elicits at least 5%, at least 10%, at least 15%, at least 20%, or at least 25% higher cellular uptake, as assessed in an in vitro assay described herein (e.g., an assay described in the Examples), or known to one of skill in the art, relative to the cellular uptake elicited by the same composition lacking the IMDQ-PEG-CHOL compound, or the same composition with IMDQ in place of the IMDQ-PEG-CHOL compound, as assessed by the same assay. In certain embodiments, an immunogenic composition comprising an IMDQ-PEG-CHOL compound described herein and an antigen of interest elicits at least 30%, at least 35%, at least 40%, at least 45%, or at least 50% higher cellular uptake, as assessed in an in vitro assay described herein (e.g., an assay described in the Examples), or known to one of skill in the art, relative to the cellular uptake elicited by the same composition lacking the IMDQ-PEG-CHOL compound, or the same composition with IMDQ in place of the IMDQ-PEG-CHOL compound, as assessed by the same assay. In some embodiments, an immunogenic composition comprising an IMDQ-PEG-CHOL compound described herein and an antigen of interest elicits at least 55%, at least 60%, at least 65%, at least 70%, or at least 75% higher cellular uptake, as assessed in an in vitro assay described herein (e.g., an assay described in the Examples), or known to one of skill in the art, relative to the cellular uptake elicited by the same composition lacking the IMDQ-PEG-CHOL compound, or the same composition with IMDQ in place of the IMDQ-PEG-CHOL compound, as assessed by the same assay.

In a specific embodiment, an immunogenic composition comprising an IMDQ-PEG-CHOL compound described herein and an antigen of interest results in enhanced interferon ("IFN") (e.g., IFN-beta and/or IFN-gamma) production, as assessed in an assay described herein (e.g., an assay described in the Examples), or known to one of skill in the art, relative to the IFN (e.g., IFN-beta and/or IFN-gamma) production resulting from the same composition lacking the IMDQ-PEG-CHOL compound, or the same composition with IMDQ in place of the IMDQ-PEG-CHOL compound, as assessed by the same assay. In certain embodiments, an immunogenic composition comprising an IMDQ-PEG-CHOL compound described herein and an antigen of interest elicits 5% to 50% higher IFN (e.g., IFN-beta and/or IFN-gamma), as assessed in an assay described herein (e.g., an assay described in the Examples), or known to one of skill in the art, relative to the IFN (e.g., IFN-beta and/or IFN-gamma) elicited by the same composition lacking the IMDQ-PEG-CHOL compound, or the same composition with IMDQ in place of the IMDQ-PEG-CHOL compound, as assessed by the same assay. In some embodiments, an immunogenic composition comprising an IMDQ-PEG-CHOL compound described herein and an antigen of interest elicits 25% to 50% higher IFN (e.g., IFN-beta and/or IFN-gamma), as assessed in an assay described herein (e.g., an assay described in the Examples), or known to one of skill in the art, relative to the IFN (e.g., IFN-beta and/or IFN-gamma) elicited by the same composition lacking the IMDQ-PEG-CHOL compound, or the same composition with IMDQ in place of the IMDQ-PEG-CHOL compound, as assessed by the same assay. In certain embodiments, an immunogenic composition comprising an IMDQ-PEG-CHOL compound described herein and an antigen of interest elicits 50% to 75% higher IFN (e.g., IFN-beta and/or IFN-gamma), as assessed in an assay described herein (e.g., an assay described in the Examples), or known to one of skill in the art, relative to the IFN (e.g., IFN-beta) elicited by the same composition lacking the IMDQ-PEG-CHOL compound, or the same composition with IMDQ in place of the IMDQ-PEG-CHOL compound, as assessed by the same assay. In some embodiments, an immunogenic composition comprising an IMDQ-PEG-CHOL compound described herein and an antigen of interest elicits at least 5%, at least 10%, at least 15%, at least 20%, or at least 25% higher IFN (e.g., IFN-beta and/or IFN-gamma), as assessed in an assay described herein (e.g., an assay described in the Examples), or known to one of skill in the art, relative to the IFN (e.g., IFN-beta and/or IFN-gamma) elicited by the same composition lacking the IMDQ-PEG-CHOL compound, or the same composition with IMDQ in place of the IMDQ-PEG-CHOL compound, as assessed by the same assay. In certain embodiments, an immunogenic composition comprising an IMDQ-PEG-CHOL compound described herein and an antigen of interest elicits at least 30%, at least 35%, at least 40%, at least 45%, or at least 50% higher IFN (e.g., IFN-beta and/or IFN-gamma), as assessed in an assay described herein (e.g., an assay described in the Examples), or known to one of skill in the art, relative to the IFN (e.g., IFN-beta and/or IFN-gamma) elicited by the same composition lacking the IMDQ-PEG-CHOL compound, or the same composition with IMDQ in place of the IMDQ-PEG-CHOL compound, as assessed by the same assay. In some embodiments, an immunogenic composition comprising an IMDQ-PEG-CHOL compound described herein and an antigen of interest elicits at least 55%, at least 60%, at least 65%, at least 70%, or at least 75% higher IFN (e.g., IFN-beta and/or IFN-gamma), as assessed in an assay described herein (e.g., an assay described in the Examples), or known to one of skill in the art, relative to the IFN (e.g., IFN-beta and/or IFN-gamma) elicited by the same composition lacking the IMDQ-PEG-CHOL compound, or the same composition with IMDQ in place of the IMDQ-PEG-CHOL compound, as assessed by the same assay.

In a specific embodiment, an immunogenic composition comprising an IMDQ-PEG-CHOL compound described herein and an antigen of interest results in enhanced NF-κB activation, as assessed in an assay described herein (e.g., an assay described in the Examples), or known to one of skill in the art, relative to the NF-κB activation resulting from the same composition lacking the IMDQ-PEG-CHOL compound, or the same composition with IMDQ in place of the IMDQ-PEG-CHOL compound, as assessed by the same assay. In certain embodiments, an immunogenic composition comprising an IMDQ-PEG-CHOL compound described herein and an antigen of interest elicits 5% to 50% higher NF-κB activation, as assessed in an in assay described herein (e.g., an assay described in the Examples), or known to one of skill in the art, relative to the NF-κB activation elicited by the same composition lacking the IMDQ-PEG-CHOL compound, or the same composition with IMDQ in place of the IMDQ-PEG-CHOL compound, as assessed by the same assay. In some embodiments, an immunogenic composition comprising an IMDQ-PEG-CHOL compound described herein and an antigen of interest elicits 25% to 50% higher NF-κB activation, as assessed in an assay described herein (e.g., an assay described in the Examples), or known to one of skill in the art, relative to the NF-κB activation elicited by the same composition lacking the IMDQ-PEG-CHOL compound, or the same composition with IMDQ in place of the IMDQ-PEG-CHOL compound, as assessed by the same assay. In certain embodiments, an immunogenic composition comprising an IMDQ-PEG-CHOL compound described herein and an antigen of interest elicits 50% to 75% higher NF-κB activation, as assessed in an assay described herein (e.g., an assay described in the Examples), or known to one of skill in the art, relative to the NF-κB activation elicited by the same composition lacking the IMDQ-PEG-CHOL compound, or the same composition with IMDQ in place of the IMDQ-PEG-CHOL compound, as assessed by the same assay. In some embodiments, an immunogenic composition comprising an IMDQ-PEG-CHOL compound described herein and an antigen of interest elicits at least 5%, at least 10%, at least 15%, at least 20%, or at least 25% higher NF-κB activation, as assessed in an assay described herein (e.g., an assay described in the Examples), or known to one of skill in the art, relative to the NF-κB activation elicited by the same composition lacking the IMDQ-PEG-CHOL compound, or the same composition with IMDQ in place of the IMDQ-PEG-CHOL compound, as assessed by the same assay. In certain embodiments, an immunogenic composition comprising an IMDQ-PEG-CHOL compound described herein and an antigen of interest elicits at least 30%, at least 35%, at least 40%, at least 45%, or at least 50% higher NF-κB activation, as assessed in an assay described herein (e.g., an assay described in the Examples), or known to one of skill in the art, relative to the NF-κB activation elicited by the same composition lacking the IMDQ-PEG-CHOL compound, or the same composition with IMDQ in place of the IMDQ-PEG-CHOL compound, as assessed by the same assay. In some embodiments, an immunogenic composition comprising an IMDQ-PEG-CHOL compound described herein and an antigen of interest elicits at least 55%, at least 60%, at least 65%, at least 70%, or at least 75% higher NF-κB activation, as assessed in an assay described herein (e.g., an assay described in the Examples), or known to one of skill in the art, relative to the NF-κB activation elicited by the same composition lacking the IMDQ-PEG-CHOL compound, or the same composition with IMDQ in place of the IMDQ-PEG-CHOL compound, as assessed by the same assay.

In a specific embodiment, an immunogenic composition described herein is not cytotoxic as assessed by an assay described herein (e.g., an MTT assay), or known to one of skill in the art. In another specific embodiment, an immunogenic composition described herein results in an increase in immune activity in draining lymphoid tissue(s). In specific embodiments, an immunogenic composition comprising an IMDQ-PEG-CHOL compound described herein and an antigen of interest elicits one, two, three, or more, or all of the effects/properties described in the Examples.

In some embodiments, the administration of an immunogenic composition described herein to a patient prevents the onset of one, two or more symptoms of a disease or disorder (e.g., an infectious disease or cancer). In a specific embodiment, the administration of an immunogenic composition described herein to a subject prevents the onset or development of one, two or more symptoms of a disease or disorder (e.g., infectious disease or cancer), reduces the severity of one, two or more symptoms of a disease or disorder (e.g., infectious disease or cancer), or prevents the onset or development of one, two or more symptoms of a disease or disorder (e.g., infectious disease or cancer) and reduces the severity of one, two or more symptoms of the disease or disorder (e.g., infectious disease or cancer). In certain embodiments, the administration of an immunogenic composition described herein to a subject prevents the spread of an infection. In some embodiments, the administration of an immunogenic composition described herein to a subject prevents hospitalization. In certain embodiments, the administration of an immunogenic composition described herein to a subject reduces the length of hospitalization of a subject.

In some embodiments, the administration of an immunogenic composition described herein to a subject prevents recurring infections.

Symptoms of COVID-19 include congested or runny nose, cough, fever, sore throat, headache, wheezing, rapid or shallow breathing or difficulty breathing, bluish color the skin due to lack of oxygen, chills, muscle pain, loss of taste and/or smell, nausea, vomiting, and diarrhea. Symptoms of influenza virus include fever, coughing, shortness of breath or difficulty breathing, fatigue, sore throat, runny or stuffy nose, muscle pain or body aches, and headache.

In another aspect, an IMDQ-PEG-CHOL compound described herein is administered to a subject to enhance the subject's immune response. In a specific embodiment, a pharmaceutical composition comprising an IMDQ-PEG-CHOL compound described herein is administered to a subject to enhance the subject's immune response to an antigen.

In another aspect, an IMDQ-PEG-CHOL compound described herein is used as an adjuvant in a composition (e.g., a pharmaceutical composition) that is administered in combination with (e.g., prior to, concurrently with, or to subsequent to) an antigen of interest, or an immunogenic composition comprising an antigen of interest. In a specific embodiment, a pharmaceutical composition comprising an IMDQ-PEG-CHOL compound described herein is administered in combination with (e.g., prior to, concurrently with, or to subsequent to) an antigen of interest, or an immunogenic composition comprising an antigen of interest. As used herein, the term "in combination" in the context of the administration of a composition comprising an IMDQ-PEG-CHOL compound described herein, and an immunogenic composition comprising an antigen of interest to a subject does not restrict the order in which compositions are administered to a subject. In certain embodiments, a composition (e.g., a pharmaceutical composition) comprising an IMDQ-PEG-CHOL compound described herein is administered to a subject (e.g., a human subject) concurrently with an antigen of interest, or an immunogenic composition (e.g., a vaccine) comprising an antigen of interest. In some embodiments, a composition (e.g., a pharmaceutical composition) comprising an IMDQ-PEG-CHOL compound described herein is administered to a subject (e.g., a human subject) prior to (e.g., 1-15 minutes, 1 to 30 minutes, 15 to 30 minutes, 1 to 45 minutes, 15 to 45 minutes, 1 to 60 minutes, or 15 to 60 minutes prior to) administration of an antigen of interest, or an immunogenic composition comprising an antigen of interest to the subject. For example, in certain embodiments, a composition comprising an IMDQ-PEG-CHOL compound described herein is administered to a subject (e.g., a human subject) 1 to 60 seconds, 1 to 5 minutes, 1 to 10 minutes, 1 to 15 minutes, or 5 to 15 minutes before the administration of an antigen of interest, or an immunogenic composition (e.g., a vaccine) comprising an antigen of interest to the subject. In some embodiments, a composition (e.g., a pharmaceutical composition) comprising an IMDQ-PEG-CHOL compound described herein is administered to a subject (e.g., a human subject) 1 to 30 minutes, 15 to 30 minutes, 1 to 45 minutes, 15 to 45 minutes, 30 to 45 minutes, 1 to 60 minutes, 15 to 60 minutes, or 30 to 60 minutes before an antigen of interest, or an immunogenic composition (e.g., a vaccine) comprising an antigen of interest is administered to the subject. In certain embodiments, a composition comprising an IMDQ-PEG-CHOL compound described herein is administered to a subject (e.g., a human subject) 1 hour to 2 hours, 1.5 hours to 2 hours, 1 to 3 hours, 2 to 3 hours, 1 to 4 hours, 2 to 4 hours, 3 to 4 hours, 1 to 5 hours, 2 to 5 hours, 1 to 6 hours, or 3 to 6 hours before an antigen of interest, or an immunogenic composition (e.g., a vaccine) comprising an antigen of interest is administered to the subject. In some embodiments, a composition comprising an IMDQ-PEG-CHOL compound described herein is administered to a subject (e.g., a human subject) subsequent to (e.g., 1-15 minutes, 1 to 30 minutes, 15 to 30 minutes, 1 to 45 minutes, 15 to 45 minutes, 1 to 60 minutes, or 15 to 60 minutes subsequent to) the administration of an antigen of interest, or an immunogenic composition comprising an antigen of interest to the subject. For example, in certain embodiments, a composition (e.g., a pharmaceutical composition) comprising an IMDQ-PEG-CHOL compound described herein is administered to a subject (e.g., a human subject) 1 to 60 seconds, 1 to 5 minutes, 1 to 10 minutes, 1 to 15 minutes, or 5 to 15 minutes subsequent to the administration of an antigen of interest, or an immunogenic composition (e.g., a vaccine) comprising an antigen of interest to the subject. In some embodiments, a composition (e.g., a pharmaceutical composition) comprising an IMDQ-PEG-CHOL compound described herein is administered to a subject (e.g., a human subject) 1 to 30 minutes, 15 to 30 minutes, 1 to 45 minutes, 15 to 45 minutes, 30 to 45 minutes, 1 to 60 minutes, 15 to 60 minutes, or 30 to 60 minutes subsequent to the administration of an antigen of interest, or an immunogenic composition (e.g., a vaccine) comprising an antigen of interest to the subject. In certain embodiments, a composition (e.g., a pharmaceutical composition) comprising an IMDQ-PEG-CHOL compound described herein is administered to a subject (e.g., a human subject) 1 hour to 2 hours, 1.5 hours to 2 hours, 1 to 3 hours, 2 to 3 hours, 1 to 4 hours, 2 to 4 hours, 3 to 4 hours, 1 to 5 hours, 2 to 5 hours, 1 to 6 hours, or 3 to 6 hours subsequent to the administration of an antigen of interest, or an immunogenic composition (e.g., a vaccine) comprising an antigen of interest to the subject. The composition (e.g., a pharmaceutical composition) comprising the IMDQ-PEG-CHOL compound and the immunogenic composition comprising an antigen of interest may be administered by the same or different routes of administration. A composition (e.g., a pharmaceutical composition) comprising an IMDQ-PEG-CHOL compound described herein, and an immunogenic composition described herein may be administered by any route. For example, a composition (e.g., a pharmaceutical composition) comprising an IMDQ-PEG-CHOL compound described herein, and an immunogenic composition described herein immunogenic composition may be administered parenterally, intranasally, intradermally, or orally. In certain embodiments, a composition (e.g., a pharmaceutical composition) comprising an IMDQ-PEG-CHOL compound described herein, and an immunogenic composition described herein are administered subcutaneously or intramuscularly. In certain embodiments, a composition (e.g., a pharmaceutical composition) comprising an IMDQ-PEG-CHOL compound and an immunogenic composition comprising an antigen of interest are administered to the same general region as each other (e.g., within about 5 mm, within about 4 mm, within about 3 mm, within about 2 mm, or within about 1 mm of each other) by the same route of administration. As used herein, the term "about" or "approximately" when used in conjunction with a number refers to any number within 1, 5 or 10% of the referenced number. See, e.g., Section 5.3 and the Examples, infra, for antigens of interest. In certain embodiments, the antigen of interest is an infectious disease antigen. In some embodiments, the antigen of interest is an antigen of a pathogen. In certain embodiments, the antigen of interest is viral antigen, a bacterial antigen, a fungal antigen, or a parasitic antigen. In specific embodiments, the antigen is a SARS-CoV-2 antigen, an influenza virus antigen, MERS-CoV antigen, human metapneumovirus antigen, respiratory syncytial virus (RSV) antigen, Lassa virus antigen, Ebola virus antigen, or Nipah virus antigen. The antigen of interest can be, e.g., inactivated virus, a protein antigen, a nucleic acid-based antigen (e.g., an RNA-based antigen), a polysaccharide antigen, or a conjugate (e.g., a polysaccharide-protein conjugate). In certain embodiments, the antigen is a cancer antigen. In a specific embodiment, the cancer antigen is a tumor antigen. The tumor antigen may be a tumor-associated antigen, or a tumor-specific antigen. Examples of tumor antigens include CEA, immature laminin receptor, TAG-72, HPV E6, HPV, E7, BING-4, calcium-activated chloride channel 2, 9D7, Ep-CAM, EphA3, Her2/neu, mesothelin, SAP-1, Survivin, NY-ESO-1/LAGE-1, Melan-A/MART-1, BRCA1/2, MART-2, prostate-specific antigen, and Ras. In a specific embodiment, an antigen of interest is foreign or heterologous to the subject being administered an immunogenic composition. In specific embodiments, the antigen of interest of interest is one described in the Examples, infra.

In a specific embodiment, provided herein is a method for enhancing the immune response to an antigen of interest in a subject, comprising administering to the subject a composition (e.g., a pharmaceutical composition) comprising an IMDQ-PEG-CHOL compound described herein, and an immunogenic composition comprising an antigen of interest to the subject. The composition (e.g., pharmaceutical composition) comprising the compound described herein is administered in combination with (e.g., prior to, concurrently with, or to subsequent to) an antigen of interest, or an immunogenic composition comprising an antigen of interest. In certain embodiments, the immune response achieved by administering the composition comprising the IMDQ-PEG-CHOL compound and the immunogenic composition to a subject is higher relative to the immune response achieved by administering the same immunogenic composition without administration of the composition comprising the IMDQ-PEG-CHOL compound, or by administering the same immunogenic composition with a composition comprising IMDQ, AddaVax, or AddaS03 in place of the IMDQ-PEG-CHOL compound to a subject of the same species (e.g., a subject with a similar background genetically and/or health wise), as assessed by an assay described herein (e.g., an assay described in the Examples), or known to one of skill in the art. In some embodiments, the immune response is at least 10%, at least 20%, at least 25%, at least 30%, at least 40% or at least 50% higher. In some embodiments, the immune response is at least 60%, at least 70%, at least 75%, at least 80%, at least 85%, at least 90% or at least 95% higher. In some embodiments, the humoral immune response is higher. In certain embodiments, the cellular immune response is higher. In some embodiments, the humoral and cellular immune responses are higher.

In another aspect, provided herein is a method of inducing an immune response to an antigen of interest in a subject, comprising administering the subject a composition (e.g., pharmaceutical composition) comprising an IMDQ-PEG-CHOL compound described herein, and an immunogenic composition (e.g., a vaccine) comprising the antigen of interest. See, e.g., Section 5.3 and the Examples, infra, for antigens of interest. In certain embodiments, the composition comprising an IMDQ-PEG-CHOL compound described herein is administered to the subject (e.g., a human subject) concurrently with the immunogenic composition (e.g., a vaccine) comprising the antigen of interest. In some embodiments, the composition comprising an IMDQ-PEG-CHOL compound described herein is administered to a subject (e.g., a human subject) prior to (e.g., 1-15 minutes, 1 to 30 minutes, 15 to 30 minutes, 1 to 45 minutes, 15 to 45 minutes, 1 to 60 minutes, or 15 to 60 minutes prior to) administration the immunogenic composition comprising the antigen of interest to the subject. For example, in certain embodiments, the composition comprising an IMDQ-PEG-CHOL compound described herein is administered to a subject (e.g., a human subject) 1 to 60 seconds, 1 to 5 minutes, 1 to 10 minutes, 1 to 15 minutes, or 5 to 15 minutes before the administration of the immunogenic composition (e.g., a vaccine) comprising the antigen of interest to the subject. In some embodiments, the composition comprising an IMDQ-PEG-CHOL compound described herein is administered to a subject (e.g., a human subject) 1 to 30 minutes, 15 to 30 minutes, 1 to 45 minutes, 15 to 45 minutes, 30 to 45 minutes, 1 to 60 minutes, 15 to 60 minutes, or 30 to 60 minutes before the immunogenic composition (e.g., a vaccine) comprising the antigen of interest is administered to the subject. In certain embodiments, the composition comprising an IMDQ-PEG-CHOL compound described herein is administered to a subject (e.g., a human subject) 1 hour to 2 hours, 1.5 hours to 2 hours, 1 to 3 hours, 2 to 3 hours, 1 to 4 hours, 2 to 4 hours, 3 to 4 hours, 1 to 5 hours, 2 to 5 hours, 1 to 6 hours, or 3 to 6 hours before the immunogenic composition (e.g., a vaccine) comprising the antigen of interest is administered to the subject. In some embodiments, the composition comprising an IMDQ-PEG-CHOL compound described herein is administered to a subject (e.g., a human subject) subsequent to (e.g., 1-15 minutes, 1 to 30 minutes, 15 to 30 minutes, 1 to 45 minutes, 15 to 45 minutes, 1 to 60 minutes, or 15 to 60 minutes subsequent to) the administration of the immunogenic composition comprising the antigen of interest to the subject. For example, in certain embodiments, the composition comprising an IMDQ-PEG-CHOL compound described herein is administered to a subject (e.g., a human subject) 1 to 60 seconds, 1 to 5 minutes, 1 to 10 minutes, 1 to 15 minutes, or 5 to 15 minutes subsequent to the administration of the immunogenic composition (e.g., a vaccine) comprising the antigen of interest to the subject. In some embodiments, the composition comprising an IMDQ-PEG-CHOL compound described herein is administered to a subject (e.g., a human subject) 1 to 30 minutes, 15 to 30 minutes, 1 to 45 minutes, 15 to 45 minutes, 30 to 45 minutes, 1 to 60 minutes, 15 to 60 minutes, or 30 to 60 minutes subsequent to the administration of the immunogenic composition (e.g., a vaccine) comprising the antigen of interest to the subject. In certain embodiments, the composition comprising an IMDQ-PEG-CHOL compound described herein is administered to a subject (e.g., a human subject) 1 hour to 2 hours, 1.5 hours to 2 hours, 1 to 3 hours, 2 to 3 hours, 1 to 4 hours, 2 to 4 hours, 3 to 4 hours, 1 to 5 hours, 2 to 5 hours, 1 to 6 hours, or 3 to 6 hours subsequent to the administration of the immunogenic composition (e.g., a vaccine) comprising the antigen of interest to the subject. The composition (e.g., pharmaceutical composition) comprising the IMDQ-PEG-CHOL compound and the immunogenic composition comprising an antigen of interest may be administered by the same or different routes of administration. A composition (e.g., pharmaceutical composition) comprising an IMDQ-PEG-CHOL compound described herein, and an immunogenic composition described herein may be administered by any route. For example, a composition (e.g., pharmaceutical composition) comprising an IMDQ-PEG-CHOL compound described herein, and an immunogenic composition described herein immunogenic composition may be administered parenterally, intranasally, intradermally, or orally. In certain embodiments, a composition (e.g., pharmaceutical composition) comprising an IMDQ-PEG-CHOL compound described herein, and an immunogenic composition described herein are administered subcutaneously or intramuscularly. In certain embodiments, a composition (e.g., pharmaceutical composition) comprising an IMDQ-PEG-CHOL compound, and an immunogenic composition comprising an antigen of interest are administered to the same general region as each other (e.g., within about 5 mm, within about 4 mm, within about 3 mm, within about 2 mm, or within about 1 mm of each other) by the same route of administration. In certain embodiments, the antigen of interest is an infectious disease antigen. In some embodiments, the antigen of interest is an antigen of a pathogen. In certain embodiments, the antigen of interest is viral antigen, a bacterial antigen, a fungal antigen, or a parasitic antigen. In specific embodiments, the antigen of interest is a SARS-CoV-2 antigen, an influenza virus antigen, MERS-CoV antigen, human metapneumovirus antigen, respiratory syncytial virus (RSV) antigen, Lassa virus antigen, Ebola virus antigen, or Nipah virus antigen. The antigen of interest can be, e.g., inactivated virus, a protein antigen, a nucleic acid-based antigen (e.g., an RNA-based antigen), a polysaccharide antigen, or a conjugate (e.g., a polysaccharide-protein conjugate). In certain embodiments, the antigen of interest is a cancer antigen. In a specific embodiment, the cancer antigen is a tumor antigen. The tumor antigen may be a tumor-associated antigen, or a tumor-specific antigen. Examples of tumor antigens include CEA, Immature laminin receptor, TAG-72, HPV E6, HPV, E7, BING-4, Calcium-activated chloride channel 2, 9D7, Ep-CAM, EphA3, Her2/neu, Mesothelin, SAP-1, Survivin, NY-ESO-1/LAGE-1, Melan-A/MART-1, BRCA1/2, MART-2, and Ras. In a specific embodiment, an antigen of interest is foreign or heterologous to the subject being administered an immunogenic composition. In specific embodiments, the antigen of interest is one described in the Examples, infra. In certain embodiments, an immunogenic composition comprising an antigen of interest is a monovalent composition (e.g., a monovalent vaccine). In other embodiments, an immunogenic composition comprising an antigen of interest is a multi-valent composition (e.g. a multi-valent vaccine).

In a specific embodiment, provided herein is a method of inducing an immune response to SARS-CoV-2 in a subject, comprising administering to the subject a composition (e.g., a pharmaceutical composition) comprising an IMDQ-PEG-CHOL compound described herein, and an immunogenic composition (e.g., a vaccine) a SARS-CoV-2 antigen. The SARS-CoV-2 antigen may be one described herein (e.g., one described in the Examples), or known to one of skill in the art. In another specific embodiment, provided herein is a method of inducing an immune response to influenza virus (e.g., influenza A virus and/or influenza B virus) in a subject, comprising administering to the subject a composition (e.g., a pharmaceutical composition) comprising an IMDQ-PEG-CHOL compound described herein, and an immunogenic composition (e.g., a vaccine) an influenza virus antigen (e.g., an influenza A virus antigen and/or an influenza B virus antigen). The influenza virus antigen may be one described herein (e.g., one described in the Examples), or known to one of skill in the art. The composition (e.g., pharmaceutical composition) comprising the IMDQ-PEG-CHOL compound and the immunogenic composition may be administered by the same or different routes of administration. In certain embodiments, the composition comprising the IMDQ-PEG-CHOL compound and the immunogenic composition are administered to the same general region as each other (e.g., within about 5 mm, within about 4 mm, within about 3 mm, within about 2 mm, or within about 1 mm of each other) by the same route of administration. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for inducing an immune response to RSV in a subject, comprising administering to the subject a composition (e.g., pharmaceutical composition) comprising an IMDQ-PEG-CHOL compound described herein, and an immunogenic composition (e.g., a vaccine) comprising a RSV antigen. The RSV antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for inducing an immune response to MERS-CoV in a subject, comprising administering to the subject a composition (e.g., pharmaceutical composition) comprising an IMDQ-PEG-CHOL compound described herein, and an immunogenic composition (e.g., a vaccine) comprising a MERS-CoV antigen. The MERS-CoV antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for inducing an immune response to hMPV in a subject, comprising administering to the subject a composition (e.g., pharmaceutical composition) comprising an IMDQ-PEG-CHOL compound described herein, and an immunogenic composition (e.g., a vaccine) comprising a hMPV antigen. The hMPV antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for inducing an immune response to Lassa virus in a subject, comprising administering to the subject a composition (e.g., pharmaceutical composition) comprising an IMDQ-PEG-CHOL compound described herein, and an immunogenic composition (e.g., a vaccine) comprising a Lassa virus antigen. The Lassa virus antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for inducing an immune response to Ebola virus in a subject, comprising administering to the subject a composition (e.g., pharmaceutical composition) comprising an IMDQ-PEG-CHOL compound described herein, and an immunogenic composition (e.g., a vaccine) comprising an Ebola virus antigen. The Ebola virus antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for inducing an immune response to Nipah virus in a subject, comprising administering to the subject a composition (e.g., pharmaceutical composition) comprising an IMDQ-PEG-CHOL compound described herein, and an immunogenic composition (e.g., a vaccine) comprising a Nipah virus antigen. The Nipah virus antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for inducing an immune response to *Corynebacterium diphtheriae* in a subject, comprising administering to the subject a composition (e.g., pharmaceutical composition) comprising an IMDQ-PEG-CHOL compound described herein, and an immunogenic composition (e.g., a vaccine) comprising a *Corynebacterium diphtheriae* antigen (e.g., diphtheria toxoid). The *Corynebacterium diphtheriae* antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for inducing an immune response to poliovirus in a subject, comprising administering to the subject a composition (e.g., pharmaceutical composition) comprising an IMDQ-PEG-CHOL compound described herein, and an immunogenic composition (e.g., a vaccine) comprising a poliovirus antigen (e.g., inactivated poliovirus). The poliovirus antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for inducing an immune response to hepatitis A virus in a subject, comprising administering to the subject a composition (e.g., pharmaceutical composition) comprising an IMDQ-PEG-CHOL compound described herein, and an immunogenic composition (e.g., a vaccine) comprising a hepatitis A virus antigen. The hepatitis A virus antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for inducing an immune response to Japanese encephalitis virus in a subject, comprising administering to the subject a composition (e.g., pharmaceutical composition) comprising an IMDQ-PEG-CHOL compound described herein, and an immunogenic composition (e.g., a vaccine) comprising a Japanese Encephalitis virus antigen. The Japanese Encephalitis virus antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for inducing an immune response to *Haemophilus influenzae* in a subject, comprising administering to the subject a composition (e.g., pharmaceutical composition) comprising an IMDQ-PEG-CHOL compound described herein, and an immunogenic composition (e.g., a vaccine) comprising a *Haemophilus influenzae* antigen (e.g. heamophilus b conjugate). The *Haemophilus influenzae* antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for inducing an immune response to *Neisseria meningitides* in a subject, comprising administering to the subject a composition (e.g., pharmaceutical composition) comprising an IMDQ-PEG-CHOL compound described herein, and an immunogenic composition (e.g., a vaccine) comprising a *Neisseria meningitidis* antigen (e.g., meningococcal conjugate). The *Neisseria meningitidis* antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for inducing an immune response to *Streptococcus pneumoniae* in a subject, comprising administering to the subject a composition (e.g., pharmaceutical composition) comprising an IMDQ-PEG-CHOL compound described herein, and an immunogenic composition (e.g., a vaccine) comprising a pneumococcal antigen (e.g., a polysaccharide or pneumococcal conjugate). The pneumococcal antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for inducing an immune response to *Bordetella pertussis* in a subject, comprising administering to the subject a composition (e.g., pharmaceutical composition) comprising an IMDQ-PEG-CHOL compound described herein, and an immunogenic composition (e.g., a vaccine) comprising a *Bordetella pertussis* antigen. The *Bordetella pertussis* antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for inducing an immune response to *Bacillus* in a subject, comprising administering to the subject a composition (e.g., pharmaceutical composition) comprising an IMDQ-PEG-CHOL compound described herein, and an immunogenic composition (e.g., a vaccine) comprising a *Bacillus* antigen. The *Bacillus* antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for inducing an immune response to *Clostridium tetani* in a subject, comprising administering to the subject a composition (e.g., pharmaceutical composition) comprising an IMDQ-PEG-CHOL compound described herein, and an immunogenic composition (e.g., a vaccine) comprising a *Clostridium tetani* antigen (e.g., tetanus toxoid). The *Clostridium tetani* antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another aspect, provided herein is a method for immunizing a subject against a disease or disorder associated with an antigen, comprising administering the subject a composition (e.g., pharmaceutical composition) comprising an IMDQ-PEG-CHOL compound described herein, and an immunogenic composition (e.g., a vaccine) comprising an antigen of interest. See, e.g., Section 5.3 and the Examples, infra, for antigens of interest. The antigen associated with the disease or disorder may be the same or different than the antigen of interest. For example, the antigen of interest may be a modified form or derivative of an antigen associated with the disease or disorder. In certain embodiments, the composition comprising an IMDQ-PEG-CHOL compound described herein is administered to the subject (e.g., a human subject) concurrently with the immunogenic composition (e.g., a vaccine) comprising the antigen of interest. In some embodiments, the composition comprising an IMDQ-PEG-CHOL compound described herein is administered to a subject (e.g., a human subject) prior to (e.g., 1-15 minutes, 1 to 30 minutes, 15 to 30 minutes, 1 to 45 minutes, 15 to 45 minutes, 1 to 60 minutes, or 15 to 60 minutes prior to) administration the immunogenic composition comprising the antigen of interest to the subject. For example, in certain embodiments, the composition comprising an IMDQ-PEG-CHOL compound described herein is administered to a subject (e.g., a human subject) 1 to 60 seconds, 1 to 5 minutes, 1 to 10 minutes, 1 to 15 minutes, or 5 to 15 minutes before the administration of the immunogenic composition (e.g., a vaccine) comprising the antigen of interest to the subject. In some embodiments, the composition comprising an IMDQ-PEG-CHOL compound described herein is administered to a subject (e.g., a human subject) 1 to 30 minutes, 15 to 30 minutes, 1 to 45 minutes, 15 to 45 minutes, 30 to 45 minutes, 1 to 60 minutes, 15 to 60 minutes, or 30 to 60 minutes before the immunogenic composition (e.g., a vaccine) comprising the antigen of interest is administered to the subject. In certain embodiments, the composition comprising an IMDQ-PEG-CHOL compound described herein is administered to a subject (e.g., a human subject) 1 hour to 2 hours, 1.5 hours to 2 hours, 1 to 3 hours, 2 to 3 hours, 1 to 4 hours, 2 to 4 hours, 3 to 4 hours, 1 to 5 hours, 2 to 5 hours, 1 to 6 hours, or 3 to 6 hours before the immunogenic composition (e.g., a vaccine) comprising the antigen of interest is administered to the subject. In some embodiments, the composition comprising an IMDQ-PEG-CHOL compound described herein is administered to a subject (e.g., a human subject) subsequent to (e.g., 1-15 minutes, 1 to 30 minutes, 15 to 30 minutes, 1 to 45 minutes, 15 to 45 minutes, 1 to 60 minutes, or 15 to 60 minutes subsequent to) the administration of the immunogenic composition comprising the antigen of interest to the subject. For example, in certain embodiments, the composition comprising an IMDQ-PEG-CHOL compound described herein is administered to a subject (e.g., a human subject) 1 to 60 seconds, 1 to 5 minutes, 1 to 10 minutes, 1 to 15 minutes, or 5 to 15 minutes subsequent to the administration of the immunogenic composition (e.g., a vaccine) comprising the antigen of interest to the subject. In some embodiments, the composition comprising an IMDQ-PEG-CHOL compound described herein is administered to a subject (e.g., a human subject) 1 to 30 minutes, 15 to 30 minutes, 1 to 45 minutes, 15 to 45 minutes, 30 to 45 minutes, 1 to 60 minutes, 15 to 60 minutes, or 30 to 60 minutes subsequent to the administration of the immunogenic composition (e.g., a vaccine) comprising the antigen of interest to the subject. In certain embodiments, the composition comprising an IMDQ-PEG-CHOL compound described herein is administered to a subject (e.g., a human subject) 1 hour to 2 hours, 1.5 hours to 2 hours, 1 to 3 hours, 2 to 3 hours, 1 to 4 hours, 2 to 4 hours, 3 to 4 hours, 1 to 5 hours, 2 to 5 hours, 1 to 6 hours, or 3 to 6 hours subsequent to the administration of the immunogenic composition (e.g., a vaccine) comprising the antigen of interest to the subject. The composition comprising the IMDQ-PEG-CHOL compound and the immunogenic composition comprising an antigen of interest may be administered by the same or different routes of administration. A composition (e.g., pharmaceutical composition) comprising an IMDQ-PEG-CHOL compound described herein, and an immunogenic composition described herein may be administered by any route. For example, a composition (e.g., pharmaceutical composition) comprising an IMDQ-PEG-CHOL compound described herein, and an immunogenic composition described herein immunogenic composition may be administered parenterally, intranasally, intradermally, or orally. In certain embodiments, a composition (e.g., pharmaceutical composition) comprising an IMDQ-PEG-CHOL compound described herein, and an immunogenic composition described herein are administered subcutaneously or intramuscularly. In certain embodiments, a composition (e.g., pharmaceutical composition) comprising an IMDQ-PEG-CHOL compound and an immunogenic composition comprising an antigen of interest are administered to the same general region as each other (e.g., within about 5 mm, within about 4 mm, within about 3 mm, within about 2 mm, or within about 1 mm of each other) by the same route of administration. In certain embodiments, the antigen is an infectious disease antigen. In some embodiments, the antigen is an antigen of a pathogen. In certain embodiments, the antigen is viral antigen, a bacterial antigen, a fungal antigen, or a parasitic antigen. In specific embodiments, the antigen is a SARS-CoV-2 antigen, an influenza virus antigen, MERS-CoV antigen, human metapneumovirus antigen, respiratory syncytial virus (RSV) antigen, Lassa virus antigen, Ebola virus antigen, or Nipah virus antigen. The antigen can be, e.g., inactivated virus, a protein antigen, a nucleic acid-based antigen (e.g., an RNA-based antigen), a polysaccharide antigen, or a conjugate (e.g., a polysaccharide-protein conjugate). In certain embodiments, the antigen is a cancer antigen. In a specific embodiment, the cancer antigen is a tumor antigen. The tumor antigen may be a tumor-associated antigen, or a tumor-specific antigen. Examples of tumor antigens include CEA, Immature laminin receptor, TAG-72, HPV E6, HPV, E7, BING-4, Calcium-activated chloride channel 2, 9D7, Ep-CAM, EphA3, Her2/neu, Mesothelin, SAP-1, Survivin, NY-ESO-1/LAGE-1, Melan-A/MART-1, BRCA1/2, MART-2, and Ras. In a specific embodiment, an antigen of interest is foreign or heterologous to the subject being administered an immunogenic composition. In specific embodiments, the antigen of interest is one described in the Examples, infra. In certain embodiments, an immunogenic composition comprising an antigen of interest is a monovalent composition (e.g., a monovalent vaccine). In other embodiments, an immunogenic composition comprising an antigen of interest is a multi-valent composition (e.g. a multi-valent vaccine).

In a specific embodiment, provided herein is a method for immunizing a subject against SARS-CoV-2, comprising administering to the subject a composition (e.g., pharmaceutical composition) comprising an IMDQ-PEG-CHOL compound described herein, and an immunogenic composition (e.g., a vaccine) comprising a SARS-CoV-2 antigen. The SARS-CoV-2 antigen may be one described herein (e.g., one described in the Examples), or known to one of skill in the art. In another specific embodiment, provided herein is a method for immunizing a subject against influenza virus (e.g., influenza A virus and/or influenza B virus), comprising administering to the subject a composition (e.g., pharmaceutical composition) comprising an IMDQ-PEG-CHOL compound described herein, and an immunogenic composition (e.g., a vaccine) comprising an influenza virus antigen (e.g., an influenza A virus antigen and/or an influenza B virus antigen). The influenza virus antigen may be one described herein (e.g., one described in the Examples), or known to one of skill in the art. The composition comprising the IMDQ-PEG-CHOL compound and the immunogenic composition may be administered by the same or different routes of administration. In certain embodiments, the composition comprising the IMDQ-PEG-CHOL compound and the immunogenic composition are administered to the same general region as each other (e.g., within about 5 mm, within about 4 mm, within about 3 mm, within about 2 mm, or within about 1 mm of each other) by the same route of administration. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method of inducing an immune response to a cancer antigen in a subject, comprising administering to the subject a composition (e.g., pharmaceutical composition) comprising an IMDQ-PEG-CHOL compound described herein, and an immunogenic composition (e.g., a vaccine) comprising a cancer antigen. In a specific embodiment, the cancer antigen is a tumor antigen. The tumor antigen may be a tumor-associated antigen, or a tumor-specific antigen. Examples of tumor antigens include CEA, Immature laminin receptor, TAG-72, HPV E6, HPV, E7, BING-4, Calcium-activated chloride channel 2, 9D7, Ep-CAM, EphA3, Her2/neu, Mesothelin, SAP-1, Survivin, NY-ESO-1/LAGE-1, Melan-A/MART-1, BRCA1/2, MART-2, and Ras. The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for immunizing a subject against RSV disease, comprising administering to the subject a composition (e.g., pharmaceutical composition) comprising an IMDQ-PEG-CHOL compound described herein, and an immunogenic composition (e.g., a vaccine) comprising a RSV antigen. The RSV antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for immunizing a subject against Middle East Respiratory Syndrome, comprising administering to the subject a composition (e.g., pharmaceutical composition) comprising an IMDQ-PEG-CHOL compound described herein, and an immunogenic composition (e.g., a vaccine) comprising a MERS-CoV antigen. The MERS-CoV antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for immunizing a subject against hMPV disease, comprising administering to the subject a composition (e.g., pharmaceutical composition) comprising an IMDQ-PEG-CHOL compound described herein, and an immunogenic composition (e.g., a vaccine) comprising a hMPV antigen. The hMPV antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for immunizing a subject against Lassa fever or Lassa hemorrhagic fever, comprising administering to the subject a composition (e.g., pharmaceutical composition) comprising an IMDQ-PEG-CHOL compound described herein, and an immunogenic composition (e.g., a vaccine) comprising a Lassa virus antigen. The Lassa virus antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for immunizing a subject against Ebola virus disease, comprising administering to the subject a composition (e.g., pharmaceutical composition) comprising an IMDQ-PEG-CHOL compound described herein, and an immunogenic composition (e.g., a vaccine) comprising an Ebola virus antigen. The Ebola virus antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for immunizing a subject against Nipah virus disease, comprising administering to the subject a composition (e.g., pharmaceutical composition) comprising an IMDQ-PEG-CHOL compound described herein, and an immunogenic composition (e.g., a vaccine) comprising a Nipah virus antigen. The Nipah virus antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for immunizing a subject against diphtheria, comprising administering to the subject a composition (e.g., pharmaceutical composition) comprising an IMDQ-PEG-CHOL compound described herein, and an immunogenic composition (e.g., a vaccine) comprising a *Corynebacterium diphtheriae* antigen (e.g., diphtheria toxoid). The *Corynebacterium diphtheriae* antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for immunizing a subject against polio, comprising administering to the subject a composition (e.g., pharmaceutical composition) comprising an IMDQ-PEG-CHOL compound described herein, and an immunogenic composition (e.g., a vaccine) comprising a poliovirus antigen (e.g., inactivated poliovirus). The poliovirus antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for immunizing a subject against hepatitis A, comprising administering to the subject a composition (e.g., pharmaceutical composition) comprising an IMDQ-PEG-CHOL compound described herein, and an immunogenic composition (e.g., a vaccine) comprising a hepatitis A virus antigen. The hepatitis A virus antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for immunizing a subject against Japanese encephalitis, comprising administering to the subject a composition (e.g., pharmaceutical composition) comprising an IMDQ-PEG-CHOL compound described herein, and an immunogenic composition (e.g., a vaccine) comprising a Japanese Encephalitis virus antigen. The Japanese Encephalitis virus antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for immunizing a subject against *Haemophilus influenzae* disease, comprising administering to the subject a composition (e.g., pharmaceutical composition) comprising an IMDQ-PEG-CHOL compound described herein, and an immunogenic composition (e.g., a vaccine) comprising a *Haemophilus influenzae* antigen (e.g. heamophilus b conjugate). The *Haemophilus influenzae* antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for immunizing a subject against meningococcal disease, comprising administering to the subject a composition (e.g., pharmaceutical composition) comprising an IMDQ-PEG-CHOL compound described herein, and an immunogenic composition (e.g., a vaccine) comprising a *Neisseria meningitidis* antigen (e.g., meningococcal conjugate). The *Neisseria meningitidis* antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for immunizing a subject against pneumococcal disease (e.g., invasive pneumococcal disease or otitis media), comprising administering to the subject a composition (e.g., pharmaceutical composition) comprising an IMDQ-PEG-CHOL compound described herein, and an immunogenic composition (e.g., a vaccine) comprising a pneumococcal antigen (e.g., a polysaccharide or pneumococcal conjugate). The pneumococcal antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for immunizing a subject against pertussis, comprising administering to the subject a composition (e.g., pharmaceutical composition) comprising an IMDQ-PEG-CHOL compound described herein, and an immunogenic composition (e.g., a vaccine) comprising a *Bordetella pertussis* antigen. The *Bordetella pertussis* antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for immunizing a subject against anthrax, comprising administering to the subject a composition (e.g., pharmaceutical composition) comprising an IMDQ-PEG-CHOL compound described herein, and an immunogenic composition (e.g., a vaccine) comprising a *Bacillus* antigen. The *Bacillus* antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for immunizing a subject against tetanus, comprising administering to the subject a composition (e.g., pharmaceutical composition) comprising an IMDQ-PEG-CHOL compound described herein, and an immunogenic composition (e.g., a vaccine) comprising a *Clostridium tetani* antigen (e.g., tetanus toxoid). The *Clostridium tetani* antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for immunizing a subject against cancer, comprising administering to the subject a composition (e.g., pharmaceutical composition) comprising an IMDQ-PEG-CHOL compound described herein, and an immunogenic composition (e.g., a vaccine) comprising a cancer antigen. In a specific embodiment, the cancer antigen is a tumor antigen. The tumor antigen may be a tumor-associated antigen, or a tumor-specific antigen. Examples of tumor antigens include CEA, immature laminin receptor, TAG-72, HPV E6, HPV, E7, BING-4, calcium-activated chloride channel 2, 9D7, Ep-CAM, EphA3, Her2/neu, Mesothelin, SAP-1, Survivin, NY-ESO-1/LAGE-1, Melan-A/MART-1, BRCA1/2, MART-2, and Ras. In specific embodiments, the cancer antigen is associated with the cancer for which the immunogenic composition is administered to the subject. For example, CEA is associated with colorectal carcinoma, Immature laminin receptor is associated with RCC, TAB-72 is associated with prostate carcinoma, HPV E6 and HPV E7 are associated with cervical carcinoma, BING-4 is associated with melanoma, calcium-activated chloride channel 2 is associated with lung carcinoma, 9D7 is associated with RCC, Ep-CAM is associated with breast carcinoma, mesothelin is associated with ductal pancreatic carcinoma, SAP-1 is associated with colorectal carcinoma, Melan-A/MART-1 is associated with melanoma, BRCA1/2 is associated with breast and ovarian carcinoma, MART-2 is associated with melanoma, and prostate-specific antigen is associated with prostate cancer. In another example, EphA3, Her2/neu, Survivin, NY-ESO-1/LAGE-1, and Ras are associated with multiple cancers.

In another aspect, provided herein is a method for preventing, treating, or preventing and treating a disease or disorder associated with an antigen, comprising administering the subject a (e.g., pharmaceutical composition) comprising an IMDQ-PEG-CHOL compound described herein, and an immunogenic composition (e.g., a vaccine) comprising an antigen of interest. In a specific embodiment, provided herein is a method for preventing a disease or disorder associated with an antigen, comprising administering the subject a (e.g., pharmaceutical composition) comprising an IMDQ-PEG-CHOL compound described herein, and an immunogenic composition (e.g., a vaccine) comprising an antigen of interest. In another specific embodiment, provided herein is a method for treating a disease or disorder associated with an antigen, comprising administering the subject a (e.g., pharmaceutical composition) comprising an IMDQ-PEG-CHOL compound described herein, and an immunogenic composition (e.g., a vaccine) comprising an antigen of interest. The antigen associated with the disease or disorder may be the same or different than the antigen of interest. For example, the antigen of interest may be a modified form of an antigen associated with the disease or disorder. In certain embodiments, the composition comprising an IMDQ-PEG-CHOL compound described herein is administered to the subject (e.g., a human subject) concurrently with the immunogenic composition (e.g., a vaccine) comprising the antigen of interest. In some embodiments, the composition comprising an IMDQ-PEG-CHOL compound described herein is administered to a subject (e.g., a human subject) prior to (e.g., 1-15 minutes, 1 to 30 minutes, 15 to 30 minutes, 1 to 45 minutes, 15 to 45 minutes, 1 to 60 minutes, or 15 to 60 minutes prior to) administration the immunogenic composition comprising the antigen of interest to the subject. For example, in certain embodiments, the composition comprising an IMDQ-PEG-CHOL compound described herein is administered to a subject (e.g., a human subject) 1 to 60 seconds, 1 to 5 minutes, 1 to 10 minutes, 1 to 15 minutes, or 5 to 15 minutes before the administration of the immunogenic composition (e.g., a vaccine) comprising the antigen of interest to the subject. In some embodiments, the composition comprising an IMDQ-PEG-CHOL compound described herein is administered to a subject (e.g., a human subject) 1 to 30 minutes, 15 to 30 minutes, 1 to 45 minutes, 15 to 45 minutes, 30 to 45 minutes, 1 to 60 minutes, 15 to 60 minutes, or 30 to 60 minutes before the immunogenic composition (e.g., a vaccine) comprising the antigen of interest is administered to the subject. In certain embodiments, the composition comprising an IMDQ-PEG-CHOL compound described herein is administered to a subject (e.g., a human subject) 1 hour to 2 hours, 1.5 hours to 2 hours, 1 to 3 hours, 2 to 3 hours, 1 to 4 hours, 2 to 4 hours, 3 to 4 hours, 1 to 5 hours, 2 to 5 hours, 1 to 6 hours, or 3 to 6 hours before the immunogenic composition (e.g., a vaccine) comprising the antigen of interest is administered to the subject. In some embodiments, the composition comprising an IMDQ-PEG-CHOL compound described herein is administered to a subject (e.g., a human subject) subsequent to (e.g., 1-15 minutes, 1 to 30 minutes, 15 to 30 minutes, 1 to 45 minutes, 15 to 45 minutes, 1 to 60 minutes, or 15 to 60 minutes subsequent to) the administration of the immunogenic composition comprising the antigen of interest to the subject. For example, in certain embodiments, the composition comprising an IMDQ-PEG-CHOL compound described herein is administered to a subject (e.g., a human subject) 1 to 60 seconds, 1 to 5 minutes, 1 to 10 minutes, 1 to 15 minutes, or 5 to 15 minutes subsequent to the administration of the immunogenic composition (e.g., a vaccine) comprising the antigen of interest to the subject. In some embodiments, the composition comprising an IMDQ-PEG-CHOL compound described herein is administered to a subject (e.g., a human subject) 1 to 30 minutes, 15 to 30 minutes, 1 to 45 minutes, 15 to 45 minutes, 30 to 45 minutes, 1 to 60 minutes, 15 to 60 minutes, or 30 to 60 minutes subsequent to the administration of the immunogenic composition (e.g., a vaccine) comprising the antigen of interest to the subject. In certain embodiments, the composition comprising an IMDQ-PEG-CHOL compound described herein is administered to a subject (e.g., a human subject) 1 hour to 2 hours, 1.5 hours to 2 hours, 1 to 3 hours, 2 to 3 hours, 1 to 4 hours, 2 to 4 hours, 3 to 4 hours, 1 to 5 hours, 2 to 5 hours, 1 to 6 hours, or 3 to 6 hours subsequent to the administration of the immunogenic composition (e.g., a vaccine) comprising the antigen of interest to the subject. The composition (e.g., pharmaceutical composition) comprising the IMDQ-PEG-CHOL compound and the immunogenic composition comprising an antigen of interest may be administered by the same or different routes of administration. A composition (e.g., pharmaceutical composition) comprising an IMDQ-PEG-CHOL compound described herein, and an immunogenic composition described herein may be administered by any route. For example, a composition (e.g., pharmaceutical composition) comprising an IMDQ-PEG-CHOL compound described herein, and an immunogenic composition described herein immunogenic composition may be administered parenterally, intranasally, intradermally, or orally. In certain embodiments, a composition (e.g., pharmaceutical composition) comprising an IMDQ-PEG-CHOL compound described herein, and an immunogenic composition described herein are administered subcutaneously or intramuscularly. In certain embodiments, the composition comprising the IMDQ-PEG-CHOL compound and the immunogenic composition comprising an antigen of interest are administered to the same general region as each other (e.g., within about 5 mm, within about 4 mm, within about 3 mm, within about 2 mm, or within about 1 mm of each other) by the same route of administration. In certain embodiments, the antigen is an infectious disease antigen. In some embodiments, the antigen is an antigen of a pathogen. In certain embodiments, the antigen is viral antigen, a bacterial antigen, a fungal antigen, or a parasitic antigen. In specific embodiments, the antigen is a SARS-CoV-2 antigen, an influenza virus antigen, MERS-CoV antigen, human metapneumovirus antigen, respiratory syncytial virus (RSV) antigen, Lassa virus antigen, Ebola virus antigen, or Nipah virus antigen. The antigen can be, e.g., inactivated virus, a protein antigen, a nucleic acid-based antigen (e.g., an RNA-based antigen), a polysaccharide antigen, or a conjugate (e.g., a polysaccharide-protein conjugate). In certain embodiments, the antigen is a cancer antigen. In a specific embodiment, the cancer antigen is a tumor antigen. The tumor antigen may be a tumor-associated antigen, or a tumor-specific antigen. Examples of tumor antigens include CEA, immature laminin receptor, TAG-72, HPV E6, HPV, E7, BING-4, calcium-activated chloride channel 2, 9D7, Ep-CAM, EphA3, Her2/neu, Mesothelin, SAP-1, Survivin, NY-ESO-1/LAGE-1, Melan-A/MART-1, BRCA1/2, MART-2, and Ras. In a specific embodiment, an antigen of interest is foreign or heterologous to the subject being administered an immunogenic composition. In specific embodiments, the antigen of interest is one described in the Examples, infra. In certain embodiments, an immunogenic composition comprising an antigen of interest is a monovalent composition (e.g., a monovalent vaccine). In other embodiments, an immunogenic composition comprising an antigen of interest is a multi-valent composition (e.g. a multi-valent vaccine).

In a specific embodiment, provided herein is a method for preventing COVID-19 in a subject, comprising administering to the subject a composition (e.g., a pharmaceutical composition) comprising an IMDQ-PEG-CHOL compound described herein, and an immunogenic composition (e.g., a vaccine) comprising a SARS-CoV-2 antigen. The SARS-CoV-2 antigen may be one described herein (e.g., one described in the Examples), or known to one of skill in the art. In another specific embodiment, provided herein is a method for preventing influenza virus disease in a subject, comprising administering to the subject a composition (e.g., a pharmaceutical composition) comprising an IMDQ-PEG-CHOL compound described herein, and an immunogenic composition (e.g., a vaccine) comprising an influenza virus antigen (e.g., an influenza A virus antigen and/or an influenza B virus antigen). The influenza virus antigen may be one described herein (e.g., one described in the Examples), or known to one of skill in the art. In a specific embodiment, an antigen of interest is foreign or heterologous to the subject being administered an immunogenic composition. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for preventing RSV disease in a subject, comprising administering to the subject a composition (e.g., pharmaceutical composition) comprising an IMDQ-PEG-CHOL compound described herein, and an immunogenic composition (e.g., a vaccine) comprising a RSV antigen. The RSV antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for preventing Middle East Respiratory Syndrome in a subject, comprising administering to the subject a composition (e.g., pharmaceutical composition) comprising an IMDQ-PEG-CHOL compound described herein, and an immunogenic composition (e.g., a vaccine) comprising a MERS-CoV antigen. The MERS-CoV antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for preventing hMPV disease in a subject, comprising administering to the subject a composition (e.g., pharmaceutical composition) comprising an IMDQ-PEG-CHOL compound described herein, and an immunogenic composition (e.g., a vaccine) comprising a hMPV antigen. The hMPV antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for preventing Lassa fever or Lassa hemorrhagic fever in a subject, comprising administering to the subject a composition (e.g., pharmaceutical composition) comprising an IMDQ-PEG-CHOL compound described herein, and an immunogenic composition (e.g., a vaccine) comprising a Lassa virus antigen. The Lassa virus antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for preventing Ebola virus disease in a subject, comprising administering to the subject a composition (e.g., pharmaceutical composition) comprising an IMDQ-PEG-CHOL compound described herein, and an immunogenic composition (e.g., a vaccine) comprising an Ebola virus antigen. The Ebola virus antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for preventing Nipah virus disease in a subject, comprising administering to the subject a composition (e.g., pharmaceutical composition) comprising an IMDQ-PEG-CHOL compound described herein, and an immunogenic composition (e.g., a vaccine) comprising a Nipah virus antigen. The Nipah virus antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for preventing diphtheria in a subject, comprising administering to the subject a composition (e.g., pharmaceutical composition) comprising an IMDQ-PEG-CHOL compound described herein, and an immunogenic composition (e.g., a vaccine) comprising a *Corynebacterium diphtheriae* antigen (e.g., diphtheria toxoid). The *Corynebacterium diphtheriae* antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for preventing polio in a subject, comprising administering to the subject a composition (e.g., pharmaceutical composition) comprising an IMDQ-PEG-CHOL compound described herein, and an immunogenic composition (e.g., a vaccine) comprising a poliovirus antigen (e.g., inactivated poliovirus). The poliovirus antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for preventing hepatitis A in a subject, comprising administering to the subject a composition (e.g., pharmaceutical composition) comprising an IMDQ-PEG-CHOL compound described herein, and an immunogenic composition (e.g., a vaccine) comprising a hepatitis A virus antigen. The hepatitis A virus antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for preventing Japanese encephalitis in a subject, comprising administering to the subject a composition (e.g., pharmaceutical composition) comprising an IMDQ-PEG-CHOL compound described herein, and an immunogenic composition (e.g., a vaccine) comprising a Japanese Encephalitis virus antigen. The Japanese Encephalitis virus antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for preventing *Haemophilus influenzae* disease in a subject, comprising administering to the subject a composition (e.g., pharmaceutical composition) comprising an IMDQ-PEG-CHOL compound described herein, and an immunogenic composition (e.g., a vaccine) comprising a *Haemophilus influenzae* antigen (e.g. heamophilus b conjugate). The *Haemophilus influenzae* antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for preventing meningococcal disease in a subject, comprising administering to the subject a composition (e.g., pharmaceutical composition) comprising an IMDQ-PEG-CHOL compound described herein, and an immunogenic composition (e.g., a vaccine) comprising a *Neisseria meningitidis* antigen (e.g., meningococcal conjugate). The *Neisseria meningitidis* antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for preventing pneumococcal disease (e.g., invasive pneumococcal disease or otitis media) in a subject, comprising administering to the subject a composition (e.g., pharmaceutical composition) comprising an IMDQ-PEG-CHOL compound described herein, and an immunogenic composition (e.g., a vaccine) comprising a pneumococcal antigen (e.g., a polysaccharide or pneumococcal conjugate). The pneumococcal antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for preventing pertussis in a subject, comprising administering to the subject a composition (e.g., pharmaceutical composition) comprising an IMDQ-PEG-CHOL compound described herein, and an immunogenic composition (e.g., a vaccine) comprising a *Bordetella pertussis* antigen. The *Bordetella pertussis* antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for preventing anthrax in a subject, comprising administering to the subject a composition (e.g., pharmaceutical composition) comprising an IMDQ-PEG-CHOL compound described herein, and an immunogenic composition (e.g., a vaccine) comprising a *Bacillus* antigen. The *Bacillus* antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for preventing tetanus in a subject, comprising administering to the subject a composition (e.g., pharmaceutical composition) comprising an IMDQ-PEG-CHOL compound described herein, and an immunogenic composition (e.g., a vaccine) comprising a *Clostridium tetani* antigen (e.g., tetanus toxoid). The *Clostridium tetani* antigen may be one described herein, or known to one of skill in the art. In certain embodiments, the immunogenic composition is a monovalent composition (e.g., a monovalent vaccine). In other embodiments, the immunogenic composition is a multi-valent composition (e.g. a multi-valent vaccine). The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In another specific embodiment, provided herein is a method for preventing, treating, or preventing and treating cancer in a subject, comprising administering to the subject a composition (e.g., pharmaceutical composition) comprising an IMDQ-PEG-CHOL compound described herein, and an immunogenic composition (e.g., a vaccine) comprising a cancer antigen. In a specific embodiment, the cancer antigen is a tumor antigen. The tumor antigen may be a tumor-associated antigen, or a tumor-specific antigen. Examples of tumor antigens include CEA, immature laminin receptor, TAG-72, HPV E6, HPV, E7, BING-4, calcium-activated chloride channel 2, 9D7, Ep-CAM, EphA3, Her2/neu, mesothelin, SAP-1, Survivin, NY-ESO-1/LAGE-1, Melan-A/MART-1, BRCA1/2, MART-2, prostate-specific antigen, and Ras. In specific embodiments, the cancer antigen is associated with the cancer for which the immunogenic composition is administered to the subject. For example, CEA is associated with colorectal carcinoma, Immature laminin receptor is associated with RCC, TAB-72 is associated with prostate carcinoma, HPV E6 and HPV E7 are associated with cervical carcinoma, BING-4 is associated with melanoma, calcium-activated chloride channel 2 is associated with lung carcinoma, 9D7 is associated with RCC, Ep-CAM is associated with breast carcinoma, mesothelin is associated with ductal pancreatic carcinoma, SAP-1 is associated with colorectal carcinoma, Melan-A/MART-1 is associated with melanoma, BRCA1/2 is associated with breast and ovarian carcinoma, MART-2 is associated with melanoma, and prostate-specific antigen is associated with prostate cancer. In another example, EphA3, Her2/neu, Survivin, NY-ESO-1/LAGE-1, and Ras are associated with multiple cancers. The composition (e.g., pharmaceutical composition) comprising an IMDQ-PEG-CHOL compound described herein may be administered to the subject prior to (e.g., 1 to 15 minutes, 15 to 30 minutes, 30 to 60 minutes, 1 to 5 hours, etc. before), concurrently with, or subsequent to (e.g., 1 to 15 minutes, 15 to 30 minutes, 30 to 60 minutes, 1 to 5 hours, etc. after) the administration of the immunogenic composition to the subject. The composition (e.g., pharmaceutical composition) comprising an IMDQ-PEG-CHOL compound described herein and the immunogenic composition may be administered by the same or different routes of administration.

In a specific embodiment, the administration of a composition comprising an IMDQ-PEG-CHOL compound described herein to a subject in combination (e.g., prior to, concurrently with, or subsequent to) with the administration of an immunogenic composition comprising an antigen of interest elicits a higher antigen-specific immune response in a subject relative to the antigen-specific immune response elicited by the administration of the same immunogenic composition to a subject of the same species (e.g., a subject with a similar background genetically and/or health wise), as assessed by an assay described herein (e.g., an assay described in the Examples), or known to one of skill in the art. In certain embodiments, the administration of a composition comprising an IMDQ-PEG-CHOL compound described herein in combination (e.g., prior to, concurrently with, or subsequent to) with the administration of an immunogenic composition comprising an antigen of interest elicits a 5% to 50% higher antigen-specific immune response in a subject relative to the antigen-specific immune response elicited by administration of the same immunogenic composition to a subject of the same species (e.g., a subject with a similar background genetically and/or health wise), as assessed by an assay described herein (e.g., an assay described in the Examples), or known to one of skill in the art. In some embodiments, the administration of a composition comprising an IMDQ-PEG-CHOL compound described herein in combination (e.g., prior to, concurrently with, or subsequent to) with the administration of an immunogenic composition comprising an antigen of interest elicits a 25% to 50% higher antigen-specific immune response in a subject relative to the antigen-specific immune response elicited by administration of the same immunogenic composition to a subject of the same species (e.g., a subject with a similar background genetically and/or health wise), as assessed by an assay described herein (e.g., an assay described in the Examples), or known to one of skill in the art. In certain embodiments, the administration of a composition comprising an IMDQ-PEG-CHOL compound described herein in combination (e.g., prior to, concurrently with, or subsequent to) with the administration of an immunogenic composition comprising an antigen of interest elicits a 50% to 75% higher antigen-specific immune response in a subject relative to the antigen-specific immune response elicited by administration of the same immunogenic composition to a subject of the same species (e.g., a subject with a similar background genetically and/or health wise), as assessed by an assay described herein (e.g., an assay described in the Examples), or known to one of skill in the art. In some embodiments, the administration of a composition comprising an IMDQ-PEG-CHOL compound described herein in combination (e.g., prior to, concurrently with, or subsequent to) with the administration of an immunogenic composition comprising an antigen of interest elicits at least a 5%, at least a 10%, at least a 15%, at least a 20%, or at least a 25% higher antigen-specific immune response in a subject relative to the antigen-specific immune response elicited by administration of the same immunogenic composition to a subject of the same species (e.g., a subject with a similar background genetically and/or health wise), as assessed by an assay described herein (e.g., an assay described in the Examples), or known to one of skill in the art. In certain embodiments, the administration of a composition comprising an IMDQ-PEG-CHOL compound described herein in combination (e.g., prior to, concurrently with, or subsequent to) with the administration of an immunogenic composition comprising an antigen of interest elicits at least a 25%, at least a 30%, at least a 35%, at least a 40%, at least a 45%, or at least a 50% higher antigen-specific immune response in a subject relative to the antigen-specific immune response elicited by administration of the same immunogenic composition to a subject of the same species (e.g., a subject with a similar background genetically and/or health wise), as assessed by an assay described herein (e.g., an assay described in the Examples), or known to one of skill in the art. In some embodiments, the administration of a composition comprising an IMDQ-PEG-CHOL compound described herein in combination (e.g., prior to, concurrently with, or subsequent to) with the administration of an immunogenic composition comprising an antigen of interest elicits at least a 55%, at least a 60%, at least a 65%, at least a 70%, or at least a 75% higher antigen-specific immune response in a subject relative to the antigen-specific immune response elicited by administration of the same immunogenic composition to a subject of the same species (e.g., a subject with a similar background genetically and/or health wise), as assessed by an assay described herein (e.g., an assay described in the Examples), or known to one of skill in the art.

In some embodiments, the administration of a composition comprising an IMDQ-PEG-CHOL compound described herein in combination with the administration of an immunogenic composition described herein to a patient to prevent the onset of one, two or more symptoms of a disease or disorder (e.g., an infectious disease or cancer). In a specific embodiment, the administration of a composition comprising an IMDQ-PEG-CHOL compound described herein in combination with the administration of an immunogenic composition described herein to a subject prevents the onset or development of one, two or more symptoms of a disease or disorder (e.g., infectious disease or cancer), reduces the severity of one, two or more symptoms of a disease or disorder (e.g., infectious disease or cancer), or prevents the onset or development of one, two or more symptoms of a disease or disorder (e.g., infectious disease or cancer) and reduces the severity of one, two or more symptoms of the disease or disorder (e.g., infectious disease or cancer). In certain embodiments, the administration of a composition comprising an IMDQ-PEG-CHOL compound described herein in combination with the administration of an immunogenic composition described herein to a subject prevents the spread of an infection. In some embodiments, the administration of an immunogenic composition described herein to a subject prevents hospitalization. In certain embodiments, the administration of an immunogenic composition described herein to a subject reduces the length of hospitalization of a subject. In some embodiments, the administration of a composition comprising an IMDQ-PEG-CHOL compound described herein in combination with the administration of an immunogenic composition described herein to a subject prevents recurring infections.

In certain embodiments, the amount of an IMDQ-PEG-CHOL compound described herein administered to a subject is 0.1 microgram to 100 micrograms. In certain embodiments, the amount of IMDQ-PEG-CHOL compound described herein, administered to a subject is the same or about the same (e.g., within 1%, 5%, or 10%) as described in the Examples, infra. The amount of an antigen included in an immunogenic composition will vary depending on, e.g., the type of antigen. If the antigen is a protein, the amount administered to the subject may be 1 microgram to 25 grams of the antigen per kilogram of the subject. In some embodiment, if the antigen is a protein, the amount administered to the subject is 1 microgram to 25 grams of the antigen. If the antigen is nucleic-acid based (e.g., mRNA-based), the amount administered to the subject is 0.1 to 1000 micrograms. In certain embodiments, the antigen is one described in the Examples, infra, and the amount of the antigen administered to a subject is the same or about the same (e.g., within 1%, 5%, or 10%) as described in the Examples, infra. In certain embodiments, the amount of IMDQ-PEG-CHOL compound described herein, and/or the amount of antigen administered to a subject is the same or about the same (e.g., within 1%, 5%, or 10%) as described in the Examples, infra.

5.6 Biological Assays

In a specific embodiment, a biological assay known to one of skill in the art to characterize a composition comprising an IMDQ-PEG-CHOL compound described herein, or an immunogenic composition described herein. In specific embodiments, a neutralization assay known to one of skill in the art or described herein is used to assess for antibodies that bind to an antigen. In some embodiments, the ability of anti-antigen antibodies to bind to an antigen of interest may be assessed by any method know to one of skill in the art (e.g., an immunoassay, such as an ELISA, Western Blot, etc.).

5.6.1 In Vitro Viral Assays

Assays that measure replication of a pathogen include those that indirectly measure replication (as determined, e.g., by plaque formation or bacterial colony formation) or the production of a protein(s) of a pathogen (as determined, e.g., by ELISA or Western blot analysis) or an RNA(s) of a pathogen (as determined, e.g., by RT-PCR or Northern blot analysis) in vitro using methods which are well known in the art.

For example, replication of a virus can be assessed by any method known in the art or described herein (e.g., in cell culture (e.g., cultures of chicken embryonic kidney cells or cultures of chicken embryonic fibroblasts (CEF)). Viral titer may be determined by inoculating serial dilutions of a virus into cell cultures (e.g., CEF, MDCK, EFK-2 cells, Vero cells, primary human umbilical vein endothelial cells (HUVEC), H292 human epithelial cell line or HeLa cells), chick embryos, or live animals (e.g., avians). After incubation of the virus for a specified time, the virus is isolated using standard methods. Physical quantitation of the virus titer can be performed using PCR applied to viral supernatants (Quinn & Trevor, 1997; Morgan et al., 1990), hemagglutination assays, tissue culture infectious doses (TCID50) or egg infectious doses (EID50).

Immunofluorescence-based approaches may also be used to detect a pathogen (e.g., virus) and assess growth. Such approaches are well known to those of skill in the art, e.g., fluorescence microscopy and flow cytometry. Methods for flow cytometry, including fluorescence activated cell sorting (FACS), are available (see, e.g., Owens, et al. (1994) *Flow Cytometry Principles for Clinical Laboratory Practice*, John Wiley and Sons, Hoboken, NJ; Givan (2001) *Flow Cytometry*, $2^{nd}$ ed.; Wiley-Liss, Hoboken, NJ; Shapiro (2003) *Practical Flow Cytometry*, John Wiley and Sons, Hoboken, NJ). Fluorescent reagents suitable for modifying nucleic acids, including nucleic acid primers and probes, polypeptides, and antibodies, for use, e.g., as diagnostic reagents, are available (Molecular Probesy (2003) *Catalogue*, Molecular Probes, Inc., Eugene, OR; Sigma-Aldrich (2003) *Catalogue*, St. Louis, MO).

Standard methods of histology of the immune system are described (see, e.g., Muller-Harmelink (ed.) (1986) *Human Thymus: Histopathology and Pathology*, Springer Verlag, New York, NY; Hiatt, et al. (2000) *Color Atlas of Histology*, Lippincott, Williams, and Wilkins, Phila, PA; Louis, et al. (2002) *Basic Histology: Text and Atlas*, McGraw-Hill, New York, NY).

5.6.2 Interferon Assays

IFN induction and release may be determined using techniques known to one of skill in the art. For example, the amount of IFN induced in cells may be determined using an immunoassay (e.g., an ELISA or Western blot assay) to measure IFN expression or to measure the expression of a protein whose expression is induced by IFN. Alternatively, the amount of IFN induced may be measured at the RNA level by assays, such as Northern blots and quantitative RT-PCR, known to one of skill in the art. In specific embodiments, the amount of IFN released may be measured using an ELISPOT assay. Further, the induction and release of cytokines and/or interferon-stimulated genes may be determined by, e.g., an immunoassay or ELISPOT assay at the protein level and/or quantitative RT-PCR or northern blots at the RNA level.

5.6.3 Activation Marker Assays and Immune Cell Infiltration Assay

Techniques for assessing the expression of T cell marker, B cell marker, activation marker, co-stimulatory molecule, ligand, or inhibitory molecule by immune cells are known to one of skill in the art. For example, the expression of T cell marker, B cell marker, an activation marker, co-stimulatory molecule, ligand, or inhibitory molecule by an immune cell can be assessed by flow cytometry.

5.6.4 Toxicity Studies

In some embodiments, a composition comprising an IMDQ-PEG-CHOL compound described herein, or an immunogenic composition described herein is tested for cytotoxicity in mammalian, preferably human, cell lines. In certain embodiments, cytotoxicity is assessed in one or more of the following non-limiting examples of cell lines: U937, a human monocyte cell line; primary peripheral blood mononuclear cells (PBMC); Huh7, a human hepatoblastoma cell line; HL60 cells, HT1080, HEK 293T and 293H, MLPC cells, human embryonic kidney cell lines; human melanoma cell lines, such as SkMel2, SkMel-119 and SkMel-197; THP-1, monocytic cells; a HeLa cell line; and neuroblastoma cells lines, such as MC-IXC, SK-N-MC, SK-N-MC, SK-N-DZ, SH-SY5Y, and BE(2)-C. In some embodiments, the ToxLite assay is used to assess cytotoxicity. In some embodiments, an MTT assay, such as described in Section 6, infra, is used to assess cytotoxicity.

Many assays well-known in the art can be used to assess viability of cells or cell lines. For example, cell proliferation can be assayed by measuring Bromodeoxyuridine (BrdU) incorporation, (3H) thymidine incorporation, by direct cell count, or by detecting changes in transcription, translation or activity of known genes such as proto-oncogenes (e.g., fos, myc) or cell cycle markers (Rb, cdc2, cyclin A, D1, D2, D3, E, etc.). The levels of such protein and mRNA and activity can be determined by any method well known in the art. For example, protein can be quantitated by known immunodiagnostic methods such as ELISA, Western blotting or immunoprecipitation using antibodies, including commercially available antibodies. mRNA can be quantitated using methods that are well known and routine in the art, for example, using Northern analysis, RNase protection, or polymerase chain reaction in connection with reverse transcription. Cell viability can be assessed by using trypan-blue staining or other cell death or viability markers known in the art. In a specific embodiment, the level of cellular ATP is measured to determined cell viability. In specific embodiments, a composition comprising an IMDQ-PEG-CHOL compound described herein, or an immunogenic composition described herein does not kill healthy (i.e., non-cancerous) cells.

In specific embodiments, cell viability may be measured in three-day and seven-day periods using an assay standard in the art, such as the CellTiter-Glo Assay Kit (Promega) which measures levels of intracellular ATP. A reduction in cellular ATP is indicative of a cytotoxic effect. In another specific embodiment, cell viability can be measured in the neutral red uptake assay. In other embodiments, visual observation for morphological changes may include enlargement, granularity, cells with ragged edges, a filmy appearance, rounding, detachment from the surface of the well, or other changes.

A composition comprising an IMDQ-PEG-CHOL compound described herein, or an immunogenic composition described herein can be tested for in vivo toxicity in animal models. The toxicity, efficacy or both of a composition comprising an IMDQ-PEG-CHOL compound described herein, or an immunogenic composition described herein can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Therapies that exhibit large therapeutic indices are preferred.

5.6.5 Biological Activity Assays

A composition comprising an IMDQ-PEG-CHOL compound described herein, or an immunogenic composition described herein can be tested for biological activity using animal models for inhibiting a disease or disorder (e.g., infectious disease), antibody response to the composition, an immune cell response to the composition, etc. Such animal model systems include, but are not limited to, rats, mice, hamsters, cotton rats, chicken, cows, monkeys (e.g., African green monkey), pigs, dogs, rabbits, etc.

In a specific embodiment, a composition comprising an IMDQ-PEG-CHOL compound described herein, or an immunogenic composition described herein may be tested using animal models for the ability to induce a certain geometric mean titer of antibody(ies) that binds to the antigen. In another specific embodiment, a composition comprising an IMDQ-PEG-CHOL compound described herein, or an immunogenic composition described herein may be tested using animal models for the ability to induce antibodies that have neutralizing activity against an antigen in a neutralization assay. In some embodiments, a composition comprising an IMDQ-PEG-CHOL compound described herein, or an immunogenic composition described herein to induce a certain geometric mean titer of antibody (ies) that binds to the antigen (e.g., SARS-CoV-2 antigen, Ebola virus antigen, MERS-CoV antigen, Lassa virus antigen, RSV antigen, or human metapneumovirus antigen) and neutralizes the pathogen (e.g., virus) associated with the antigen in a microneutralizsation assay.

5.7 Kits

In one aspect, provided herein is a pharmaceutical pack or kit comprising one or more containers filled with an IMDQ-PEG-CHOL compound described herein. In another aspect, provided herein is a pharmaceutical pack or kit comprising one or more containers filled with one, two or more of the ingredients of a composition (e.g., an immunogenic composition) described herein. In a specific embodiment, provided herein is a pharmaceutical pack or kit comprising a container, wherein the container comprises an IMDQ-PEG-CHOL compound described herein, or a composition comprising an IMDQ-PEG-CHOL compound described herein. In certain embodiments, the pharmaceutical pack or kit further comprises a second container comprising an immunogenic composition, wherein the immunogenic composition comprises an antigen of interest. In specific embodiments, provided herein is a pharmaceutical pack or kit comprising a container, wherein the container comprises an immunogenic composition comprising an IMDQ-PEG-CHOL compound described herein and an antigen of interest. Optionally associated with such container(s) can be a notice in the form prescribed by a governmental agency regulating the manufacture, use or sale of pharmaceuticals or biological products, which notice reflects approval by the agency of manufacture, use or sale for human administration.

6. EXAMPLE 1: STERILIZING IMMUNITY AGAINST SARS-COV-2 INFECTION IN MICE BY A SINGLE-SHOT AND MODIFIED IMIDAZOQUINOLINE TLR7/8 AGONIST-ADJUVANTED RECOMBINANT SPIKE PROTEIN VACCINE

The search for vaccines that protect from severe morbidity and mortality as a result of infection with severe acute respiratory syndrome coronavirus 2 (SARS-CoV-2), the virus that causes coronavirus disease 2019 (COVID-19) is a race against the clock and the virus. Several vaccine candidates are currently being tested in the clinic. Due to its involvement in viral entry, the S protein is a major target for current vaccine development against SARS-CoV-2 (5). In this study we explored the recombinant SARS-CoV-2 S protein as a potential vaccine candidate. Inactivated virus and recombinant protein vaccines can be safe options but may require adjuvants to induce robust immune responses efficiently. We and others have reported on strategies to alter the bio-distribution of imidazoquinolines through chemical conjugation to a synthetic carrier that limits systemic circulation but confers robust translocation to immune-inducing sites in sentinel lymph nodes (12-16).

This example describes the use of a novel lipidated imidazoquinoline (IMDQ-PEG-CHOL) TLR7/8 adjuvant to induce a protective immune response against SARS-CoV-2 after single vaccination with trimeric recombinant SARS-CoV-2 Spike protein in the BALB/c mouse model. Inclusion of lipidated IMDQ-PEG-CHOL in the SARS-CoV-2 Spike vaccine formulation resulted in enhanced immune cell recruitment and activation in the draining lymph node. Lipidated IMDQ-PEG-CHOL has a better safety profile compared to control IMDQ as it induces a more localized immune response upon footpad injection, preventing systemic inflammation. Moreover, lipidated IMDQ-PEG-CHOL adjuvanted vaccine induced enhanced ELISA and in vitro microneutralization titers, and a more balanced IgG2a/IgG1 response. To correlate vaccine responses with control of virus replication in vivo, vaccinated mice were challenged with SARS-CoV-2 virus after being sensitized to SARS-CoV-2 infection by intranasal adenovirus-mediated transduction of the human angiotensin converting enzyme 2 (ACE2) gene, the receptor for SARS-CoV-2. Animals vaccinated with trimeric recombinant spike protein vaccine without adjuvant had lung virus titers comparable to non-vaccinated control mice, whereas animals vaccinated with lipidated IMDQ-PEG-CHOL-adjuvanted vaccine controlled viral replication and infectious viruses could not be recovered from their lungs at day 4 postinfection. In order to test whether IMDQ-PEG-CHOL could also be used to adjuvant vaccines currently licensed for use in humans, proof of concept was also provided by using the same lipidated IMDQ-PEG-CHOL to adjuvant human quadrivalent inactivated influenza virus split vaccine, which resulted in enhanced hemagglutination inhibition titers and a more balanced IgG2a/IgG1 antibody response. Enhanced influenza vaccine responses correlated with better virus control when mice were given a lethal influenza virus challenge. These results underscore the potential use of IMDQ-PEG-CHOL as an adjuvant to achieve protection after single immunization with recombinant protein and inactivated vaccines against respiratory viruses, such as SARS-CoV-2 and influenza viruses.

6.1 Materials & Methods

Materials. All chemicals for synthesis were purchased from Sigma-Aldrich or TCI, unless noted otherwise.

Mice, Cell lines and reagents. 6-8 weeks old female BALB/c mice were obtained from Charles River Laboratories, MA and were housed in a specified pathogen-free facility at Icahn school of medicine at Mount Sinai, with food and water ad libitum, adhering to the guidelines from Institutional Animal Care and Use Committee.

Madin-Darby Canine Kidney Cells (MDCK) and Vero-E6 cells are routinely cultured in the laboratory. Both cells were maintained in Dulbecco's Modified Eagle's Medium supplemented with 10% Fetal bovine serum (FBS) and additionally with 1% non-essential amino acids for Vero-E6 cells. DC2.4 mouse dendritic cells were cultured in RPMI-glutamax supplemented with 10% fetal bovine serum (FBS), antibiotics (50 units/mL penicillin and 50 μg/mL streptomycin) and 1 mM sodium pyruvate. Murine RAW blue 264.7 macrophages were cultured in DMEM medium supplemented with 10% heat-inactivated FBS, antibiotics (50 units/mL penicillin and 50 μg/mL streptomycin), 2 mM L-glutamine and 0.01% Zeocin. Cells were incubated at 37° C. in a controlled and sterile environment of 95% relative humidity and 5% $CO_2$.

Vaccines, Blood Collection and Serology.

Quadrivalent inactivated influenza virus vaccine (QIV) was the human Seqirus vaccine (2018-2019 formula) containing the antigens of the following influenza virus strains: A/Singapore/GP1908/2015 IVR-180 (H1N1), A/North Carolina/04/2016 (H3N2), B/Iowa/06/2017 and B/Singapore/INFTT-16-0610/2016. Vaccine was obtained from BEI resources and mixed with adjuvant as described below. Vaccine was injected once via the intramuscular route with a BD 300 μL insulin syringe in the hamstring muscles of the both hind legs (50 μL/leg). The administered vaccine dose corresponds to 1.5 m of each hemagglutinin type in the vaccine per mouse.

Blood was collected twenty days post vaccination via submandibular bleeding and serum was prepared by allowing the blood to clot at room temperature. Anti-HA antibody responses were measured by enhanced luminescent immunosorbent assay (ELISA) and hemagglutination inhibition (HI) assay. For quantification of HA-specific total IgG levels by ELISA, 96 well NUNC Maxisorp plates were coated with QIV (2 μg/ml HA equivalent for each HA) in bicarbonate buffer at 4° C. overnight. After washing and blocking with 4% milk for 1 h at room temperature, serum samples 3-fold diluted starting at 1/100 in PBS with 0.05% Tween20 are allowed to bind ELISA antigen for 1.5 h at room temperature. Plates were washed three times with PBS (0.05% Tween20) and incubated with sheep-derived anti-mouse total IgG (GE Healthcare, Amersham, UK), IgG1 or IgG2a (Invitrogen) serum conjugated to horse-radish peroxidase. After a final washing step, tetramethylbenzidine (TMB) substrate (Sigma-Aldrich, San Diego, CA, USA) was used to estimate levels of HA-specific mouse IgG by measuring the $OD_{450}$ with the $OD_{650}$ as a reference after stopping the colorimetric reaction with 1M $H_2SO_4$.

Hemagglutination inhibition was performed as previously described (20). Briefly, four volumes of receptor destroying enzyme (RDE, *Vibrio cholera* filtrate, Sigma Aldrich, San Diego, CA, USA) were added to each volume of mouse serum. After overnight incubation at 37° C., sera were heat-inactivated at 56° C. for 30 min in citrate buffer. Four hemagglutination units of IVR-180 H1N1 virus were mixed with twofold dilutions of treated sera in a final volume of 50 μL. Mixtures of virus and diluted serum were allowed to bind for 1 h at room temperature before 50 μL of 0.5% chicken red blood cell suspension was added. HI titers were read after 1 h incubation on ice.

Trimeric recombinant SARS-CoV-2 Spike protein was produced as previously described: only the ectodomain of the spike protein (GenBank: MN908947.3) was cloned into a mammalian expression plasmid and the cleavage site was removed and stabilizing prolines were added at position 986 and 987 (21-23). A hexa-histidine tag as well as a T4 foldon trimerization domain was present in the plasmid for ease of purification. The spike protein was expressed in 293F cells, using the ExpiFectamine 293 Transfection Kit (Thermo Fisher). Supernatant was collected on day 3 post transfection and Ni-NTA agarose (Qiagen) was used to purify the protein. This protocol has been described in much greater detail earlier (23). Vaccine (6 μg/mouse) was mixed with adjuvant as described below and injected once via the intramuscular route with a BD 300 μL insulin syringe in the hamstring muscles of both hind legs (50 μL/leg).

Anti-SARS-CoV-2 spike protein ELISA was performed to estimate Spike-specific antibody responses upon vaccination. Briefly, maxisorp Nunc 96-well microtiter plates were coated with 50 μl per well of recombinant spike protein, diluted to a concentration of 2 μg/ml in carbonate/bicarbonate buffer and incubated overnight at 4° C. Three-fold serially diluted serum samples, starting from 1:100, were added to the antigen-coated plates followed by overnight incubation at 4° C. The plates were then washed in 1×PBS+0.01% Tween20 and again incubated with appropriate HRP-conjugated secondary antibodies targeting total IgG, IgG1 or IgG2a antibodies (GE Healthcare, Amersham, UK). The plates were washed and developed with 50 μl of TMB substrate per well until blue color appeared. The reaction was terminated with 50 μl 1M $H_2SO_4$ and the absorbance was measured at 450 nm with 650 nm as a reference.

In-vitro microneutralization assay. To measure the neutralizing potential of SARS-CoV-2 vaccine-induced sera, an in vitro microneutralization assay was performed similar to the protocol described in (24). Briefly, the Spike±adjuvant-vaccinated mice sera were inactivated at 56° C. for 30 min. Serum samples were serially diluted 2-fold starting from 1:10 dilution in infection medium (DMEM+2% FBS+1× non-essential amino acids). The samples were incubated with 100 tissue culture infective dose 50 (TCID50) which equals 40 plaque forming units (PFU) of SARS-CoV2 virus for 1 hour in an incubator at 37° C., 5% $CO_2$ and then transfer on pre-seeded Vero-E6 cells in 96-well cell-culture plates. The plates were incubated at 37° C. for 48 hours and fixed in 4% formaldehyde. The cells were washed with 1×PBS and blocked in 5% milk in 1×PBS+0.1% Tween20 for 1 hour at room temperature. After blocking, the cells were permeabilized with 0.1% TritonX100, washed and incubated with anti-SARS-CoV-2-nucleoprotein and anti-SARS-CoV-2-Spike monoclonal antibodies, mixed in 1:1 ratio, for 1.5 hours at room temperature. The cells were washed again and incubated with HRP-conjugated anti-mouse IgG secondary antibody for 1 hour at room temperature followed by a brief PBS wash. Finally, 50 μl TMB substrate was added and incubated until blue color appeared and the reaction was terminated with 50 μl 1M H2504. Absorbance at 450 nm was recorded and percentage inhibition calculated. Anti-mouse SARS-CoV-2-nucleoprotein and anti-mouse SARS-CoV-2-Spike antibodies were obtained from the Center for Therapeutic Antibody Development at the Icahn School of medicine at Mount Sinai, New York.

Adjuvants: Addavax was purchased from Invivogen and mixed at a 4:1 ratio vaccine:Addavax per the manufacturer's recommendation. IMDQ adjuvants were mixed with vaccine at an equivalent of 10 μg core IMDQ (100 μg of IMDQ-PEG-CHOL, see below) per mouse.

Viruses and Infection. QIV vaccinated mice were infected 24 days post vaccination with 100 lethal dose 50 (18,000 PFU) of egg-grown influenza IVR-180 H1N1 virus, a vaccine strain that contains the surface antigens of influenza A/Singapore/gp1908/2015 (H1N1) virus. Morbidity and mortality were monitored for eight days. A group of age-matched naïve animals was added to the experiment to confirm the dose of virus was lethal to unvaccinated animals.

In order to make SARS-CoV-2 Spike-vaccinated Balb/c mice susceptible to challenge with wild type SARS-CoV-2 virus, airway expression of human ACE-2, the receptor for SARS-CoV-2, was obtained by intranasal transduction of mice with $2.5*10^8$ PFU of adenovirus expressing h-ACE-2 (Ad5-hACE2), 4.5-weeks post-vaccination as described in (25). Five days after transduction with Ad5-hACE2, mice were challenged with $5*10^4$ PFU of SARS-CoV2 isolate USA-WA1/2020 (BEI resources; NR-52281) per mice. Body weights were recorded to assess the morbidity during the days post challenge.

Lung Virus Titration. Plaque assays were performed to quantify and compare the lung viral titers in vaccinated versus unvaccinated mice. As described previously (20), whole lungs were harvested from the mice and homogenized in 1 ml 1×PBS. After brief centrifugation, the tissue debris was discarded and the supernatant was 10-fold serially diluted starting from 1:10 dilution. For IVR-180, MDCK cells were incubated with the lung homogenate dilutions for 1 hour at 37° C., 5% $CO_2$ and then overlaid with a mixture of 2% oxoid agar and 2×MEM supplemented with 1% diethyl-aminoethyl (DEAE)-dextran and 1 μg/ml tosylamide-2-phenylethyl chloro-methyl ketone (TPCK)-treated trypsin. After 48 hours of incubation at 37° C., 5% $CO_2$, the plates were fixed in 4% formaldehyde and immune-stained with IVR-180-post-challenge polyclonal serum. Similarly, For SARS-CoV-2, pre-seeded Vero-E6 cells were incubate with diluted lung homogenates for 1 hour at room temperature and then overlayed with a 1 ml mixture of 2% oxoid agar and 2×MEM supplemented with 2% FBS. After 72 hours of incubation at 37° C., 5% $CO_2$, the plates were fixed in 4% formaldehyde and permeabilized with 0.1% TritonX100, followed by immune-staining of infected cells with anti-mouse SARS-CoV-2-nucleoprotein and anti-mouse SARS-CoV-2-Spike monoclonal antibodies. After incubation in primary antibodies, HRP-conjugated anti-mouse secondary antibody was added for 1 hour. Finally, the plaques were developed with TrueBlue substrate (KPL-Seracare). The final viral titers were calculated in terms of plaque forming units (PFU)/ml.

IMDQ-PEG-CHOL Synthesis.

Scheme 1. Synthesis of IMDQ-PEG-CHOL and Cynanine5-PEG-CHOL.
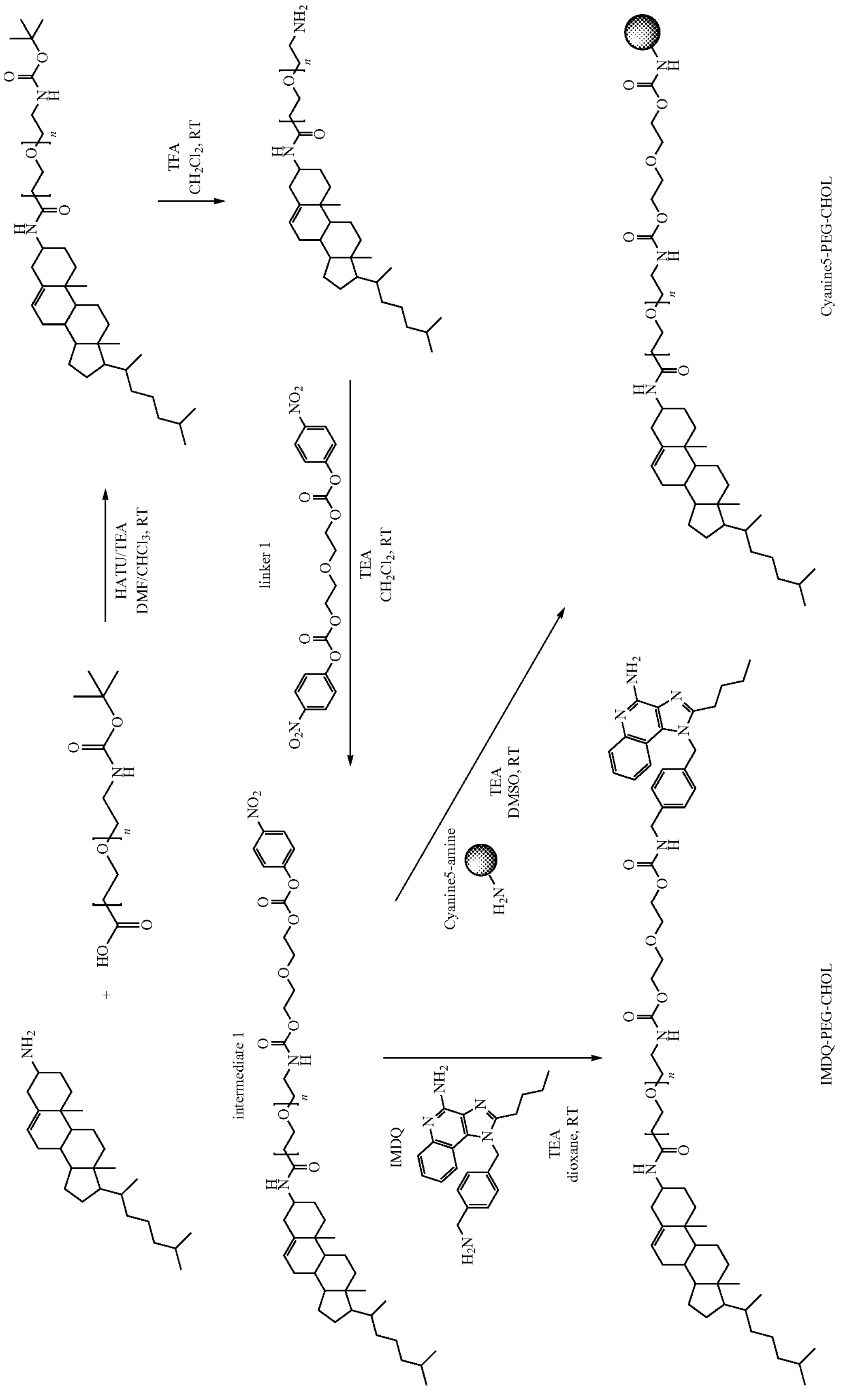
linker 1
intermediate 1
IMDQ
Cyanine5-amine
IMDQ-PEG-CHOL
Cyanine5-PEG-CHOL Cholesterylamine and IMDQ were synthesized according to literature.

Synthesis of Cholesterylamine

First, the alcoholic hydroxyl group of cholesterol was transformed to an azide through a Mitsunobu reaction in the presence of diphenylphosphoryl azide (DPPA). Cholesterol (2.0 g, 5.17 mmol) was dissolved in a round bottom flask equipped with a stirring bar containing anhydrous THF (20 mL). Triphenylphosphine ($PPh_3$, 1.63 g, 6.21 mmol) and diisopropyl azodicarboxylate (DIAD, 1.22 mL, 6.21 mmol) was added to the round bottom flask. Upon addition of DIAD, the reaction mixture developed a yellow colour. After 10 minutes, DPPA (1.34 mL, 6.21 mmol) was added and the mixture stirred overnight at room temperature under inert atmosphere. The reaction mixture was reduced under vacuum and further purified by column chromatography (cyclohexane), to yield a purified white powder (yield=60%). The resulting product cholesteryl-N3 was analyzed by $^1$H-NMR and ATR-IR.

Next, a Staudinger reduction was executed to reduce the azide group to a primary amine function with $PPh_3$. The obtained cholesteryl-N3 (400 mg, 0.97 mmol) was transferred into a round bottom flask containing a stirring bar and dissolved in anhydrous THF (2.0 mL) under inert atmosphere. A solution of $PPh_3$ (2.55 g, 9.72 mmol) in dry THF (5.0 mL) was added. After 30 minutes, 2 mL water was added and the reaction mixture stirred overnight at room temperature equipped with a balloon to trap the released nitrogen gas. The reaction mixture was diluted extensively with toluene before being reduced under vacuum by 50° C. The crude product was purified by column chromatography using a gradient (from 95:5 DCM:MeOH to 95:5 DCM: MeOH+1% ammonium hydroxide), yielded a white powder which was characterized by $^1$HNMR, ATR-IR and MS (yield=98%). ESI-MS: m/z [M+H]+=386.37 (theoretical); found=386.363.

Synthesis of PEG-CHOL

A round bottom flask containing a stirring bar was loaded with Boc-NH-PEG-COOH (300 mg, 0.098 mmol) and dissolved in anhydrous N,N-dimethylformamide (DMF, 3 mL) under inert atmosphere. HATU (40.84 mg, 0.107 mmol) was added to the stirring solution followed by 20.4 μL of triethylamine (TEA, 0.146 mmol). After 5 min, a solution of cholesterylamine (56.4 mg, 0.146 mmol) in dry chloroform (1.5 mL) was added and stirred at room temperature for 2 h, yielding a slightly yellow reaction mixture. The reaction mixture was co-evaporated with a large excess of toluene to remove DMF. Subsequently, the crude product was purified by threefold precipitation in ice cold diethyl ether followed by column chromatography (90:10 DCM:MeOH) (yield=86%). The white PEG-CHOL-NH Boc powder was analyzed by $^1$H-NMR, DMAc-SEC and MALDI-TOF.

Subsequently the Boc-group was removed by dissolving Boc-NH-PEG-CHOL (200 mg, 0.058 mmol) in 2 mL of DCM in a round bottom flask equipped with a stirring bar. An equal amount of trifluoroacetic acid (TFA, 2 mL) was added and the solution was stirred for 2 h opened to ambient air and temperature. Prior to concentration under vacuum, a large excess of toluene was added to the reaction mixture. Finally, the product was transferred to dialysis membranes and dialyzed against 0.1% v/v ammonium hydroxide solution in demineralized water for multiple days and one day against demineralized water. After lyophilization, the white fluffy powder $NH_2$-PEG-CHOL was characterized by $^1$H-NMR and MALDI-TOF.

Synthesis of Linker 1

In a round bottom flask equipped with a stirring bar, p-nitrobenzyl chloroformate (2.02 g, 10 mmol) was dissolved in anhydrous DCM and cooled on ice. A mixture of diethylene glycol (424.5 mg, 4 mmol) and TEA (1.67 mL, 12 mmol) in 10 mL anhydrous DCM were added dropwise and stirred for an additional 30 minutes on ice. After 2 h on room temperature, the reaction mixture was concentrated under vacuum, dissolved in EtOAc and filtered. After evaporation of the solvent under reduced pressure, the linker was analyzed by $^1$H-NMR and MS.

Synthesis of IMDQ-PEG-CHOL

First, linker 1 (65.3 mg, 0.15 mmol) was dissolved in 2.5 mL anhydrous DCM under inert atmosphere. After addition of 2 equivalent of dry TEA (8.35 μL, 0.06 mmol), $NH_2$-PEG-CHOL (100 mg in 2 mL anhydrous DCM, 0.03 mmol) was added dropwise under stirring and a distinct yellow color appeared indicating the release of p-nitrophenol. After overnight reaction, purification was performed by double precipitation into a mixture of ice-cold hexane:acetone (80: 20). The resulting intermediate 1 was dried under vacuum and analyzed by NMR and SEC with DMAc as mobile phase.

In the second step, intermediate 1 (50 mg, 0.014 mmol) and IMDQ (9.5 mg, 0.22 mmol) were weighed into a round bottom flask with stirring bar. The compounds were dissolved in 2.3 mL anhydrous 1,4-dioxane and anhydrous TEA (9.76 μL, 0.07 mmol) was added to solution under vigorous stirring. After 3 h at room temperature, a few drops of dry methanol were added and the reaction was stirred overnight. Next, the solution was transferred into a dialysis membrane (1 kDa) and dialyzed for multiple days against demineralized water. After freeze drying, the with fluffy IMDQ-PEG-CHOL powder was characterized by $^1$H-NMR, HPLC and MALDI-TOF. HPLC conditions to verify absence of freely soluble IMDQ: LiChroCart® C18 column 250-4, mobile phase $H_2O$/ACN 65:35 with 0.1% TFA, flow rate at 1 mL/min and detection at 250 nm. Note that IMDQ-PEG was synthesized in similar fashion, but omitting the conjugation of cholesterylamine.

Synthesis of Cyanine5-PEG-CHOL $NH_2$-PEG-CHOL (25 mg, 7.49 μmol) was weighted into a Schlenk tube equipped with a magnetic stirring bar and dissolved in 2.5 mL dry DMSO under inert atmosphere. Then, 0.21 mL of cyanine5 N-hydroxysuccinimide ester (stock solution of 25 mg/mL in anhydrous DMSO, 7.86 μmol) and anhydrous TEA (5.2 μL, 37.42 μmol) were added to the Schlenk tube and further stirred overnight at room temperature. After dialyzed for three days against demineralized water, Cyanine5-PEG-CHOL was isolated as a fluffy blueish powder after lyophilization.

Synthesis of Lipid-Polyethylene Glycol Amphiphiles. Lipid-PEG amphiphiles were synthesized by conjugation of diverse lipids to hetero-bifunctional PEG bearing a carboxylic acid and a Boc-protected primary amine at the chain ends (i.e., COOH-PEG-NH-Boc). PEG with a molecular weight of 3 kDa was chosen based on: 1) Commercial availability of the starting material, and 2) an intermediate length—long enough to afford water solubility of the final construct bearing two hydrophobic end groups, but not too long as to preclude full chain end conversions and limit the final drug load. Cholesterol and dialkyl lipids, but not mono-alkyl lipids were reported to be potent albumin binders and mediators of lymphatic translocation. Hence, cholesterol and a series of dialkyl lipids with varying alkyl chain, that is, 8, 12, and 18 carbons in length, were used as lipid motifs. The amine-functionalized lipids were conjugated to the carboxylic acid group of PEG by 1-[Bis(dimethylamino)methylene]-1H-1,2,3-triazolo[4,5-b]pyridinium 3-oxid hexafluoro-phosphate (HATU)-mediated amidation chemistry and purified by normal phase column chromatography yielding modified PEG derivatives (Scheme 2). The lipids were conjugated to PEG through a stable amide bond rather than an ester bond as the latter could be prone to premature hydrolysis.

Size exclusion chromatography (SEC) of the lipid-PEG amphiphiles showed a clear shift toward shorter retention times upon lipid conjugation with no tailing from unreacted PEG. The commercial PEG starting material showed a small secondary peak at shorter elution time, which was identified by matrix-assisted laser desorption-ionization-time of flight mass spectrometry (MALDI-ToF MS) as PEG lacking the Boc protecting group at the terminal amine. This impurity did not constitute an issue as in subsequent conjugation steps to fluorescent tracers or TLR agonists, the Boc group is removed yielding lipid-PEG-$NH_2$. Overall, all lipid-conjugates exhibited low dispersity, indicative of efficient conjugation and the presence of uniform compounds; this finding was further confirmed by diffusion ordered nuclear magnetic resonance spectroscopy (DOSY-NMR) and MALDI-TOF MS analysis, which showed a major single peak distribution of lipid-PEG-NH-Boc for all lipid-PEG amphiphiles. See, De Vrieze et al. "Lipid Nature and Alkyl Length Influence Lymph Node Accumulation of Lipid-Polyethylene Glyco Amphiphiles," *Adv. Ther.*, 4(8):1-9 (2021) (incorporated by reference herein in its entirety).

Biolayer interferometry analysis. Bovine serum albumin (BSA) was biotinylated by reacting it with 5:1 excess of biotin-NHS followed by dialysis and lyophilization. Hydrated streptavidin sensors were dipped in PBS to record a baseline for 60 seconds, followed by dipping into biotinylated BSA (12.5 nM, 66.5 kDa) in PBS for 300 s, and dipping for 30 s in PBS for washing. Next, a second baseline was recorded by dipping in fresh PBS for 120 s. Association of IMDQ-PEG-CHOL was measured by dipping into a solution of IMDQ-PEG-CHOL in PBS for 600 s. Note that the experiment was ran in parallel for different concentrations of IMDQ-PEG-CHOL. Dissociation of IMDQ-PEG-CHOL was recorded by dipping in PBs for 600 s. The experiment was performed in a black flat bottom 96 well plate set at 30° C. by 1000 rpm, using an Octet RED96 model (Pall Fortébio). Data processing was done by the FortéBio software package.

Cell cytotoxicity (MTT) assay. DC 2.4 cells were plated seeded in 96 well plates at a density of 8 000 cells per well in 200 μL culture medium. 50 μL of sample (dilution series in PBS, ranging from $10^{-4}$ mg/mL to 0.5 mg/mL), PBS (negative control, 100% viability) and DMSO (positive control, 0% viability) were added to the wells. After 72 h, the medium was aspirated and cells were washed with 200 μL PBS followed by addition of 100 of diluted MTT stock solution. After 1 h, the solution was removed and the formed formazan crystals were dissolved in 50 μL DMSO. Quantification was done by measuring the absorbance at 590 nm Scheme 2. Synthesis of lipid-PEG amphiphiles.

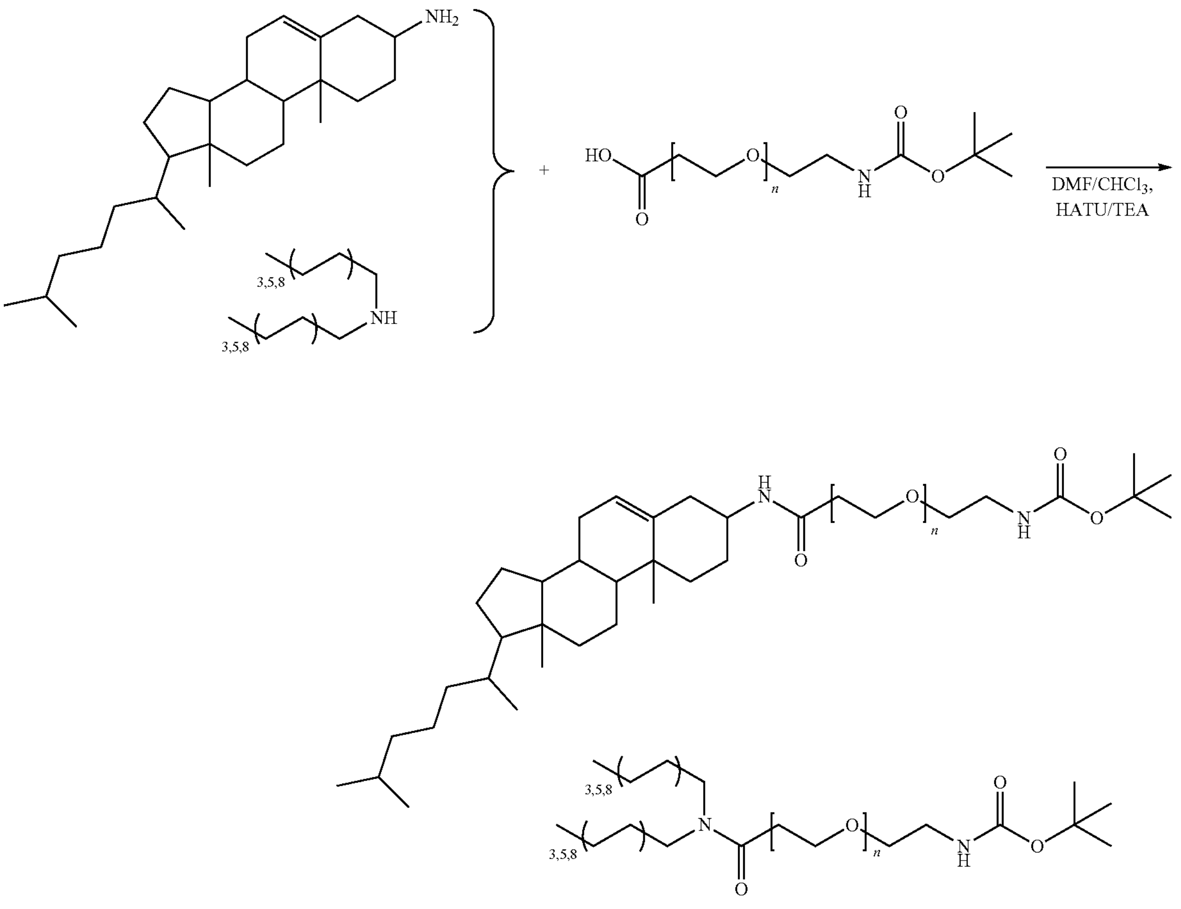

using a microplate reader. Note, thiazolyl blue tetrazolium bromide (MTT, 50 mg) was dissolved in 10 mL sterile PBS, filtrated (membrane 0.22 μm) and 1/5 diluted in culture medium prior to use in this assay.

Confocal microscopy. DC 2.4 cells were seeded in Willco-Dish glass bottom at a concentration of 10 000 cells in 180 μL culture medium and allowed to adhere overnight. Cells were pulsed overnight with 10 mL of a 1 mg/mL Cyanine5-PEG-CHOL or Cynanine5-PEG solution in PBS. Next, the culture medium was aspirated and cells zero fixated with 4% PFA for 30 min followed by washing with PBS and confocal imaging using a Leica DMI6000B microscope (63×1.40 NA objective) coupled to an AndorDSD2 confocal scanner and a Zyla5.5 CMOS camera. Image processing was done using the ImageJ software package.

Flow cytometry analysis of in vitro IMDQ-PEG(-CHOL) association. DC 2.4 cells were seeded out in 24 well plate at a concentration of 200 000 cells per well in 450 μL of culture medium. Cells were pulsed with samples and incubated overnight at 37° C. Afterwards, the supernatants were removed, cells were washed with PBS and detached with cell dissociation buffer (0.5 mL, 15 min, 37° C.). The content of the wells was transferred to an Eppendorf and centrifuged (5 min, 300 G, 4° C.). After aspiration of the supernatant, the cell pellets was resuspended in PBS and analyzed using a BD Accuri Flow Cytometer. Data were processed using the FlowJo software package.

RAW blue innate immune activation assay. RAW blue 264.7 macrophages were seeded in flat-bottom 96 well plate at a density of 70 000 cells per well, suspended in 180 μL culture medium and pulsed with 20 μL of sample for 24 h at 37° C. at different concentrations of IMDQ-PEG-CHOL, IMDQ-PEG, IMDQ and PBS. Subsequently, 50 μL of supernatant was transfer to a new flat-bottom 96 well plate followed by addition of 150 μL of QUANTI-Blue™ reagent solution, prepared according to the manufacturer's instruction (Invivogen). After 30 minutes at 37° C., the SEAP levels were determined by UV-Vis spectrophotometry at 620 nm using a microplate reader. Note, the colorimetric quantification of the samples was obtained relative to the negative control and each concentration was performed in fivefold.

Analysis of in vivo lymphatic drainage. 20 μL (1 mg/mL in PBS) of Cyanine5-PEG-CHOL or Cyanine5-PEG were injected into the footpad of female C57BL/6 WT mice. Two mice were used per group and injected in both footpad. At the designated time point, mice where sacrificed and popliteal lymph nodes where isolated for flow cytometry and confocal imaging. A single cell suspensions was prepared form the dissected popliteal lymph nodes for analysis by flow cytometry. Isolated lymph nodes were collected in ice cold PBS, smashed through 70 μm cell strainers, washed with PBS and stained with a fixable dead/live-staining. 123count ebeads were added to determine cellularity prior to Analysis by a BD FACS Quanto flow cytometer. Data were processed using the FlowJo software package.

For Confocal imaging popliteal lymph nodes where frozen in OCT (Sakura, 4583). frozen sections (8-μm) were cut by cryostat. These sections where fixed for 4 min in PFA 2%, washed with PBS. Images were acquired on a Zeiss LSM710 confocal microscope equipped with 488-nm, 561-nm and 633-nm lasers and with a tunable two-photon laser. Confocal imaging was done using a Leica DMI6000B microscope (10×0.70 NA objective) coupled to an AndorDSD2 confocal scanner and a Zyla5.5 CMOS camera. Image processing was done using the ImageJ software package.

In vivo immune activation imaging. Luciferase reporter mice (IFNβ+/Δβ-luc) with a BALB/c background, aged 7-9 weeks, were housed in individual ventilated cages and given ad libitum access to food and water. 20 mL of IMDQ-PEG-CHOL, IMDQ-PEG or IMDQ were injected subcutaneously in the footpad (n=3) at an equivalent INDQ dose of 2 mg. For in vivo imaging at the given time points, mice were injected subcutaneously with 200 μL D-luciferin and in vivo luminescence imaging was recorded 12 min later using the IVIS Lumina II imaging system. Local (DLN and DLN+foot pad) luminescence and full-body luminescence were quantified using the Living Image 4.4 software.

Analysis of in vivo lymphocyte targeting and activation. 20 μL (containing an equivalent IMDQ dose of 2 mg) of IMDQ-PEG-CHOL or Cyanine5-PEG-CHOL was injected into the footpad of female C57BL/6 WT mice. At the designated time point, mice where sacrificed and popliteal lymph nodes where isolated. A single cell suspension was prepared form the dissected popliteal lymph nodes for analysis by flow cytometery. Isolated lymph nodes were collected in ice cold PBS, smashed through 70 μm cell strainers, washed with PBS and stained for 30 min at 4° C. with following primary labeled antobibodies: CD3, CD20, CD11c, MHCII, CD86, CD40. Live dead ratio's where determined by staining with fixable dead/live-staining and 123count ebeads were added to determine cellularity prior to acquiring them on 123count ebeads were added to determine cellularity prior to Analysis by a BD FACS Quanto flow cytometer. Data were processed using the FlowJo software package.

6.2 Results and Discussion

In the present work, we report on a novel amphiphilic carrier for imidazoquinoline (IMDQ) TLR7/8 agonists with high translational potential, based on conjugation of a single imidazoquinoline to the chain end of a cholesteryl-polyethylene glycol amphiphile (IMDQ-PEG-CHOL; FIG. 1A). This design mediates binding to serum proteins such as albumin (13,17) (FIG. 1B) and in contrast to pure lipidation, the conjugate is well water-soluble. As a result, mobility in tissue is achieved without depot formation, with potential loss in adjuvancy efficacy, hence avoiding the need for additional formulation.

We report that the adjuvant, termed IMDQ-PEG-CHOL, is a potent adjuvant candidate which can enhance vaccine efficiency and induced robust Th1 skewed antibody responses in mice when delivered as a single shot with either admixed seasonal quadrivalent inactivated influenza vaccine (QIV, for Influenza) or S protein (for SARS-CoV-2). Moreover, as discussed below, IMDQ-PEG-CHOL was able to infer protection in influenza (IVR-180-H1N1)-infected or SARS-CoV-2-infected mice. In this context, it is noteworthy to mention that a major limitation in COVID19-vaccine development is the lack of susceptible small animal models for pre-clinical assessment and evaluation of its efficacy. Reportedly, the laboratory strains of mice that express mouse ACE-2 is not targeted by SARS-CoV-2 because of species-specific variations in ACE-2 receptors between mouse and human. Here we made use a of a mouse model where hACE-2 was induced through an adenoviral vector (Ad5-hACE2), which allows for subsequent replication of SARS-CoV-2 upon infection in the airways of transduced mice.

IMDQ-PEG-CHOL Induces Potent Innate Immune Activation in Lymph Nodes

The imidazoquinoline 1-(4-(aminomethyl)benzyl)-2-butyl-1H-imidazo[4,5-c]quinolin-4-amine (IMDQ) (18) was conjugated to a cholesteryl-poly(ethylene glycol) (CHOL-PEG) conjugate, yielding IMDQ-PEG-CHOL. As a control, non-amphiphilic IMDQ-PEG was synthesized. (FIG. 1A)

PEG with a molecular weight of 3 kDa was chosen as an optimal compromise between water solubility and drug load. Characterization of the conjugate was performed by MALDI-ToF analysis (FIG. 12) whereas HPLC analysis (FIG. 13) proved absence of free soluble non-conjugated IMDQ. Both IMDQ-PEG-CHOL and IMDQ-PEG were water-soluble, but only IMDQ-PEG-CHOL showed affinity towards albumin as measured by biolayer interferometry (FIG. 2A). On the in vitro level, the presence of the CHOL motif dramatically improved cellular uptake by DC2.4 (FIG. 2B-2C; note that for imaging purpose, IMDQ was replaced by the fluorescent probe Cynanine5), a model mouse dendritic cell line, and was more potent in inducing NFkB activation in a reporter cell line (FIG. 2D), while being non-toxic within the tested experimental window (FIG. 2E). We attribute this to the ability of the cholesterol motif to interact with the phospholipid cell membrane.

On the in vivo level, using a transgenic luciferase-reporter mouse model for IFN β-production (19), we found that local administration (i.e. subcutaneous injection into the footpad) of IMDQ-PEG-CHOL, in contrast to unformulated IMDQ, dramatically reduced systemic innate immune activation, while focusing its activity to the site of injection and the draining (popliteal) lymph node (FIG. 3A). Interestingly, the CHOL motif appeared crucial for mediating lymphatic translocation as the IMDQ-PEG control induced very limited activity in the draining lymph node. To further support this, we performed microscopic (FIG. 3B1) and flow cytometry (FIG. 3B2) analysis of popliteal lymph nodes of mice that received fluorescent Cyanine5-PEG-CHOL or Cyanine-PEG, respectively. These experiments revealed a dramatic increase in fluorescence for when the conjugates contained the CHOL motif. A more detailed analysis of immune cells subsets in the draining lymph node revealed that vast percentages of lymphocytes, notably over 50% of DCs and macrophage, as well as 40% of B cells, were targeted by Cyanine5-PEG-CHOL (FIG. 3C). In a similar experimental setting, IMDQ-PEG-CHOL induced lymphangiogenesis (FIG. 3D1) and robust activation (FIG. 3D2) of lymphocytes. Taken together, these data support our hypothesis that IMDQ-PEG-CHOL is a potent adjuvant that focuses its activity to draining lymphoid tissue, combined with a promising safety profile.

Figure 4A:
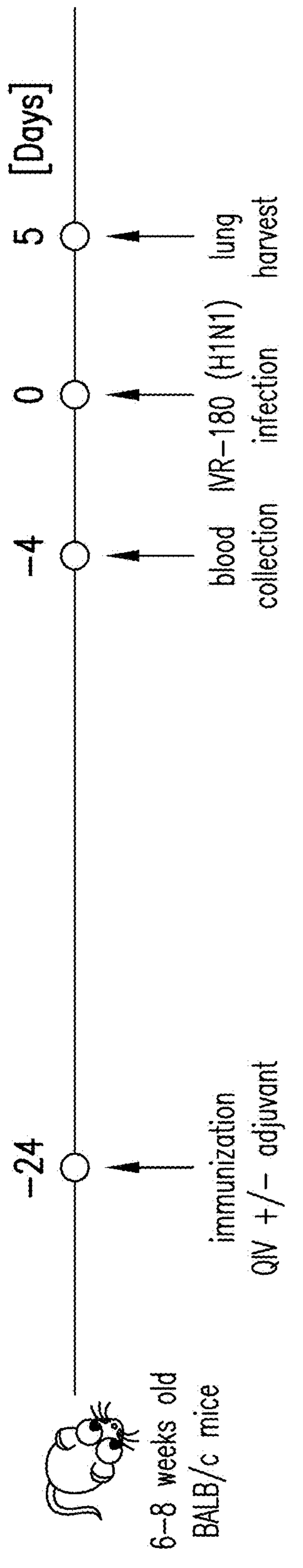
Figure 4B:
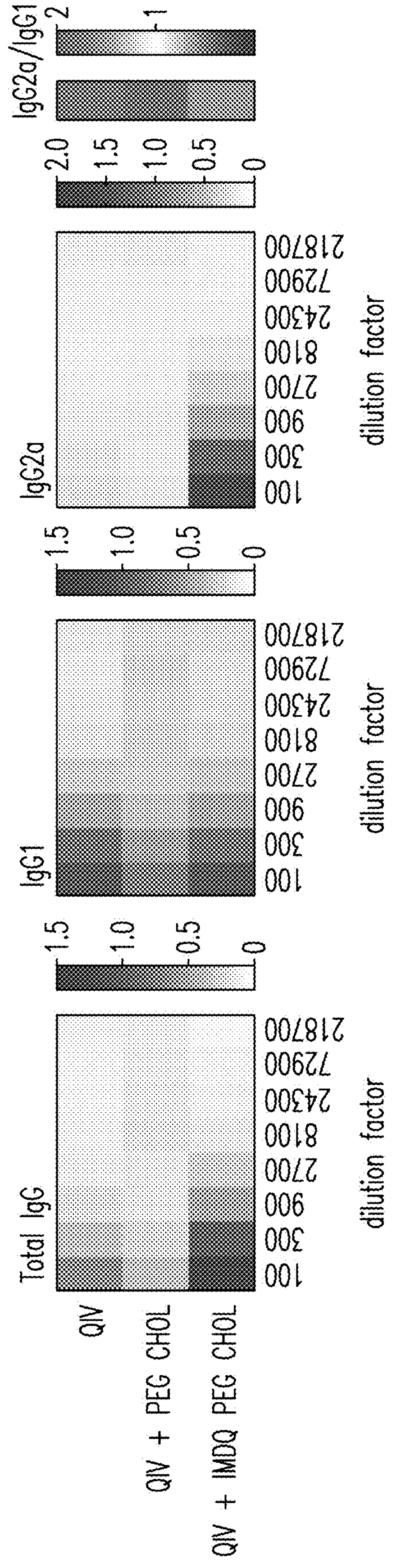
Figure 4C:
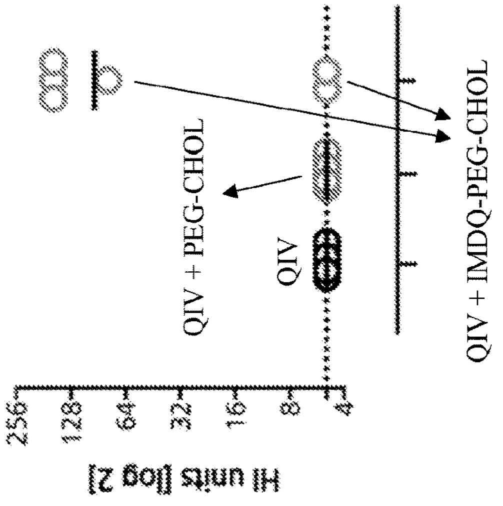

IMDQ-PEG-CHOL Induces a Balanced Neutralizing Antibody Response to Influenza Vaccine We evaluated the potential of IMDQ-PEG-CHOL to adjuvant a licensed vaccine, i.e. the quadrivalent influenza vaccine (QIV), in a well-established preclinical vaccination-infection model. Hereto we vaccinated Balb/c mice with each of 1.5 μg of QIV with or without 100 μg of IMDQ-PEG-CHOL or PEG-CHOL as a control. The study protocol is outlined in FIG. 4A. Six mice in each group received a total of 100 ul vaccine-adjuvant mixture, intramuscularly, divided over both hind legs and the blood was collected 3 weeks post vaccination, followed by serological assays. For detection of influenza-specific antibodies induced by the QIV vaccines, we used vaccine antigen to coat ELISA plates. The total IgG antibody titers in mice which received QIV only or QIV+ PEG-CHOL were very low as compared to the mice which were vaccinated with QIV+ IMDQ-PEG-CHOL (also shown as AUC in FIGS. 6A-6C). Unadjuvanted QIV and PEG-CHOL admixed QIV resulted mainly in vaccine-specific IgG1 antibodies, whereas IMDQ-PEG-CHOL resulted in a balanced IgG1/IgG2a response as shown in FIG. 4B. Interestingly, QIV+PEG-CHOL resulted in even lower antibody responses than QIV alone, an observation we confirmed in an independent vaccination experiment (data not shown). Four out of six mice that received QIV+IMDQ-PEG-CHOL could efficiently inhibit hemagglutination of chicken red blood cells (RBC) in vitro, by IVR-180, the H1N1 virus component in QIV, with hemagglutination inhibition (HI) titers outperforming those of the other immunized groups (FIG. 4C).

Figure 4D:
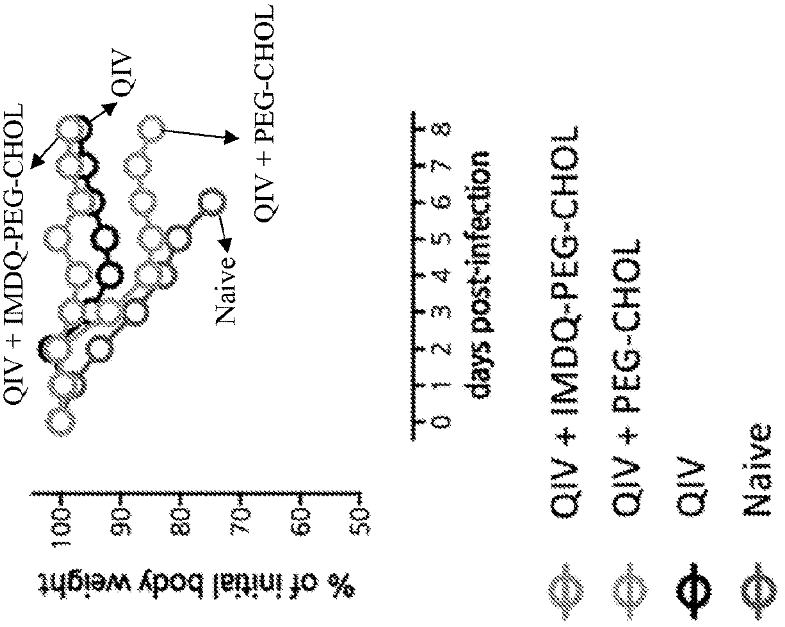
Figure 4E:
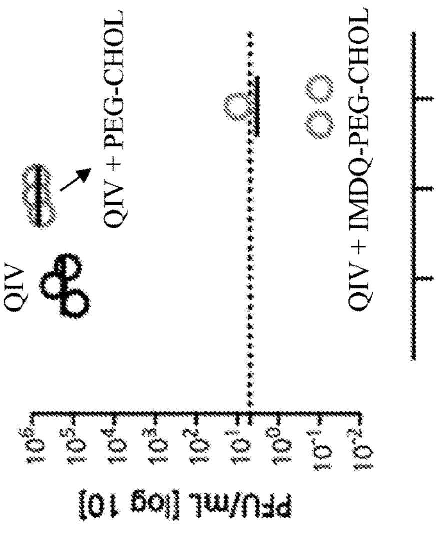
Figure 5A:
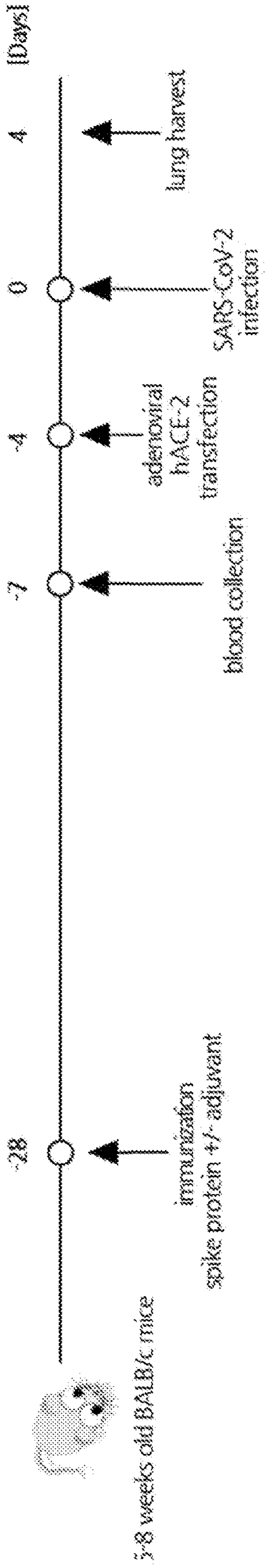
Figure 5B:
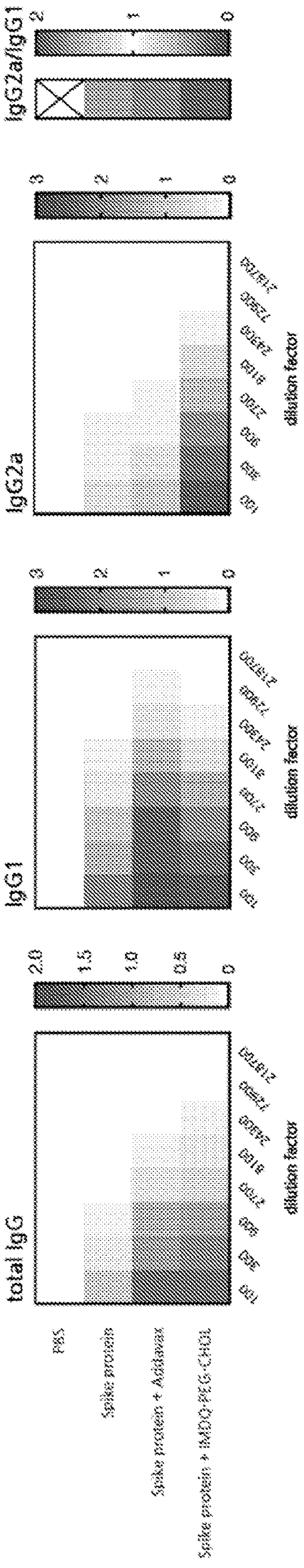
Figure 5D:
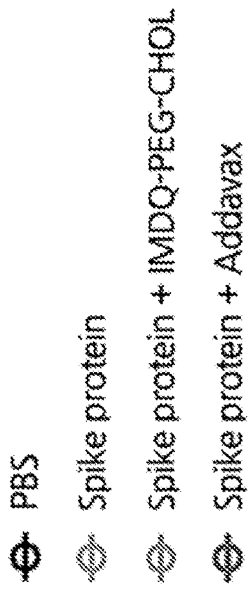
Figure 5D:
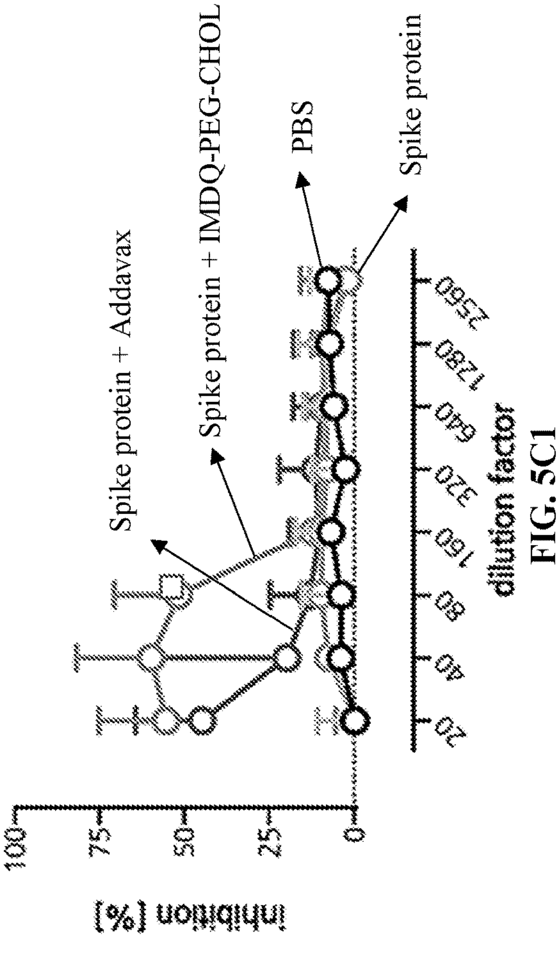
Figure 5D:
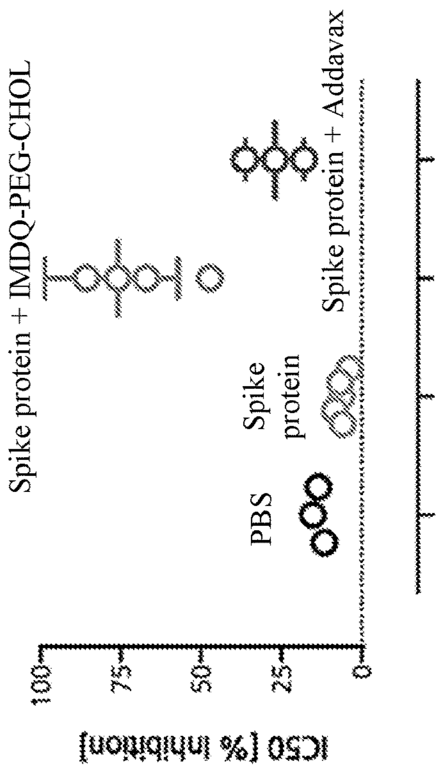
Figure 5D:
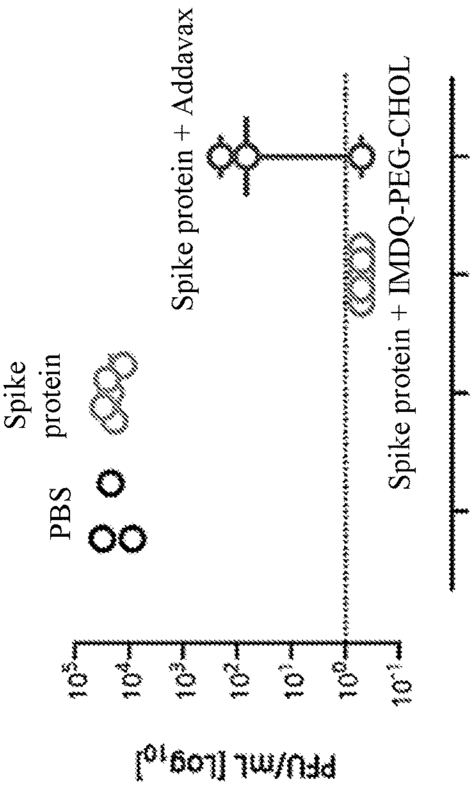

Next, the immunized mice were challenged with a hundred-fold half lethal dose (LD50) of IVR-180 (H1N1) virus to examine the magnitude of protection against viral infection in vivo. The lungs were harvested from three mice in each group 5 days post challenge to determine lung virus titers. Consistent with the ELISA and HI data, mice immunized with QIV+IMDQ-PEG-CHOL exhibited best reduction of viral lung titers as evidenced by an almost negligible number of plaques when compared to other groups (FIG. 4E). This was also reflected in the optimal protection from body weight loss of QIV+IMDQ-PEG-CHOL mice after viral challenge (FIG. 4D). In conclusion, our novel adjuvant IMDQ-PEG-CHOL, was able to offer excellent control of viral infection and therefore, might also hold promise to confer protective immunity against other respiratory viruses such as SARS-CoV-2.

IMDQ-PEG-CHOL Induces a Balanced Neutralizing Antibody Response to SARS-CoV-2 Immunization We next investigated the potential of IMDQ-PEG-CHOL to adjuvant recombinant SARS-CoV-2 S protein. For this purpose Balb/c mice were immunized intramuscularly with 6 ug of recombinant trimeric S protein either unadjuvanted or adjuvanted with IMDQ-PEG-CHOL or with equivalent amounts of MF59-like water-in-oil vaccine Addavax as a control established vaccine adjuvant. The recombinant vaccine consisted of the ectodomain of the SARS-CoV-2 Spike protein from which the polybasic cleavage site was removed. Stabilizing prolines were added at positions 986 and 987 and trimerization was promoted by fusion to a T4 trimerization domain (see methods section for more details). The study protocol is outlined in FIG. 5A. Serum was collected after 21 days post immunization and analyzed for S protein specific IgG titers. Whereas non-immunized mice evidently did not show any detectable S protein-specific titers in their sera, immunization with S protein induced S protein-specific titers in all groups (FIG. 5B), also shown as area under the curve (AUC) titers in FIGS. 7A-7C. The total S protein-specific IgG titers were found to be the highest in the IMDQ-PEG-CHOL adjuvanted group. Additionally, S protein+IMDQ-PEG-CHOL immunization resulted in a higher IgG2a/IgG1 ratio, suggesting a more potent Th1 immune response and more efficient class switching towards IgG2a as compared to S protein only or S protein+Addavax immunization.

Next, the sera from vaccinated mice were used to test the ability to inhibit SARS-CoV-2 infection in vitro. Although immunization with non-adjuvanted S protein was able to induce some IgG titers, it was found ineffective in neutralizing viral infection of Vero E6 cells in vitro in a microneutralization assay (FIG. 5C1-5C2). By contrast, serum of mice immunized with Spike protein+IMDQ-PEG-CHOL was able to neutralize >50% of SARS-CoV-2 virus infection in this assay, which was also significantly higher than the serum of mice immunized with Spike protein+Addavax.

IMDQ-PEG-CHOL Induces Protective Immunity Against SARS-CoV-2 in a Mouse Model

Finally, we investigated to what extent S protein+IMDQ-PEG-CHOL immunization is able to confer protection against a SARS-CoV-2 viral challenge. As mice do not express the hACE-2 receptor that is needed for the virus to infect the host, we first transduced immunized mice with an adenoviral vector encoding for hACE-2 by intranasal instillation. Four days later, mice we challenged with SARS-CoV-2 virus and again 4 days later, lungs were harvested, and the residual viral infection was quantified by a plaque assay. Interestingly, whereas non-adjuvanted S protein could not confer any protection, relative to the non-immunized group, S protein+IMDQ-PEG-CHOL vaccination conferred sterilizing immunity against the SARS-CoV-2 infection with plaque numbers below the detection limit (FIG. 5D), and performed significantly better that S protein+Addavax immunization, which correlates with the higher microneutralization titers observed in the S protein+IMDQ-PEG-CHOL group (FIG. 5C1-5C2).

6.3 Conclusions

In summary, we have shown in this work that IMDQ-PEG-CHOL is a potent adjuvant with enhanced safety profile that induced innate immune activation in lymphoid tissue upon local administration. Whereas IMDQ in soluble, unformulated form, rapidly enters systemic circulation, conjugation to a lipid-polymer amphiphile prevents the latter while promoting translocation to the draining lymph node, likely through binding to albumin in the interstitial flow. In mouse vaccination/challenge models for influenza and SARS-CoV-2, we have demonstrated that QIV and S protein adjuvanted with IMDQ-PEG-CHOL induced by a single shot immunization robust Th1 skewed antibody responses, as evidenced by higher IgG2a/IgG1 ratios. Importantly, vaccination with QIV and S protein adjuvanted with IMDQ-PEG-CHOL resulted in virus-specific neutralizing antibodies and control of viral infection after challenge with influenza and SARS-CoV-2 viruses, respectively. Since IgG2a subclass is known to engage Fcγ receptors that are involved in antiviral protection mechanisms like antibody-mediated cellular cytotoxicity and phagocytosis, IMDQ-PEG-CHOL might be beneficial to promote such responses. Whereas we are aware of the limitations of the present studies, we do believe that the overarching message that single vaccination with a properly adjuvanted recombinant S protein-based vaccine is able to induce protective immunity in a mouse model, is of great relevance with regard to broadening the arsenal of emerging COVID-19 vaccines. Safe adjuvants like the IMDQ-PEG-CHOL described in our study may help enhance vaccine efficiency if deemed necessary from ongoing clinical trials, similar to the recent development of MF59-adjuvanted influenza vaccines for the elderly. Use of efficient adjuvants may also reduce the amount of vaccine needed to induce a protective immune response, which is important in case there is vaccine shortage, as is the case during this COVID19 pandemic.

7. REFERENCES CITED IN BACKGROUND AND/OR EXAMPLE 1

1. Letko M, Marzi A, Munster V. Functional assessment of cell entry and receptor usage for SARS-CoV-2 and other lineage B betacoronaviruses. Nat Microbiol. 2020 Feb. 24; 1-8.
2. Zhu N, Zhang D, Wang W, Li X, Yang B, Song J, et al. A Novel Coronavirus from Patients with Pneumonia in China, 2019. N Engl J Med. 2020 Feb. 20; 382(8):727-33.
3. Wu F, Zhao S, Yu B, Chen Y-M, Wang W, Song Z-G, et al. A new coronavirus associated with human respiratory disease in China. Nature. 2020; 579(7798):265-9.
4. Krammer F. SARS-CoV-2 vaccines in development. Nature. 2020 Sep. 23; 1-12.
5. de Geest B, Ye T, Zhong Z, Garcia-Sastre A, Schotsaert M. Current status of COVID-19 (pre)clinical vaccine development. Angew Chem Int Ed Engl [Internet]. 2020 Jul. 14 [cited 2020 Oct. 2]; Available from: https://www.ncbi.nlm.nih.gov/pmc/articles/PMC7405471/6.
6. Benton D J, Wrobel A G, Xu P, Roustan C, Martin S R, Rosenthal P B, et al. Receptor binding and priming of the spike protein of SARS-CoV-2 for membrane fusion. Nature. 2020 Sep. 17; 1-8.
7. Lamers M M, Beumer J, van der Vaart J, Knoops K, Puschhof J, Breugem T I, et al. SARS-CoV-2 productively infects human gut enterocytes. Science [Internet]. 2020 May 1 [cited 2020 Oct. 2]; Available from: https://www.ncbi.nlm.nih.gov/pmc/articles/PMC7199907/8.
8. Qi F, Qian S, Zhang S, Zhang Z. Single cell RNA sequencing of 13 human tissues identify cell types and receptors of human coronaviruses. Biochem Biophys Res Commun. 2020 May 21; 526(1):135-40.
9. Iwasaki A, Medzhitov R. Regulation of adaptive immunity by the innate immune system. Science. 2010 Jan. 15; 327(5963):291-5.
10. Coffman R L, Sher A, Seder R A. Vaccine Adjuvants: Putting Innate Immunity to Work. Immunity. 2010 Oct. 29; 33(4):492-503.
11. Hemmi H, Kaisho T, Takeuchi O, Sato S, Sanjo H, Hoshino K, et al. Small anti-viral compounds activate immune cells via the TLR7 MyD88-dependent signaling pathway. Nat Immunol. 2002 February; 3(2):196-200.
12. Nuhn L, Vanparijs N, De Beuckelaer A, Lybaert L, Verstraete G, Deswarte K, et al. pH-degradable imidazoquinoline-ligated nanogels for lymph node-focused immune activation. Proc Natl Acad Sci. 2016 Jul. 19; 113(29):8098-103.
13. Vrieze J D, Louage B, Deswarte K, Zhong Z, Coen R D, Herck S V, et al. Potent Lymphatic Translocation and Spatial Control Over Innate Immune Activation by Polymer-Lipid Amphiphile Conjugates of Small-Molecule TLR7/8 Agonists. Angew Chem Int Ed. 2019; 58(43): 15390-5.
14. Van Herck S, Deswarte K, Nuhn L, Zhong Z, Portela Catani J P, Li Y, et al. Lymph-Node-Targeted Immune Activation by Engineered Block Copolymer Amphiphiles—TLR7/8 Agonist Conjugates. J Am Chem Soc. 2018 Oct. 31; 140(43):14300-7.
15. Kasturi S P, Skountzou I, Albrecht R A, Koutsonanos D, Hua T, Nakaya H I, et al. Programming the magnitude and persistence of antibody responses with innate immunity. Nature. 2011 Feb. 24; 470(7335):543-7.
16. Lynn G M, Laga R, Darrah P A, Ishizuka A S, Balaci A J, Dulcey A E, et al. In vivo characterization of the physicochemical properties of polymer-linked TLR agonists that enhance vaccine immunogenicity. Nat Biotechnol. 2015 November; 33(11):1201-10.
17. Liu H, Moynihan K D, Zheng Y, Szeto G L, Li A V, Huang B, et al. Structure-based Programming of Lymph Node Targeting in Molecular Vaccines. Nature. 2014 Mar. 27; 507(7493):519-22.
18. Shukla N M, Malladi S S, Mutz C A, Balakrishna R, David S A. Structure-Activity Relationships in Human Toll-Like Receptor 7-Active Imidazoquinoline Analogues. J Med Chem. 2010 Jun. 10; 53(11):4450-65.
19. Lienenklaus S, Cornitescu M, Zietara N, Lyszkiewicz M, Gekara N, Jabłońska J, et al. Novel Reporter Mouse Reveals Constitutive and Inflammatory Expression of IFN-β In Vivo. J Immunol. 2009 Sep. 1; 183(5):3229-36.
20. Choi A, Ibañez LI, Strohmeier S, Krammer F, Garcia-Sastre A, Schotsaert M. Non-sterilizing, Infection-Permissive Vaccination With Inactivated Influenza Virus Vaccine Reshapes Subsequent Virus Infection-Induced Protective Heterosubtypic Immunity From Cellular to Humoral Cross-Reactive Immune Responses. Front Immunol [Internet]. 2020 Jun. 9 [cited 2020 Aug. 9]; 11. Available from: https://www.ncbi.nlm.nih.gov/pmc/articles/PMC7296151/21.

21. Amanat F, Stadlbauer D, Strohmeier S, Nguyen T H O, Chromikova V, McMahon M, et al. A serological assay to detect SARS-CoV-2 seroconversion in humans. Nat Med. 2020; 26(7):1033-6.

22. Margine I, Palese P, Krammer F. Expression of functional recombinant hemagglutinin and neuraminidase proteins from the novel H7N9 influenza virus using the baculovirus expression system. J Vis Exp JoVE. 2013 Nov. 6; (81):e51112.

23. Stadlbauer D, Amanat F, Chromikova V, Jiang K, Strohmeier S, Arunkumar G A, et al. SARS-CoV-2 Seroconversion in Humans: A Detailed Protocol for a Serological Assay, Antigen Production, and Test Setup. Curr Protoc Microbiol. 2020; 57(1):e100.

24. Amanat F, White K M, Miorin L, Strohmeier S, McMahon M, Meade P, et al. An In Vitro Microneutralization Assay for SARS-CoV-2 Serology and Drug Screening. Curr Protoc Microbiol [Internet]. 2020 September [cited 2020 Oct. 2]; 58(1). Available from: https://www.ncbi.nlm.nih.gov/pmc/articles/PMC7361222/25.

25. Sun J, Zhuang Z, Zheng J, Li K, Wong R L-Y, Liu D, et al. Generation of a Broadly Useful Model for COVID-19 Pathogenesis, Vaccination, and Treatment. Cell. 2020 Aug. 6; 182(3):734-743.e5.

8. EXAMPLE 2: IMDQ-PEG-CHOL COMPARED TO OTHER ADJUVANTS

IMDQ-PEG-CHOL induces superior innate immune signals shortly after QIV vaccination compared to AddaVax. QIV vaccine is an inactivated virus split vaccine licensed for use in humans and is updated on a yearly base to antigenically match the vaccine to circulating influenza viruses. QIV contains vaccine antigens derived from H1N1, H3N2 and two influenza B viruses. Vaccine efficacy for QIV is generally low due to antigenic mismatch with circulating strains or poor antigenicity in certain target groups (for example the elderly). According to the NIAID strategic plan for the development of a universal influenza vaccine (PMID: 29506129), seasonal QIV would benefit from use with adjuvants to enhance vaccine effectiveness against both antigenically matching and mismatched influenza viruses. Moreover, QIV adjuvanted with MF59, an oil in water adjuvant comparable to the reference adjuvant AddaVax for these studies, is available as a geriatric influenza vaccine (Fluad, Seqirus). This study compares QIV adjuvanted with IMDQ-PEG-CHOL, a modified form of imidazoquinoline (IMDQ), which is a TLR7/8 agonist, with enhanced safety profile and lymph node-draining properties, to AddaVax in mice recently (PMID: 33464672). The extent that IMDQ-PEG-CHOL can induce innate immune responses, which can contribute to quality and quantity of vaccine responses, is being investigated. First, levels of ISG15 gene transcripts in blood cells were measured, as a marker for innate immune activation. A single QIV vaccination with IMDQ-PEG-CHOL resulted in induction of ISG15 gene expression, as measured by qPCR in the blood of vaccinated mice (FIG. 8). ISG15 transcript levels were significantly higher for the IMDQ-PEG-CHOL group compared to unadjuvanted QIV or AddaVax group at 2, 7 and 28 days post vaccination but gradually declined over the course of 28 days. AddaVax on the contrary did not result in significantly enhanced ISG15 expression levels compared to unadjuvanted QIV or PBS control groups at any time point.

IMDQ-PEG-CHOL induces superior T cell responses upon QIV vaccination compared to AddaVax. Both AddaVax and IMDQ PEG-CHOL were able to enhance humoral vaccine responses compared to adjuvanted QIV (FIG. 9A). AddaVax was able to induce somewhat higher HAI titers whereas IMDQ-PEG-CHOL resulted in somewhat higher IgG2a ELISA titers. This correlates with a better induction of IFNγ producing cells post vaccination in the IMDQ-PEG-CHOL group (FIG. 9B). Single vaccination with QIV correlates with protection, as measured by absence of severe body weight loss after challenge with 100LD50 and protection was further enhanced for AddaVax or IMDQ-PEG-CHOL adjuvanted groups (FIG. 9C). Adjuvanted QIV also resulted in the best control of lung virus titers at 5 days post infection (FIG. 9D).

IMDQ-PEG-CHOL induces more IFNγ-producing CD4+ T cell responses upon recombinant trimeric SARS-CoV-2 spike protein vaccination compared to AddaS03. As shown in FIG. 10A, IMDQ-PEG-CHOL resulted in better induction of IFNg+CD4+ T cell responses compared to unadjuvanted control or AddaS03, and AS03-like adjuvant. Further, unlike AddaS03, IMDQ-PEG-CHOL did not induce IL4+CD4+ T cell responses that exceeded unadjuvanted control (FIG. 10B), which confirms the favorable antiviral type 1 skewing potential of IMDQ-PEG-CHOL.

9. EXAMPLE 3: CHOLESTERYL-POLYETHYLENE GLYCOL-IMIDAZOQUINOLINE EXHIBITS ADJUVANT PROMOTING CELLULAR AND HUMORAL IMMUNE RESPONSES

This example demonstrates that cholesteryl-PEG-IMDQ triggers both cellular and humoral immune responses when admixed with a model antigen, inducing qualitatively different responses as compared to an established adjuvant.

9.1 Materials and Methods

Adjuvanticity: For analysis of adjuvanticity, OVA (10 μg; Worthingthon) was administered subcutaneously in the base of the tail either in PBS or admixed to either cholesteryl-PEG, cholesteryl-PEG-IMDQ (10 μg IMDQ), or Montanide (1/1 suspension; Seppic) in a total volume of 50 μL. Circulating OVA-specific tetramer+ CD8+ T cells were quantified 7 days after primary immunization and 7 days after secondary boost immunization—the two immunizations were separated by a 7-day interval. The phenotype of the OVA-specific CD8+ T cells was determined in single cell suspensions obtained by mechanical disruption of the spleen. In both cases, samples were stained with the appropriate antibodies for 30 min at 4° C. and acquired on a BD Fortessa flow cytometer. 123 counting beads were used to determine absolute cell numbers and fixable live/dead to discriminate between live and dead cells. Serum antibody titers were determined by ELISA. Briefly, ELISA plates were coated with OVA (0.1 mg mL-1), incubated with serum samples and developed with biotin-labelled anti-mouse isotype specific antibodies, streptavidin-HRP, and tetramethylbenzidine substrate.

Data Presentation and Sample Size: Data are presented as mean±SD in all figures. The number of repeats is mentioned in the legend of each figure for each statistical analysis.

Statistical Methods: Statistical testing was performed by either one- or two-way ANOVA using the GraphPad Prism 9 software package.

9.2 Results

Cholesteryl-PEG conjugated to the TLR7/8 agonist 1-(4 (aminomethyl)benzyl)-2-butyl-1H-IMDQ, (Shukla et al., Bioorg. Med. Chem. Lett. 2011, 21, 3232) was evaluated as an adjuvant in a vaccine setting. Cholesteryl-PEG-NH2 was first reacted with diethyleneglycol dinitrophenolcarbonate, followed by purification to isolate nitrophenolcarbonate activated cholesteryl-PEG. Subsequently, IMDQ was conjugated at its aliphatic amine position to the PEG through a carbamate bond (FIG. 11A). See Example 1, supra.

As discussed in Example 1, cholesteryl-PEG-IMDQ amphiphile induces local innate immune activation in draining lymphoid tissues, while avoiding systemic inflammation. Moreover, as discussed in Example 1, a single shot vaccine comprising recombinant SARS-CoV-2 spike protein adjuvanted with cholesteryl-PEG-IMDQ mounts neutralizing antibody responses and provides protection against subsequent viral challenges.

To further elucidate the adjuvanticity of cholesteryl-PEG-IMDQ, cholesteryl-PEG-IMDQ was admixed (i.e., without aiming to form an antigen-adjuvant complex) to ovalbumin (OVA) as a model antigen for quantification of the induced immune response after primary and boost immunizations (FIGS. 11B1 and 11B2). Interestingly, whereas the magnitude of the primary CD8+ T cell response to OVA+cholesteryl-PEG-IMDQ was lower as compared to the response induced by the combination of OVA and the well-established commercially-available adjuvant Montanide, (Coffman et al., Immunity 2010, 33, 492; Wei et al., ACS Cent. Sci. 2020, 2020, 412; Kuai et al., Nat. Mater. 2017, 16, 489) the magnitude of the secondary response was significantly higher. Indeed, while secondary immunization with Montanide seemed to inhibit the immune response, secondary immunization with cholesteryl-PEG-IMDQ significantly boosted antigen-specific CD8+ T cells (FIGS. 11B1 and 11B2). Additionally, cholesteryl-PEG-IMDQ and Montanide induced CD8+ T cell responses of different quality. The former induced mostly cells with a $KLRG1^{+}CD127^{-}$ phenotype indicative of effector cells with immediate cytotoxic potential; the latter preferentially induced the development of $KLRG1^{-}CD127^{+}$ memory precursors (FIGS. 11C1 and 11C2). The quality of the antibody response also differed between cholesteryl-PEG-IMDQ and Montanide adjuvanted vaccines. Cholesteryl-PEG-IMDQ induced high titers of anti-OVA IgG2a and IgG2c isotypes, whereas Montanide induced mostly anti-OVA IgG1 (FIG. 11D). Combined, these results highlight the potential of cholesteryl-PEG-IMDQ amphiphiles as vaccine adjuvants inducing qualitatively different immune responses as compared to commonly used adjuvants, which may ease the development of vaccination strategies tailored to diseases where protection is conferred by different immune mechanisms.

10. EMBODIMENTS

The following are exemplary embodiments:

1. A compound having the following structure:

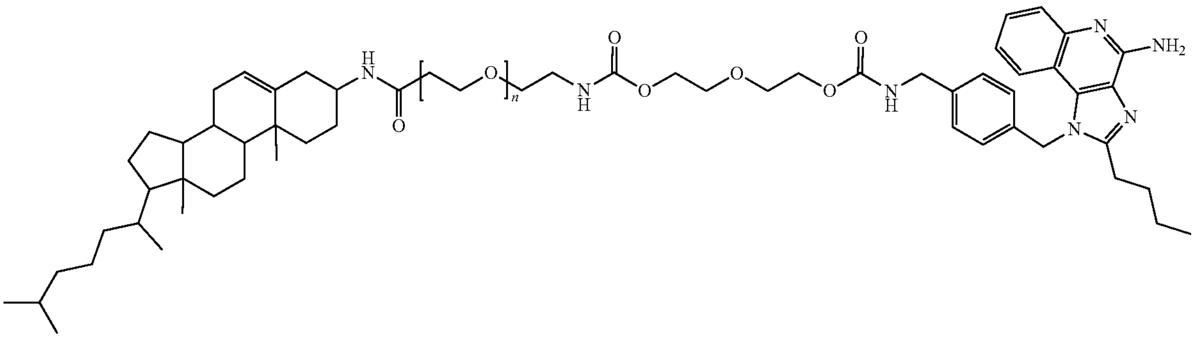

or an enantiomer, a mixture of enantiomers, a tautomer, or a pharmaceutically acceptable salt thereof, wherein n is an integer from 10 to 200.

2. A compound having the following structure:

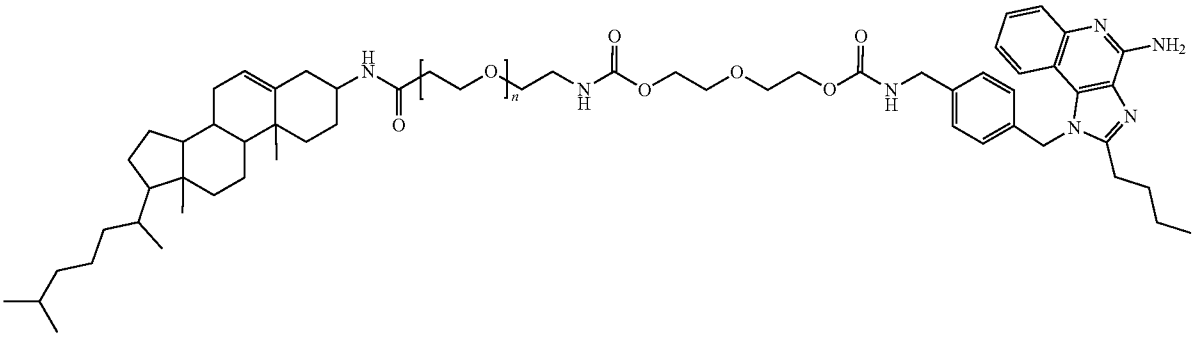

wherein n is an integer from 10 to 200.

3. A pharmaceutical composition comprising the compound of embodiment 1 or 2, and a pharmaceutically acceptable carrier.

4. An immunogenic composition comprising the compound of embodiment 1 or 2, and an antigen of interest.

5. The immunogenic composition of embodiment 4, wherein the antigen of interest is a SARS-CoV-2 antigen.

6. The immunogenic composition of embodiment 5, wherein the SARS-CoV-2 antigen comprises a SARS-CoV-2 spike protein ectodomain with amino acid substitutions of RRAR to A at amino acid residues corresponding to amino acid residues 682 to 685 of GenBank Accession No. MN908947.3, and amino acid substitutions to prolines at amino acid residues corresponding to amino acid residues 986 and 987 of GenBank Accession No. MN908947.3.

7. The immunogenic composition of embodiment 6, wherein the ectodomain is directly or indirectly linked to a trimerization domain.

8. The immunogenic composition of embodiment 7, wherein the trimerization domain is a T4 foldon trimerization domain.

9. The immunogenic composition of any one of embodiments 6 to 8, wherein the SARS-CoV2 antigen comprises a tag.

10. The immunogenic composition of embodiment 7 or 8, wherein the trimerization domain is directly or indirectly linked to a tag.

11. The immunogenic composition of embodiment 9 or 10, wherein the tag is a hexa-histidine tag or flag tag.

12. The immunogenic composition of embodiment 4, wherein the antigen of interest comprises an inactivated virus.

13. The immunogenic composition of embodiment 12, wherein the inactivated virus is influenza virus.

14. The immunogenic composition of embodiment 4, wherein the antigen of interest is a trivalent or quadravalent inactivated influenza virus composition.

15. The immunogenic composition of embodiment 4, wherein the antigen of interest comprises a split influenza virus.

16. The immunogenic composition of embodiment 4, wherein the antigen of interest is an infectious disease antigen.

17. The immunogenic composition of embodiment 4, wherein the antigen of interest is a viral antigen, a bacteria antigen, a fungal antigen, or a parasitic antigen.

18. The immunogenic composition of embodiment 4, wherein the antigen of interest is a RSV antigen, human Metapneumovirus antigen, MERS-CoV antigen, Lassa virus antigen, Japanese encephalitis antigen, or hepatitis A virus antigen.

19. The immunogenic composition of embodiment 4, wherein the antigen of interest is a *Clostridium tetani* antigen, *Bacillus* antigen, *Bordetella pertussis* antigen, *Streptococcus pneumoniae* antigen, *Neisseria meningitides* antigen, *Haemophilus influenzae* antigen, or *Corynebacterium* diphtherias antigen.

20. The immunogenic composition of embodiment 19, wherein the *Bacillus* antigen is a *Bacillus anthracis* antigen.

21. A method of inducing an immune response to an antigen of interest in a subject, comprising administering to the subject the immunogenic composition of any one of embodiments 4 to 20.

22. A method for immunizing a subject against a disease or disorder caused by or associated with an antigen, comprising administering the immunogenic composition of any one of embodiments 4 to 20.

23. A method for immunizing a subject against COVID-19, comprising administering to the subject the immunogenic composition of any one of embodiments 5 to 11.

24. A method for immunizing a subject against influenza virus disease, comprising administering to the subject the immunogenic composition of embodiment 13, 14, or 15.

25. A method for preventing a disease or disorder caused by or associated with an antigen in a subject, comprising administering the immunogenic composition of any one of embodiments 4 to 20.

26. A method for preventing COVID-19 in a subject, comprising administering to the subject the immunogenic composition of any one of embodiments 5 to 11.

27. A method for preventing influenza virus disease in a subject, comprising administering to the subject the immunogenic composition of embodiment 13, 14, or 15.

28. The method of any one of embodiments 21 to 27, wherein the immunogenic composition is administered subcutaneously or intramuscularly.

29. A method of inducing an immune response to an antigen of interest in a subject, comprising administering to the subject the pharmaceutical composition of embodiment 3 and an immunogenic composition comprising an antigen of interest.

30. A method of immunizing a subject against a disease or disorder caused by or associated with an antigen, comprising administering to the subject the pharmaceutical composition of embodiment 3 and an immunogenic composition comprising an antigen of interest.

31. A method of immunizing a subject against COVID-19, comprising administering to the subject the pharmaceutical composition of embodiment 3 and an immunogenic composition comprising a SARS-CoV-2 antigen.

32. A method of immunizing a subject against influenza virus disease, comprising administering to the subject the pharmaceutical composition of embodiment 3 and an immunogenic composition comprising an influenza virus antigen.

33. A method of preventing a disease or disorder caused by or associated with an antigen in a subject, comprising administering to the subject the pharmaceutical composition of embodiment 3 and an immunogenic composition comprising an antigen of interest.

34. A method of preventing COVID-19 in a subject, comprising administering to the subject the pharmaceutical composition of embodiment 3 and an immunogenic composition comprising a SARS-CoV-2 antigen.

35. A method of preventing influenza virus disease in a subject, comprising administering to the subject the pharmaceutical composition of embodiment 3 and an immunogenic composition comprising an influenza virus antigen.

36. The method of embodiment 31 or 34, wherein the SARS-CoV-2 antigen comprises a SARS-CoV-2 spike protein ectodomain with amino acid substitutions of RRAR to A at amino acid residues corresponding to amino acid residues 682 to 685 of GenBank Accession No. MN908947.3, and amino acid substitutions to prolines at amino acid residues corresponding to amino acid residues 986 and 987 of GenBank Accession No. MN908947.3.

37. The method of embodiment 36, wherein the ectodomain is directly or indirectly linked to a trimerization domain.

38. The method of embodiment 37, wherein the trimerization domain is a T4 foldon trimerization domain.

39. The method of any one of embodiments 36 to 38, wherein the SARS-CoV2 antigen comprises a tag.

40. The method of embodiment 37 or 38, wherein the trimerization domain is directly or indirectly linked to a tag.

41. The method of embodiment 39 or 40, wherein the tag is a hexa-histidine tag or flag tag.

42. The method of embodiment 32 or 35, wherein the antigen of interest comprises an inactivated virus.

43. The method of embodiment 42, wherein the inactivated virus is influenza virus.

44. The method of embodiment 42, wherein the antigen of interest is a trivalent or quadravalent inactivated influenza virus composition.

45. The method of embodiment 42, wherein the antigen of interest comprises a split influenza virus.

46. The method of embodiment 29, 30 or 33, wherein the antigen of interest is an infectious disease antigen.

47. The method of embodiment 29, 30 or 33, wherein the antigen of interest is a viral antigen, a bacteria antigen, a fungal antigen, or a parasitic antigen.

48. The method of embodiment 29, 30 or 33, wherein the antigen of interest is a RSV antigen, human Metapneumovirus antigen, MERS-CoV antigen, Lassa virus antigen, Japanese encephalitis antigen, or hepatitis A virus antigen.

49. The method of embodiment 29, 30 or 33, wherein the antigen of interest is a *Clostridium tetani* antigen, *Bacillus* antigen, *Bordetella pertussis* antigen, *Streptococcus pneumoniae* antigen, *Neisseria meningitides* antigen, *Haemophilus influenzae* antigen, or *Corynebacterium* diphtherias antigen.

50. The method of embodiment 49, wherein the *Bacillus* antigen is a *Bacillus anthracis* antigen.

51. The method of any one of embodiments 29 to 50, wherein the pharmaceutical composition and the immunogenic composition are administered to the subject concurrently.

52. The method of embodiment of any one of embodiments 29 to 50, wherein the pharmaceutical composition is administered to the subject prior to the administration of the immunogenic composition.

53. The method of embodiment of any one of embodiments 29 to 50, wherein the pharmaceutical composition is administered to the subject after the administration of the immunogenic composition.

54. The method of any one of embodiments 29 to 53, wherein the pharmaceutical composition and immunogenic composition are administered to the subject by the same route of administration.

55. The method of embodiment 54, wherein the route of administration is subcutaneous or intramuscular.

56. The method of any one of embodiments 29 to 53, wherein the pharmaceutical composition and the immunogenic composition are administered to the subject by different routes of administration.

57. The method of any one of embodiments 29 to 55, wherein the pharmaceutical composition and the immunogenic composition are administered to the same region of the subject.

58. A method for enhancing the immune response to an antigen of interest in a subject, comprising administering to the subject the compound of embodiment 1 or 2 in an immunogenic composition comprising the antigen of interest.

59. A method for enhancing the immune response to an antigen of interest in a subject, comprising administering to the subject the immunogenic composition of any one of embodiments 4 to 20.

60. A method for enhancing the immune response to an antigen of interest in a subject, comprising administering to the subject the pharmaceutical composition of embodiment 3 and an immunogenic composition comprising the antigen of interest.

61. The method of embodiment 60, wherein the pharmaceutical composition and the immunogenic composition are administered to the subject concurrently.

62. The method of embodiment 60, wherein the pharmaceutical composition is administered to the subject prior to the administration of the immunogenic composition.

63. The method of embodiment 60, wherein the pharmaceutical composition is administered to the subject after the administration of the immunogenic composition.

64. The method of any one of embodiments 60 to 63, wherein the pharmaceutical composition and immunogenic composition are administered to the subject by the same route of administration.

65. The method of embodiment 64, wherein the route of administration is subcutaneous or intramuscular.

66. The method of any one of embodiments 60 to 63, wherein the pharmaceutical composition and the immunogenic composition are administered to the subject by different routes of administration.

67. The method of any one of embodiments 60 to 65, wherein the pharmaceutical composition and the immunogenic composition are administered to the same region of the subject.

68. The method of any one of embodiments 58 to 67, wherein the immune response to the antigen of interest is at least 10%, at least 25%, at least 30%, at least 40% or at least 50% higher than the immune response to the antigen of interest without the administration of the compound.

69. The method of embodiment 68, wherein the immune response is a humoral immune response.

70. The method of embodiment 68 or 69, wherein the immune response is a cellular immune response.

71. The method of any one of embodiments 58 to 70, wherein the antigen of interest is a SARS-CoV-2 antigen.

72. The method of embodiment 71, wherein the SARS-CoV-2 antigen comprises a SARS-CoV-2 spike protein ectodomain with amino acid substitutions of RRAR to A at amino acid residues corresponding to amino acid residues 682 to 685 of GenBank Accession No. MN908947.3, and amino acid substitutions to prolines at amino acid residues corresponding to amino acid residues 986 and 987 of GenBank Accession No. MN908947.3.

73. The method of embodiment 72, wherein the ectodomain is directly or indirectly linked to a trimerization domain.

74. The method of embodiment 73, wherein the trimerization domain is a T4 foldon trimerization domain.

75. The method of any one of embodiments 72 to 74, wherein the SARS-CoV2 antigen comprises a tag.

76. The method of embodiment 73 or 74, wherein the trimerization domain is directly or indirectly linked to a tag.

77. The method of embodiment 75 or 76, wherein the tag is a hexa-histidine tag or flag tag.

78. The method of embodiment 58 to 70, wherein the antigen of interest comprises an inactivated virus.

79. The method of embodiment 78, wherein the inactivated virus is influenza virus.

80. The method of embodiment 78, wherein the antigen of interest is a trivalent or quadravalent inactivated influenza virus composition.

81. The method of embodiment 78, wherein the antigen of interest comprises a split influenza virus.

82. The method of any one of embodiments 58 to 70, wherein the antigen of interest is an infectious disease antigen.

83. The method of any one of embodiments 58 to 70, wherein the antigen of interest is a viral antigen, a bacteria antigen, a fungal antigen, or a parasitic antigen.

84. The method of any one of embodiments 58 to 70, wherein the antigen of interest is a RSV antigen, human Metapneumovirus antigen, MERS-CoV antigen, Lassa virus antigen, Japanese encephalitis antigen, or hepatitis A virus antigen.

85. The method of any one of embodiments 58 to 70, wherein the antigen of interest is a *Clostridium tetani* antigen, *Bacillus* antigen, *Bordetella pertussis* antigen, *Streptococcus pneumoniae* antigen, *Neisseria meningitides* antigen, *Haemophilus influenzae* antigen, or *Corynebacterium* diphtherias antigen.

86. The method of embodiment 85, wherein the *Bacillus* antigen is a *Bacillus anthracis* antigen.

87. The method of any one of embodiments 58 to 70, wherein the antigen of interest is a cancer antigen.

88. The method of any one of embodiments 21 to 87, wherein the subject is human.

89. A compound of embodiment 1 or 2 for use in the preparation of a medicament for use inducing an immune response to an antigen of interest in a subject.

90. A compound of embodiment 1 or 2 for use in the preparation of a medicament for use in enhancing an immune response to an antigen of interest in a subject.

91. The pharmaceutical composition of embodiment 3 for use in a method for enhancing an immune response to an immunogenic composition comprising an antigen of interest in a subject.

92. The immunogenic composition of any one of embodiments 4 to 20 for use in a method for inducing an immune response to the antigen of interest in a subject.

93. The pharmaceutical composition of embodiment 3 for use in a method for inducing an immune response to an antigen of interest in a subject comprising administrating an immunogenic composition comprising the antigen of interest to the subject.

94. The compound of embodiment 89 or 90, wherein the subject is a human.

95. The composition of embodiment 91, 92, or 93, wherein the subject is a human.

The invention is not to be limited in scope by the specific embodiments described herein. Indeed, various modifications of the invention in addition to those described will become apparent to those skilled in the art from the foregoing description and accompanying Figures. Such modifications are intended to fall within the scope of the appended claims.

All references cited herein are incorporated herein by reference in their entirety and for all purposes to the same extent as if each individual publication or patent or patent application was specifically and individually indicated to be incorporated by reference in its entirety for all purposes.

What is claimed is:

1. A compound having the following structure:

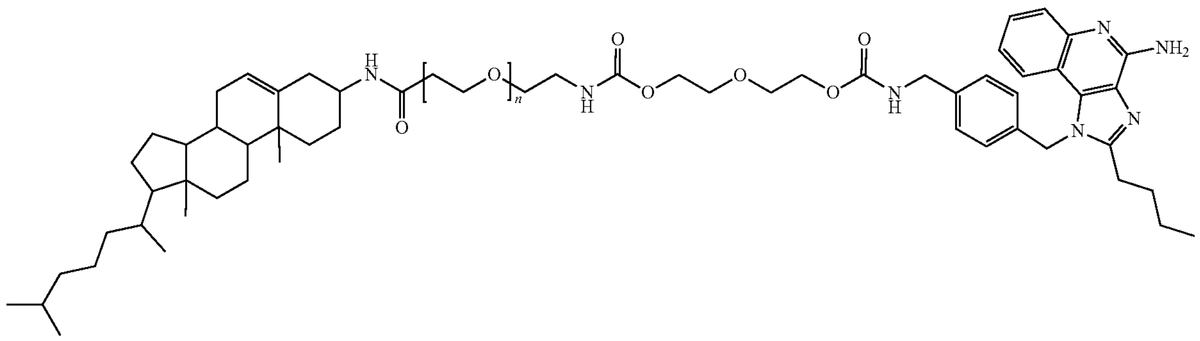

or an enantiomer, a mixture of enantiomers, a tautomer, or a pharmaceutically acceptable salt thereof, wherein n is an integer from 10 to 200.

2. A pharmaceutical composition comprising the compound of claim 1, and a pharmaceutically acceptable carrier.

3. An immunogenic composition comprising the compound of claim 1, and an antigen of interest.

4. The immunogenic composition of claim 3, wherein the antigen of interest is a SARS-COV-2 antigen.

5. The immunogenic composition of claim 4, wherein the SARS-CoV-2 antigen comprises a SARS-COV-2 spike protein ectodomain with amino acid substitutions of RRAR to A at amino acid residues corresponding to amino acid residues 682 to 685 of GenBank Accession No. MN908947.3, and amino acid substitutions to prolines at amino acid residues corresponding to amino acid residues 986 and 987 of GenBank Accession No. MN908947.3.

6. The immunogenic composition of claim 5, wherein the ectodomain is directly or indirectly linked to a trimerization domain.

7. The immunogenic composition of claim 6, wherein the trimerization domain is a T4 foldon trimerization domain.

8. The immunogenic composition of claim 5, wherein the SARS-Co-V2 antigen comprises a tag.

9. The immunogenic composition of claim 6, wherein the trimerization domain is directly or indirectly linked to a tag.

10. The immunogenic composition of claim 8, wherein the tag is a hexa-histidine tag or flag tag.

11. The immunogenic composition of claim 3, wherein the antigen of interest comprises an inactivated virus.

12. The immunogenic composition of claim 11, wherein the inactivated virus is influenza virus.

13. The immunogenic composition of claim 3, wherein the antigen of interest is a trivalent or quadravalent inactivated influenza virus composition.

14. The immunogenic composition of claim 3, wherein the antigen of interest comprises a split influenza virus.

15. The immunogenic composition of claim 3, wherein the antigen of interest is an infectious disease antigen.

16. The immunogenic composition of claim 3, wherein the antigen of interest is a viral antigen, a bacteria antigen, a fungal antigen, or a parasitic antigen.

17. The immunogenic composition of claim 3, wherein the antigen of interest is a RSV antigen, human Metapneumovirus antigen, MERS-COV antigen, Lassa virus antigen, Japanese encephalitis antigen, or hepatitis A virus antigen.

18. The immunogenic composition of claim 3, wherein the antigen of interest is a *Clostridium tetani* antigen, *Bacillus* antigen, *Bordetella pertussis* antigen, *Streptococcus pneumoniae* antigen, *Neisseria meningitides* antigen, *Haemophilus influenzae* antigen, or *Corynebacterium diphtheriae* antigen.

19. The immunogenic composition of claim 18, wherein the *Bacillus* antigen is a *Bacillus anthracis* antigen.

20. The pharmaceutical composition of claim 2 for use in a method for enhancing an immune response to an immunogenic composition comprising an antigen of interest in a subject.

21. The immunogenic composition of claim 3 for use in a method for inducing an immune response to the antigen of interest in a subject.

22. The pharmaceutical composition of claim 2 for use in a method for inducing an immune response to an antigen of interest in a subject comprising administrating an immunogenic composition comprising the antigen of interest to the subject.

* * * * *